US011041069B2

(12) United States Patent
Capasso Palmiero et al.

(10) Patent No.: US 11,041,069 B2
(45) Date of Patent: Jun. 22, 2021

(54) GENE DELIVERY CARRIER

(71) Applicants: Massachusetts Institute of Technology, Cambridge, MA (US); POLITECNICO DI MILANO, Milan (IT)

(72) Inventors: Umberto Capasso Palmiero, Zürich (CH); James C. Kaczmarek, Somerville, MA (US); Daniel Griffith Anderson, Framingham, MA (US); Davide Moscatelli, Arese (IT)

(73) Assignees: Massachusetts Institute of Technology, Cambridge, MA (US); Politecnico di Milano, Milan (IT)

(*) Notice: Subject to any disclaimer, the term of this patent is extended or adjusted under 35 U.S.C. 154(b) by 0 days.

(21) Appl. No.: 16/179,698

(22) Filed: Nov. 2, 2018

(65) Prior Publication Data

US 2019/0194444 A1    Jun. 27, 2019

Related U.S. Application Data

(60) Provisional application No. 62/661,864, filed on Apr. 24, 2018, provisional application No. 62/581,277, filed on Nov. 3, 2017.

(51) Int. Cl.
| | | |
|---|---|---|
| *C08L 33/14* | (2006.01) | |
| *C08F 20/34* | (2006.01) | |
| *C08G 73/02* | (2006.01) | |
| *C12N 15/87* | (2006.01) | |
| *C08G 63/685* | (2006.01) | |
| *A61K 48/00* | (2006.01) | |

(52) U.S. Cl.
CPC .......... *C08L 33/14* (2013.01); *A61K 48/0041* (2013.01); *C08F 20/34* (2013.01); *C08G 63/6852* (2013.01); *C08G 73/02* (2013.01); *C12N 15/87* (2013.01); *C08L 2201/06* (2013.01); *C08L 2203/02* (2013.01); *C12N 2310/14* (2013.01)

(58) Field of Classification Search
None
See application file for complete search history.

(56) References Cited

U.S. PATENT DOCUMENTS 4,883,689 A    11/1989   Gradeff et al.

FOREIGN PATENT DOCUMENTS

| GB | 1257638 | 12/1971 |
|---|---|---|
| JP | H06-122731 | 5/1994 |
| WO | WO 2014/136100 | 9/2014 |

OTHER PUBLICATIONS

Green et al., "A Combinatorial Polymer Library Approach Yields Insight into Nonviral Gene Delivery," Oct. 25, 2007.*
PCT/US2018/058898, Jan. 3, 2019, International Search Report and Written Opinion.
International Search Report and Written Opinion for PCT/US2018/058898, dated Feb. 22, 2019.
Arote et al., A biodegradable poly(ester amine) based on polycaprolactone and polyethylenimine as a gene carrier. Biomaterials. Feb. 2007;28(4):735-44. Epub Oct. 10, 2006.
Fenton et al., Bioinspired Alkenyl Amino Alcohol Ionizable Lipid Materials for Highly Potent In Vivo mRNA Delivery. Adv Mater. Apr. 20, 2016;28(15):2939-43. doi: 10.1002/adma.201505822. Epub Feb. 18, 2016.
Kaczmarek et al., Polymer-Lipid Nanoparticles for Systemic Delivery of mRNA to the Lungs. Angew Chem Int Ed Engl. Oct. 24, 2016;55(44):13808-13812. doi: 10.1002/anie.201608450. Epub Sep. 30, 2016.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
PCT/US2018/058898, May 14, 2020, International Preliminary Report on Patentability.
International Preliminary Report on Patentability for PCT/US2018/058898, dated May 14, 2020.
[No authors listed], HIV Vaccine Failure Prompts Merck to Halt Trial. Nature, 2007;449:390.
Anderson et al., Semi-automated synthesis and screening of a large library of degradable cationic polymers for gene delivery. Angew Chem Int Ed Engl. Jul. 14, 2003;42(27):3153-8. doi: 10.1002/anie.200351244. PMID: 12866105.
Bobo et al., Nanoparticle-Based Medicines: A Review of FDA-Approved Materials and Clinical Trials to Date. Pharmaceutical Research, 2016, 33, 2373-2387.
Carai et al., Central Effects of 1,4-Butanediol are Mediated by GABA(B) Receptors via its Conversion into γ-Hydroxybutyric Acid. European Journal of Pharmacology, 2002, 441, 157-163.
Carothers, Polymers and Polyfunctionality. Transactions of the Faraday Society, 1936, 32, 39-49.
Chen et al., Production and Clinical Development of Nanoparticles for Gene Delivery. Mol. Ther. Methods Clin. Dev., 2016, 3, 16023.
Dash et al., Poly-ε-caprolactone Based Formulations for Drug Delivery and Tissue Engineering: A Review. Journal of Controlled Release, 2012, 158, 15-33.
Eltoukhy et al., Degradable Terpolymers with Alkyl Side Chains Demonstrate Enhanced Gene Delivery Potency and Nanoparticle Stability. Advanced Materials, 2013, 25, 1487-1493.

(Continued)

*Primary Examiner* — Jared Barsky
(74) *Attorney, Agent, or Firm* — Wolf, Greenfield & Sacks, P.C.

(57) ABSTRACT

Disclosed are methods, compositions, reagents, systems, and kits to prepare and utilize poly (β-amino ester) (PBAE) polymers, which are synthesized via Michael addition reactions of diacrylates and amines disclosed herein. Various embodiments utilize lactones and lactone derivatives to generate the diacrylate compounds. The PBAE polymers are shown to be effective biodegradable carriers for the delivery of an agent such as an organic molecule, inorganic molecule, nucleic acid, protein, peptide, polynucleotide, targeting agent, an isotopically labeled chemical compound, vaccine, or an immunological agent.

23 Claims, 26 Drawing Sheets

Specification includes a Sequence Listing.

(56) References Cited

OTHER PUBLICATIONS

Eltoukhy et al., Effect of Molecular Weight of Amine End-modified Poly (β-amino ester) s on Gene Delivery Efficiency and Toxicity. Biomaterials. 2012, 33, 3594-3603.
Fenton et al., Bioinspired Alkenyl Amino Alcohol Ionizable Lipid Materials for Highly Potent in Vivo mRNA Delivery. Advanced Materials, 2016, 28, 2939-2943.
Ferrari et al., ε-Caprolactone-based Macromonomers Suitable for Biodegradable Nanoparticles Synthesis Through Free Radical Polymerization. Macromolecules, 2011, 44, 9205-9212.
Gilboa et al., Cancer Immunotherapy with mRNA-transfected Dendritic Cells. Immunological Reviews, 2004, 199, 251-263.
Gore et al., Executive Summary to EDC-2: The Endocrine Society's Second Scientific Statement on Endocrine-Disrupting Chemicals. Endocrine Reviews, 2015, 36, 593-602.
Gori et al., Delivery and Specificity of CRISPR/Cas9 Genome Editing Technologies for Human Gene Therapy. Human Gene Therapy, 2015, 26, 443-451.
Guerrero-Cázares et al., Biodegradable Polymeric Nanoparticles Show High Efficacy and Specificity at DNA Delivery to Human Glioblastoma in Vitro and in Vivo. ACS Nano, 2014, 8, 5141-5153.
Hashimoto et al., Electroporation Enables the Efficient mRNA Delivery into the Mouse Zygotes and Facilitates CRISPR/Cas9-based Genome Editing. Scientific Reports, 2015, 5.
Jin et al., Current Progress in Gene Delivery Technology Based on Chemical Methods and Nano-carriers. Theranostics 2014, 4, 240-255.
Kaczmarek et al., Polymer-Lipid Nanoparticles for Systemic Delivery of mRNA to the Lungs. Angewandte Chemie, 2016, 55, 13808-13812.
Kamat et al., Lung Cancer in Vitro and in Vivo. Molecular Cancer Therapeutics, 2013, 12, 405-415.
Kauffman et al., Optimization of Lipid Nanoparticle Formulations for mRNA Delivery in Vivo with Fractional Factorial and Definitive Screening Designs. Nano letters, 2015, 15, 7300-7306.
Khosravi-Darani et al., Calcium Based Non-viral Gene Delivery: An Overview of Methodology and Applications. Acta Med Iranica, 2010, 48, 133-141.
Kim et al., Differential polymer Strucute Tunes Mechanism of Cellular Upatke and Transfection Routes of Poly (β-amino ester) Polyplexes in Human Breast Cancer Cells. Bioconjugate Chemistry, 2013, 25, 43-51.
Kranz et al., Systemic RNA Delivery to Dendritic Cells Exploits Antiviral Defence for Cancer Immunotherapy. Nature, 2016, 534, 396-401.
Kumari et al., Biodegradable Polymeric Nanoparticles Based Drug Delivery Systems. Colloids and Surfaces B: Biointerfaces, 2010, 75, 1-18.
Luten et al., Biodegradable Polymers as Non-viral Carriers for Plasmid DNA Delivery. J Control Release, 2008, 126, 97-110.
Mangraviti et al., Polymeric Nanoparticles for Nonviral Gene Therapy Extend Brain Tumor Survival in Vivo. ACS Nano, 2015, 9, 1236-1249.
Matsui et al., Messenger RNA-based Therapeutics for the Treatment of Apoptosis-associated Diseases. Scientific Reports 2015, 5.
McNamara et al., RNS-based Vaccines in Cancer Immunotherapy. Journal of Immunology Research, 2015, 2015.
Mirmira et al., Obesity, and Type 2 Diabetes Mellitus: Genuine Concern or Unnecessary Preoccupation? Translational Research, 2014, 164, 13-21.
Mulligan, The Basic Science of Gene Therapy. Science, 1993, 260, 926-932.
Pollard et al., Challenges and Advances Towards the Rational Design of mRNA Vaccines. Trends in Molecular Medicine, 2013, 19, 705-713.
Robinson et al., Nucleic acid immunizations. Curr. Protoc. Immunol. 2001, Chapter 2: Unit 2.14.
Satta et al., *Drosophila* Metabolize 1,4-Butanediol into γ-Hydroxybutyric Acid in Vivo. European Journal of Pharmacology, 2003, 473, 149-152.
Sergeeva et al., mRNA-based therapeutics—Advances and perspectives. Biochemistry (Moscow) 2016, 81, 709-722.
Sunshine et al., Small-Molecule End-Groups of Linear Polymer Determin Cell-type Gene-Delivery Efficacy. Advanced Materials, 2009, 21, 4947-4951.
Sunshine et al., Poly (β-amino ester)-nanoparticle Mediated Transfection of Retinal Pigment Epithelial Cells in Vitro and in Vivo. PloS one, 2012, 7, e37543.
Sunshine et al., Small-Molecule End-Groups of Linear Polymer Determine Cell-type Gene-Delivery Efficacy. Advanced Materials, 2009, 21, 4947-4951.
Tzeng et al., Cystamine-terminated Poly (beta-amino ester)s for siRNA Delivery to Human Mesenchymal Stem Cells and Enhancement of Osteogenic Differentiation. Biomaterials, 2012, 33, 8142-8151.
Vu et al., Generation of a Focused Poly (amino ether) Library: Polymer-mediated Transgene Delivery and Gold-nanorod Based Theranostic Systems. Theranostics. 2012, 2, 1160-1173.
Wang et al., One-step Generation of Mice Carrying Mutations in Multiple Genes by CRISPR/Cas-mediated Genome Engineering. Cell, 2013, 153, 910-918.
Weiss et al., mRNA Vaccination as a Safe Approach for Specific Protection from Type I Allergy. Expert Review of Vaccines, 2012, 11, 55-67.
Zhao et al., Synthesis of Amphiphilic Poly (β-amino ester) for Efficiently Minicircle DNA Delivery in Vivo. ACS Applied Materials & Interfaces, 2016, 8, 19284-19290.
Zhou et al., Highly Branched Poly (β-amino ester)s for Skin Gene Therapy. Journal of Controlled Release, 2016, 244, 336-346.

\* cited by examiner

Characterization of the PCL-based diacrylates

| Sample | $q_{Theory}$ [h] | $q_{NMR}$* [-] | $Mn_{Theory}$ [Da] | $Mn_{NMR}$ [Da] | $Mn_{GPC}$ [Da] | $Đ_{GPC}$ [-] |
|---|---|---|---|---|---|---|
| A | 0 | - | 170 | - | - | - |
| B | 3 | 3.3 | 513 | 551 | 811 | 1.27 |
| C | 5 | 5.6 | 741 | 809 | 1233 | 1.21 |
| D | 7 | 7.2 | 969 | 995 | 1499 | 1.30 |

* evaluated according to: $q = \frac{H}{2} + 1$, where H is the area under curve of the corresponding protons in Figure 8B

Figure 8A

GPC characterization of PBAEs

| Sample | $M_{w,GPC}$ [Da] | $Đ_{,GPC}$ [-] |
|---|---|---|
| A1 | 866 | 1.53 |
| A2 | 1121 | 1.71 |
| A3 | 896 | 1.37 |
| A4 | 983 | 1.76 |
| B1 | 1753 | 2.20 |
| B2 | 1916 | 2.33 |
| B3 | 1689 | 2.11 |
| B4 | 1782 | 2.13 |
| C1 | 2206 | 2.26 |
| C2 | 2265 | 2.42 |
| C3 | 2115 | 2.41 |
| C4 | 2371 | 2.45 |
| D1 | 2394 | 2.43 |
| D2 | 2772 | 2.56 |
| D3 | 2342 | 2.35 |
| D4 | 2755 | 2.50 |

Figure 9

Characterization of PBAE NPs 0% PEG

| Sample | $Dn_W$ [nm] | $PDI_W$ [-] | $Zp_W$ [mV] | $Dn_{PBS}$ [nm] | $PDI_{PBS}$ [-] |
|---|---|---|---|---|---|
| A2 | 146.0 | 0.117 | 21.0± 4.9 | 338.8 | 0.154 |
| B2 | 172.3 | 0.090 | 30.9± 8.1 | 382.7 | 0.316 |
| C2 | 189.3 | 0.132 | 37.7± 7.1 | 305.0 | 0.391 |
| D2 | 159.3 | 0.126 | 37.9± 8.3 | 589.3 | 0.344 |
| C1 | 190.1 | 0.125 | 35.9± 8.3 | 295.6 | 0.350 |

Figure 12A

Characterization of PBAE NPs 15% PEG

| Sample | $Dn_W$ [nm] | $PDI_W$ [-] | $Zp_W$ [mV] | $Dn_{PBS}$ [nm] | $PDI_{PBS}$ [-] |
|---|---|---|---|---|---|
| A2 | 145.3 | 0.095 | 11.2 ± 5.5 | 245.5 | 0.137 |
| B2 | 146.9 | 0.100 | 16.9 ± 9.6 | 143.0 | 0.132 |
| C2 | 170.0 | 0.102 | 15.8 ± 8.1 | 156.1 | 0.172 |
| D2 | 151.5 | 0.210 | 30.7 ± 7.5 | 171.1 | 0.427 |
| C1 | 163.6 | 0.198 | 14.6 ± 5.6 | 142.1 | 0.207 |

Figure 12B

Image of C1 24 hours after IV injection (0.5 mg/kg mRNA)

SEQUENCE LISTING

```
<160> NUMBER OF SEQ ID NOS: 1

<210> SEQ ID NO 1
<211> LENGTH: 1653
<212> TYPE: RNA
<213> ORGANISM: Artificial Sequence
<220> FEATURE:
<223> OTHER INFORMATION: Synthetic polynucleotide

<400> SEQUENCE: 1
auggaagaug ccaaaaacau uaagaagggc ccagcgccau ucuacccacu cgaagacggg      60
accgccggcg agcagcugca caaagccaug aagcgcuacg cccuggugcc cggcaccauc     120
gccuuuaccg acgcacauau cgagguggac auuaccuacg ccgaguacuu cgagaugagc     180
guucggcugg cagaagcuau gaagcgcuau gggcugaaua caaaccaucg gaucguggug     240
ugcagcgaga auagcuugca guucuucaug cccguguugg gugcccuguu caucggugug     300
gcuguggccc cagcuaacga caucuacaac gagcgcgagc ugcugaacag caugggcauc     360
agccagccca ccgucguauu cgugagcaag aaagggcugc aaaagauccu caacgugcaa     420
```

```
aagaagcuac cgaucauaca aaagaucauc aucauggaua gcaagaccga cuaccagggc    480
uuccaaagca uguacaccuu cgugacuucc cauuugccac ccggcuucaa cgaguacgac    540 uucgucccg  agagcuucga ccgggacaaa accaucgccc ugaucaugaa caguaguggc    600
aguaccggau ugcccaaggg cguagcccua ccgcaccgca ccgcuugugu ccgauucagu    660 caugccgcg  accccaucuu cggcaaccag aucaucccg  acaccgcuau ccucagcgug    720
gugccauuuc accacggcuu cggcauguuc accacgcugg gcuacuugau cugcggcuuu    780
cgggucgugc ucauguaccg cuucgaggag gagcuauucu ugcgcagcuu gcaagacuau    840
aagauucaau cugcccugcu ggugcccaca cuauuuagcu ucuucgcuaa gagcacucuc    900
aucgacaagu acgaccuaag caacuugcac gagaucgcca gcggcggggc gccgcucagc    960
aaggagguag gugaggccgu ggccaaacgc uuccaccuac caggcauccg ccagggcuac   1020
ggccugacag aaacaaccag cgccauucug aucaccccg  aaggggacga caagccuggc   1080
gcaguaggca aggugguucc cuucuucgag gcuaaggugg uggacuugga caccgguaag   1140
acacugggug ugaaccagcg cggcgagcug ugcguccgug gccccaugau caugagcggc   1200
uacguuaaca accccgaggc uacaaacgcu cucaucgaca aggacggcug gcugcacagc   1260
ggcgacaucg ccuacuggga cgaggacgag cacuucuuca ucguggaccg gcugaagagc   1320
cugaucaaau acaagggcua ccagguagcc ccagccgaac uggagagcau ccugcugcaa   1380
caccccaaca ucuucgacgc cggggucgcc ggccugcccg acgacgaugc cggcgagcug   1440
cccgccgcag ucgucgugcu ggaacacggu aaaaccauga ccgagaagga gaucguggac   1500
uauguggcca gccagguuac aaccgccaag aagcugcgcg gugguguugu guucguggac   1560
gaggugccua aaggacugac cggcaaguug gacgcccgca agauccgcga gauucucauu   1620
aaggccaaga agggcggcaa gaucgccgug uaa                                1653
```

GENE DELIVERY CARRIER

RELATED APPLICATIONS

This application claims priority under 35 U.S.C. § 119(e) to U.S. Provisional Application Ser. No. 62/581,277, filed on Nov. 3, 2017, and to U.S. Provisional Application Ser. No. 62/661,864, filed on Apr. 24, 2018, each of which is incorporated herein by reference in their entirety.

BACKGROUND OF THE INVENTION

Chemical materials have been widely used in biological research and medicine for the development of delivery systems for a variety of payloads including organic molecules, inorganic molecules, nucleic acids, proteins, peptides, polynucleotides, targeting agents, isotopically labeled chemical compounds, vaccines, and immunological agents.[1] In particular, chemical delivery systems, such as lipids, polymers, and hydrogels, have helped advance the field of gene delivery, in which efficacious delivery of naked polynucleotides to the site of interest is a challenge due to their clearance by the immune system, their inability to cross the cell membrane, and their potential degradation in lysosomes.[2]

Gene delivery is a process by which foreign nucleic acids (DNA and RNA) are transferred to host cells for applications such as genetic research or gene therapy. Gene delivery methods can be biological (e.g., viral or bacterial vectors), mechanical (e.g., microinjection, electroporation, or biolistics), or chemical (e.g., lipid or nanoparticle carriers).[1] The ideal gene delivery and transfection systems should have high transfection efficiency, high cell specificity, and low cell toxicity.

Biological gene delivery systems exhibit well-known adverse effects, such as immunogenicity and application limitations, such as difficulties in handling, difficulties in large-scale production, and limited length of the nucleic acid to be delivered.[3,4] Mechanical gene delivery methods also present several drawbacks. For example, mechanical methods cause damage to cells, and involve difficulty in large-scale manipulation, labor-intensive protocols, and/or the necessity of costly instruments.[5] To overcome the drawbacks of biological and mechanical systems, a variety of chemical gene delivery vehicles, such as calcium phosphates, lipids, and cationic polymers, including polyamidoamine dendrimers, polyethylenimine (PEI), poly (β-amino esters) (PBAEs), have been developed since the late 1960s.[6-8]

Cationic polymers are among the most common materials that have been used for gene delivery given their ability to electrostatically bind and condense nucleic acids to form nanoparticles.

Although many types of cationic polymers have been synthesized and tested as possible chemical delivery systems for gene delivery, such as polyethyleneimine (PEI), poly (amido-amine) (PAMAM), and poly (β-amino ester) (PBAE) polymers, only CALAA-01, a cyclodextrin containing polymer, has entered the clinic for siRNA delivery.[13] High net-positive charge and inability to undergo degradation under physiological conditions or the production of potentially toxic degradation products, which can accumulate in the body at hazardous levels, are the main reasons limiting clinical applications of known cationic polymers. Of the known cationic polymers, PBAEs are particularly useful due to their high transfection efficiency and biodegradability. As such, there remains a need for new, improved PBAEs for gene delivery.

SUMMARY OF THE INVENTION

Described herein are novel PBAEs derived from polylactone diacrylates. Poly-caprolactone (PCL) and poly-lactic acid (PLA) based polymers are useful in biomedical applications due to their biodegradability and biocompatibility.[14] Several PCL and PLA derivatives are already approved by the FDA for human use. However, existing PCL- and PLA-based polymers are not positively charged, and therefore are unsuitable for applications related to gene delivery. The use of polylactone-based diacrylates in the preparation of PBAEs is expected to produce PBAEs with high transfection efficiency and improved biocompatibility. Polylactone-based diacrylates can be synthesized via a novel two-step procedure that consists of (i) a ring opening polymerization of a lactone initiated by a mono-acrylate-containing nucleophile, and (ii) acylation of the polylactone mono-acrylate with an acryloyl electrophile. See FIG. 4.

The ring opening polymerization depicted in the first step in FIG. 4 is a so-called "living polymerization", a technique that allows control over the number of units of lactone monomers, which in turn allows for control over the polylactone's physical properties, such as molecular weight and lipophilicity.

Methods, compositions, reagents, systems, and kits for the preparation and utilization of polylactone-based PBAEs are also disclosed herein. In certain embodiments, a polylactone diacrylate is reacted with one or more amines in a step-growth polymerization to yield acrylate-terminated PBAEs. The terminal acrylate groups can be reacted with nucleophiles (e.g., amines) to form end-functionalized PBAEs. See FIG. 5.

In one aspect, provided herein is a polymer of Formula (I):

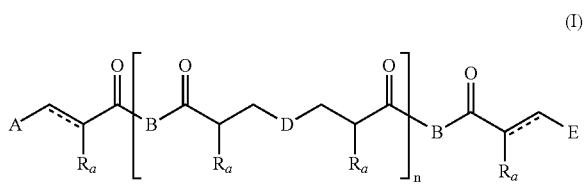

or a pharmaceutically acceptable salt thereof,
wherein:
  ═══ is a single bond or a double bond
  A is hydrogen or —XR$_3$;
  each B independently is a diradical of the formula:

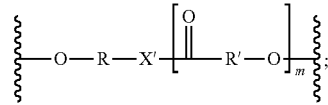

each D independently is:

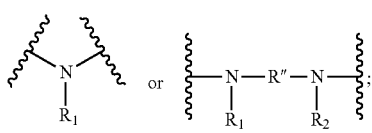

E is hydrogen or —XR$_4$;

each R, R', and R" independently is optionally substituted, cyclic or acyclic aliphatic; optionally substituted, cyclic or acyclic heteroaliphatic; or a combination thereof;

each R$_a$ independently is hydrogen or optionally substituted aliphatic;

R$_1$ and R$_2$ independently are selected from hydrogen; optionally substituted, cyclic or acyclic aliphatic; optionally substituted, cyclic or acyclic heteroaliphatic; optionally substituted aryl; optionally substituted heteroaryl; and a nitrogen protecting group; or R$_1$ and R$_2$ are combined to form a ring;

R$_3$ and R$_4$ independently are selected from hydrogen; optionally substituted, cyclic or acyclic aliphatic; optionally substituted, cyclic or acyclic heteroaliphatic; optionally substituted aryl; optionally substituted heteroaryl; and a protecting group;

X is O, S, NH, or NR$_X$, wherein R$_X$ is optionally substituted, cyclic or acyclic aliphatic; optionally substituted, cyclic or acyclic heteroaliphatic; optionally substituted aryl; or optionally substituted heteroaryl;

X' is O or NR$_y$, wherein R$_y$ is hydrogen or optionally substituted aliphatic;

each m independently is an integer between 1 and 100, inclusive;

n is an integer between 1 and 10,000, inclusive.

In certain embodiments, provided herein are polymers of Formulae (II), (III), (IV), and (V), and pharmaceutically acceptable salts thereof:

In another aspect, provided herein is a polylactone diacrylate compound of Formula (VI):

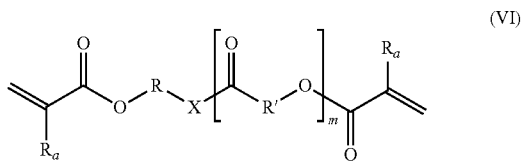

wherein:

R is optionally substituted, cyclic or acyclic aliphatic; optionally substituted, cyclic or acyclic heteroaliphatic; or a combination thereof;

each R' independently is optionally substituted, cyclic or acyclic aliphatic; optionally substituted, cyclic or acyclic heteroaliphatic; or a combination thereof;

each R$_a$ independently is hydrogen or optionally substituted aliphatic; and m is an integer between 1 and 100, inclusive.

In another aspect, the present disclosure provides methods of preparing polymers of Formulae (II), (III), (IV), and (V). In another aspect, the present disclosure provides methods of preparing compounds of Formula (VI).

In another aspect, the present disclosure provides compositions comprising a polymer described herein. In certain embodiments, the composition further comprises an agent, e.g., a small organic molecule, inorganic molecule, nucleic acid, protein, peptide, or polynucleotide.

In another aspect, provided herein are methods of treating a disease, disorder, or condition from which a subject suffers comprising administering to the subject in need thereof an effective amount of a composition described herein.

In another aspect, provided herein are methods of delivering a polynucleotide to a cell comprising contacting the cell with a composition described herein.

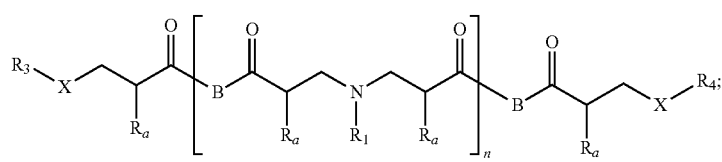

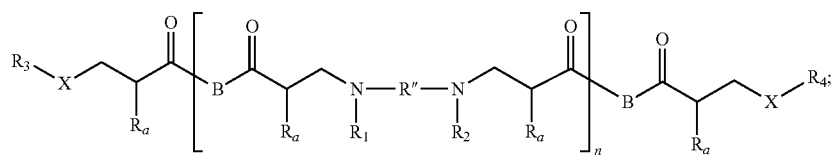

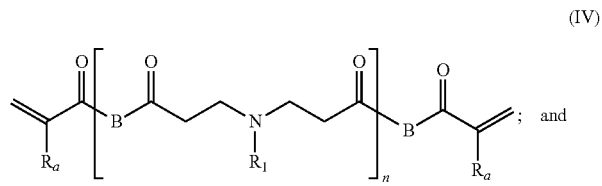

In another aspect, the present disclosure provides a kit comprising one or more components selected from the polymers and compounds described herein.

The details of certain embodiments of the invention are set forth in the Detailed Description of Certain Embodiments, as described below. Other features, objects, and advantages of the invention will be apparent from the Definitions, Figures, Examples, and Claims.

BRIEF DESCRIPTION OF THE DRAWINGS

FIGS. 8A to 8B show: (FIG. 8A) The characterization data for diacrylates A, B, C, and D. (FIG. 8B) $^1$H NMR spectrum and proton peak assignments of diacrylate C.

FIG. 9 shows the gell permeation chromatorphy (GPC) characterization of PBAE polymers prepared from amines (1, 2, 3, 4) and diacrylates (A, B, C, D).

(FIG. 10A) $M_w$ of the custom diacrylates and the PBAE polymers with different hydrophilic amines. (FIG. 10B) Transfection in HeLA cells of a PBAE series using direct mixing or pre-mixing protocol. (FIG. 10C) Transfection in HeLa cells using only pre-mixing protocol. (FIG. 10D) HeLa cell relative viability for all the synthesized PBAE polymers.

FIG. 12A shows the characterization data of selected mRNA-containing PBAE nanoparticles containing 0% PEG. FIG. 12B shows the characterization data of selected mRNA-containing PBAE nanoparticles containing 15% PEG.

(FIG. 13A) Serum stability of PBAE polymers with 5 CL unit (C) at 7 wt. % of PEG-lipid. (FIG. 13B) Serum stability of C1 at different wt. % of PEG-lipid. (FIG. 13C) Image of C1 24 hours after IV injection (0.5 mg/kg mRNA). (FIG. 13D) Liver enzyme activity of C1 and Jet PEI at a dose of 0.5 mg/kg. (FIG. 13E) Average radiance of C1 and JET PEI in the spleen after 24 hours at different mRNA doses. (FIG. 13F) Average radiance of C1 and JET PEI in the lungs after 24 hours at different mRNA doses.

(FIG. 14A) Transfection efficiency of PBAE 2 series with varying percentages of PEG-lipid. (FIG. 14B) Transfection efficiency of all PBAEs with 15 wt. % PEG-lipid.

DEFINITIONS

Figure 1:
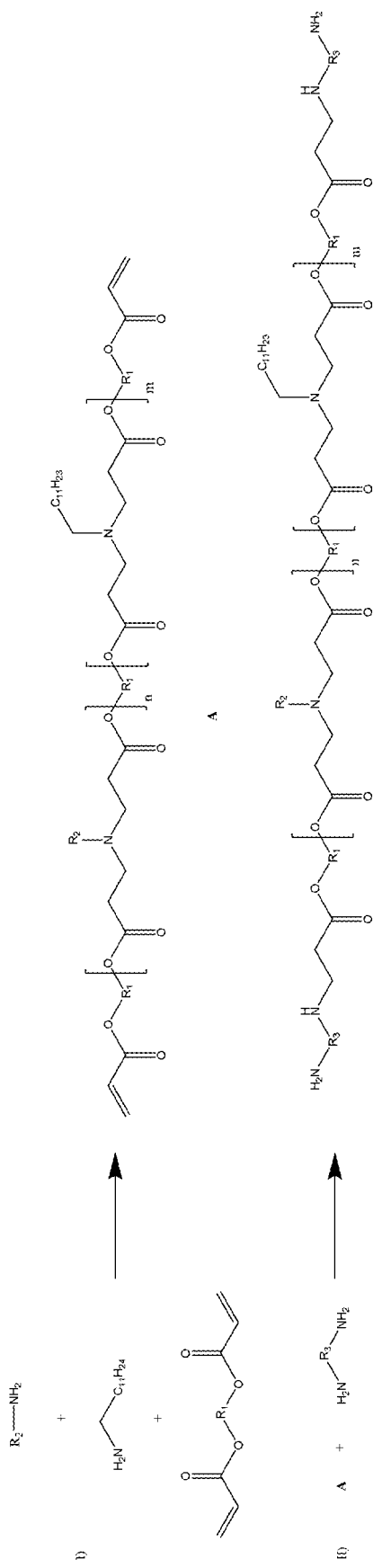
FIG. 1 shows the general synthesis of PBAE polymers.
Figure 2:
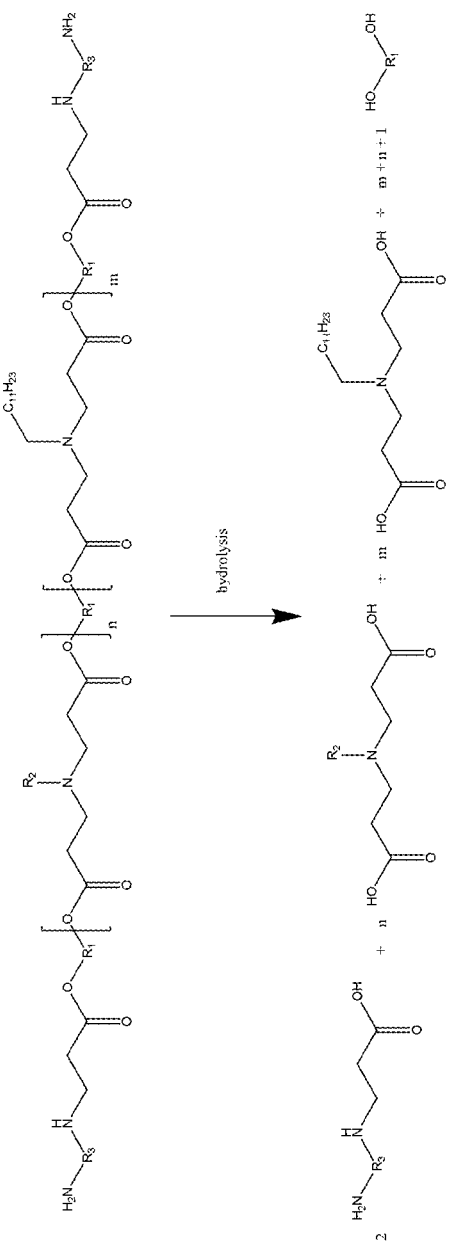
FIG. 2 shows the biodegradation products generated by the hydrolysis of the PBAE polymers.
Figure 3:
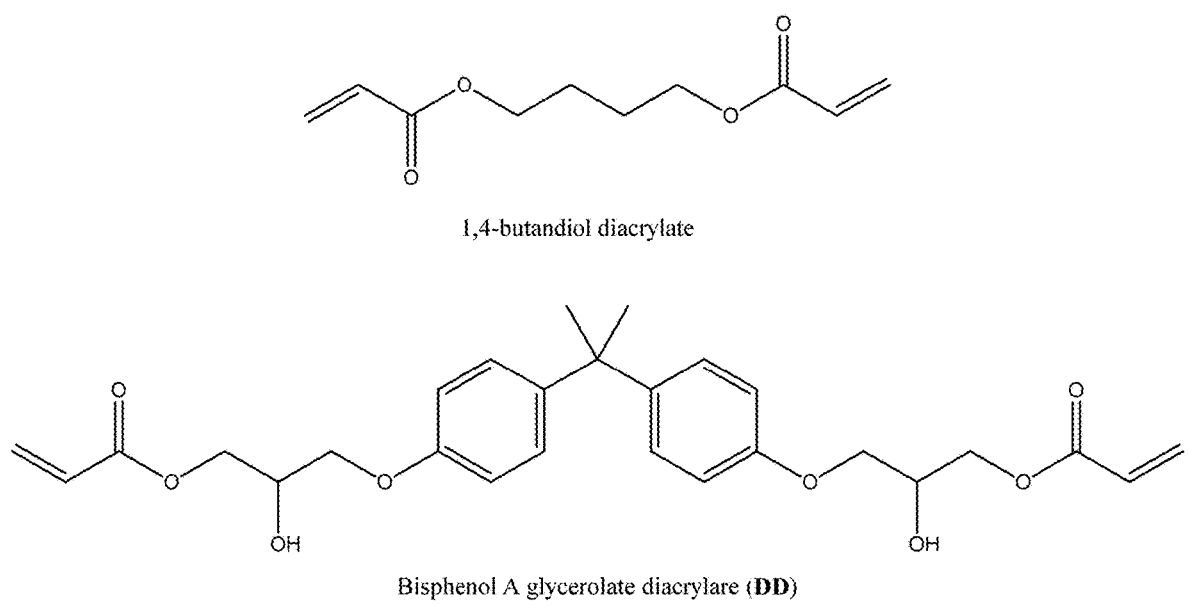
FIG. 3 shows the structure of 1,4-butanediol diacrylate and Bisphenol A glycerolate diacrylate (DD).

For convenience, certain terms employed herein, in the specification, examples, and claims are collected herein.

Unless otherwise required by context, singular terms shall include pluralities, and plural terms shall include the singular.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2%, or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a chemical formula, - - - represents a bond that is absent or a single bond, and ═ or ═ each represent a single or double bond.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The term "aliphatic" includes both saturated and unsaturated, straight chain (i.e., unbranched), branched, acyclic, cyclic, or polycyclic aliphatic hydrocarbons, which are optionally substituted with one or more functional groups. Likewise, the term "heteroaliphatic" refers to heteroalkyl, heteroalkenyl, heteroalkynyl, and heterocyclic groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the disclosure contain 1-100 aliphatic carbon atoms. In certain other embodiments, the alkyl, alkenyl, and alkynyl groups employed in the disclosure contain 1-50 aliphatic carbon atoms. In certain other embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, npropyl, isopropyl, cyclopropyl, —CH$_2$-cyclopropyl, vinyl, allyl, n-butyl, sec-butyl, isobutyl, tertbutyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl, and the like, which again may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group. In some embodiments, an alkyl group has 1 to 1000 carbon atoms ("$C_1$-$C_{1000}$ alkyl"), 1 to 900 carbon atoms ("$C_1$-$C_{900}$ alkyl"), 1 to 800 carbon atoms ("$C_1$-$C_{800}$ alkyl"), 1 to 700 carbon atoms ("$C_1$-$C_{700}$ alkyl"), 1 to 600 carbon atoms ("$C_1$-$C_{600}$ alkyl"), 1 to 500 carbon atoms ("$C_1$-$C_{500}$ alkyl"), 1 to 400 carbon atoms ("$C_1$-$C_{400}$ alkyl"), 1 to 300 carbon atoms ("$C_1$-$C_{300}$ alkyl"), 1 to 200 carbon atoms ("$C_1$-$C_{200}$ alkyl"), 1 to 100 carbon atom ("$C_1$-$C_{100}$ alkyl"). In some embodiments, an alkyl group has 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 1000 carbon atoms ("$C_2$-$C_{1000}$ alkenyl"), 2 to 900 carbon atoms ("$C_2$-$C_{900}$ alkenyl"), 2 to 800 carbon atoms ("$C_2$-$C_{800}$ alkenyl"), 2 to 700 carbon atoms ("$C_2$-$C_{700}$ alkenyl"), 2 to 600 carbon atoms ("$C_2$-$C_{600}$ alkenyl"), 2 to 500 carbon atoms ("$C_2$-$C_{500}$ alkenyl"), 2 to 400 carbon atoms ("$C_2$-$C_{400}$ alkenyl"), 2 to 300 carbon atoms ("$C_2$-$C_{300}$ alkenyl"), 2 to 200 carbon atoms ("$C_2$-$C_{200}$ alkenyl"), 2 to 100 carbon atom ("$C_2$-$C_{100}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In an alkenyl group, a C═C double bond for which the stereochemistry is not specified (e.g.,

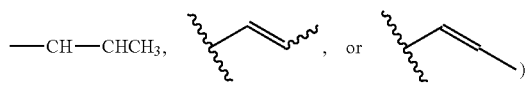

) may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds). In some embodiments, an alkynyl group has 2 to 1000 carbon atoms ("$C_2$-$C_{1000}$ alkynyl"), 2 to 900 carbon atoms ("$C_2$-$C_{900}$ alkynyl"), 2 to 800 carbon atoms ("$C_2$-$C_{800}$ alkynyl"), 2 to 700 carbon atoms ("$C_2$-$C_{700}$ alkynyl"), 2 to 600 carbon atoms ("$C_2$-$C_{600}$ alkynyl"), 2 to 500 carbon atoms ("$C_2$-$C_{500}$ alkynyl"), 2 to 400 carbon atoms ("$C_2$-$C_{400}$ alkynyl"), 2 to 300 carbon atoms ("$C_2$-$C_{300}$ alkynyl"), 2 to 200 carbon atoms ("$C_2$-$C_{200}$ alkynyl"), 2 to 100 carbon atom ("$C_2$-$C_{100}$ alkynyl"). In some embodiments, an alkynyl group has 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, or 4 heteroatoms) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{1000}$ heteroalkyl"), 1 to 900 carbon atoms and 1 or more heteroatoms within the parent chain ("$C_1$-$C_{900}$ heteroalkyl"), 1 to 800 carbon atoms and 1 or more heteroatoms within the parent chain ("$C_1$-$C_{800}$ heteroalkyl"), 1 to 700 carbon atoms and 1 or more heteroatoms within the parent chain ("$C_1$-$C_{700}$ heteroalkyl"), 1 to 600 carbon atoms and 1 or more heteroatoms within the parent chain ("$C_1$-$C_{600}$ heteroalkyl"), 1 to 500 carbon atoms and 1 or more heteroatoms within the parent chain ("$C_1$-$C_{500}$ heteroalkyl"), 1 to 400 carbon atoms and 1 or more heteroatoms within the parent chain ("$C_1$-$C_{400}$ heteroalkyl"), 1 to 300 carbon atoms and 1 or more heteroatoms within the parent chain ("$C_1$-$C_{300}$ heteroalkyl"), 1 to 200 carbon atoms and 1 or more heteroatoms within the parent chain ("$C_1$-$C_{200}$ heteroalkyl"), or 1 to 100 carbon atoms and 1 or more heteroatoms within the parent chain ("$C_1$-$C_{100}$ heteroalkyl"). In certain embodiments, a heteroalkyl group refers to a saturated group having from 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and 1 or more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl"). Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a saturated group having from 1 to 1000 carbon atoms and 1 or more heteroatoms within the parent chain ("heteroC$_1$-C$_{1000}$ alkenyl"), 1 to 900 carbon atoms and 1 or more heteroatoms within the parent chain ("heteroC$_1$-C$_{900}$ alkenyl"), 1 to 800 carbon atoms and 1 or more heteroatoms within the parent chain ("heteroC$_1$-C$_{800}$ alkenyl"), 1 to 700 carbon atoms and 1 or more heteroatoms within the parent chain ("heteroC$_1$-C$_{700}$ alkenyl"), 1 to 600 carbon atoms and 1 or more heteroatoms within the parent chain ("heteroC$_1$-C$_{600}$ alkenyl"), 1 to 500 carbon atoms and 1 or more heteroatoms within the parent chain ("heteroC$_1$-C$_{500}$ alkenyl"), 1 to 400 carbon atoms and 1 or more heteroatoms within the parent chain ("heteroC$_1$-C$_{400}$ alkenyl"), 1 to 300 carbon atoms and 1 or more heteroatoms within the parent chain ("heteroC$_1$-C$_{300}$ alkenyl"), 1 to 200 carbon atoms and 1 or more heteroatoms within the parent chain ("heteroC$_1$-C$_{200}$ alkenyl"), or 1 to 100 carbon atoms and 1 or more heteroatoms within the parent chain ("heteroC$_1$-C$_{100}$ alkenyl"). In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a saturated group having from 1 to 1000 carbon atoms and 1 or more heteroatoms within the parent chain ("heteroC$_1$-C$_{1000}$ alkynyl"), 1 to 900 carbon atoms and 1 or more heteroatoms within the parent chain ("heteroC$_1$-C$_{900}$ alkynyl"), 1 to 800 carbon atoms and 1 or more heteroatoms within the parent chain ("heteroC$_1$-C$_{800}$ alkynyl"), 1 to 700 carbon atoms and 1 or more heteroatoms within the parent chain ("heteroC$_1$-C$_{700}$ alkynyl), 1 to 600 carbon atoms and 1 or more heteroatoms within the parent chain ("heteroC$_1$-C$_{600}$ alkynyl"), 1 to 500 carbon atoms and 1 or more heteroatoms within the parent chain ("heteroC$_1$-C$_{500}$ alkynyl"), 1 to 400 carbon atoms and 1 or more heteroatoms within the parent chain ("heteroC$_1$-C$_{400}$ alkynyl"), 1 to 300 carbon atoms and 1 or more heteroatoms within the parent chain ("heteroC$_1$-C$_{300}$ alkynyl"), 1 to 200 carbon atoms and 1 or more heteroatoms within the parent chain ("heteroC$_1$-C$_{200}$ alkynyl"), or 1 to 100 carbon atoms and 1 or more heteroatoms within the parent chain ("heteroC$_1$-C$_{100}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{5-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^a$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N (C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C (=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O) R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6- chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxy-acetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —NH$_2$.

The term "acyl" refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "polymer" refers to a molecule including two or more (e.g., 3 or more, 4 or more, 5 or more, 10 or more) repeating units which are covalently bound together. In certain embodiments, a polymer comprises 3 or more, 5 or more, 10 or more, 20 or more, 50 or more, 100 or more, 500 or more, 1000 or more, 2000 or more, 3000 or more, 4000 or more, 5000 or more, 6000 or more, 7000 or more, 8000 or more, 9000 or more, or 10000 or more repeating units. In certain embodiments, a polymer comprises more than 5000 repeating units. The repeating units of a polymer are referred to as "monomers." A "homopolymer" is a polymer that consists of a single repeating monomer. A "copolymer" is a polymer that comprises two or more different monomer subunits. Copolymers include, but are not limited to, random, block, alternating, segmented, linear, branched, grafted, and tapered copolymers. A "graft polymer" is a segmented copolymer with a linear backbone of one composite and randomly distributed branches of another composite. The major difference between graft polymers and bottlebrush polymers (or brush-arm polymers) is the grafting density. The targeted graft density for bottlebrush polymers is that in at least one segment of the copolymer is one graft from each backbone monomer unit. A "star polymer" is a polymer that consists of several polymers chains connected at a core atom, core molecule, or core polymer. Polymers may be natural (such as biopolymers like naturally occurring polypeptides), or synthetic (e.g., non-naturally occurring). A polymer may have an overall molecular weight of 500 g/mol or greater, 1 Da or greater, 5 Da or greater, 10 Da or greater, 50 Da or greater, 100 Da or greater, 500 Da or greater, 1000 Da or greater, 2000 Da or greater, 5000 Da or greater, 10000 Da or greater, 20000 Da or greater, or 50000 Da or greater.

The terms "living polymer" and "living polymerization" refer a polymerization where the ability of a growing polymer chain to terminate has been removed. Chain termination and chain transfer reactions are absent, and the rate of the chain initiation is also much larger than the rate of chain propagation.

The term "average molecular weight" may encompass the number average molecular weight ($M_n$), weight average molecular weight ($M_w$), higher average molecular weight ($M_z$ or $M_z+1$), GPC/SEC (gel permeation chromatography/size-exclusion chromatography)-determined average molecular weight ($M_p$), and viscosity average molecular weight ($M_v$).

The terms "number average molecular weight," "number average molar mass," and "$M_n$" are measurements of the molecular mass of a polymer. The number average molecular mass is the ordinary arithmetic mean or average of the molecular masses of the individual polymers. It is determined by measuring the molecular mass of n polymer molecules, summing the masses, and dividing by n. For example, a polymer having 100 repeating units of a monomer with a molecular weight of 100 g/mol would have a number average molecular weight ($M_n$) of 10,000 g/mol [$M_n$=(100)*(100 g/mol)/(1)=10,000 g/mol)]. The number average molecular mass of a polymer can be determined by gel permeation chromatography, viscometry via the Mark-Houwink equation, colligative methods such as vapor pressure osmometry, end-group determination, or $^1$H NMR (nuclear magnetic resonance).

The term "monomer" refers to a molecule that may be covalently joined to other monomers to form a polymer. The process by which the monomers are combined to form a polymer is called polymerization. A macromolecule with a reactive moiety that enables it to act as a monomer is called a macromonomer. Molecules made of a small number of monomer units (up to a few dozen) are called oligomers.

The term "average hydrodynamic diameter" ($D_H$) as used herein refers to the average size of a polymer or particle. The average hydrodynamic diameter may or may not encompass the solvation layers of polymer or particle, and may be determined through a number of methods including dynamic light scattering, electron microscopy (e.g., scanning electron microscopy, transmission electron microscopy), atomic force microscopy, and X-ray diffraction.

The term "average polydispersity" (PDI) as used herein refers to a measure of the distribution of molecular size in a mixture, e.g., as determined by a chromatographic method, such as gel permeation chromatography or size exclusion chromatography, or through dynamic light scattering.

As used herein, the term "polyethylene glycol" or "PEG" refers to an ethylene glycol polymer that contains about 20 to about 2,000,000 linked monomers, typically about 50-1,000 linked monomers, usually about 100-300. Polyethylene glycols include ethylene glycol polymer containing various numbers of linked monomers, e.g., PEG20, PEG30, PEG40, PEG60, PEG80, PEG100, PEG115, PEG200, PEG300, PEG400, PEG500, PEG600, PEG1000, PEG1500, PEG2000, PEG3350, PEG4000, PEG4600, PEG5000, PEG6000, PEG8000, PEG11000, PEG12000, PEG2000000, and any mixtures thereof.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ ($C_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+$ ($C_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the compositions disclosed herein comprise an agent(s), e.g., a first therapeutic agent (e.g., at least one (including, e.g., at least two, at least three). In some embodiments, the compositions (e.g., macromonomers, conjugates, or particles) can further comprise a second therapeutic agent, a targeting moiety, a diagnostic moiety as described herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted into biologically active agents through metabolism or some other mechanism.

An agent (e.g., a therapeutic agent) can include a wide variety of different compounds, including chemical compounds and mixtures of chemical compounds (e.g., small organic or inorganic molecules) such as drug compounds (e.g., compounds approved for human or veterinary use by the U.S. Food and Drug Administration as provided in the Code of Federal Regulations (CFR)); targeting agents; isotopically labeled chemical compounds; carbohydrates; saccharines; monosaccharides; oligosaccharides; polysaccharides; biological macromolecules (e.g., peptides, proteins, and peptide analogs and derivatives); peptidomimetics; antibodies and antigen binding fragments thereof; nucleic acids (e.g., DNA or RNA); nucleotides; nucleosides; oligonucleotides; antisense oligonucleotides; polynucleotides; nucleic acid analogs and derivatives; nucleoproteins; mucoproteins; lipoproteins; synthetic polypeptides or proteins; small molecules linked to proteins; glycoproteins; steroids; lipids; hormones; vitamins; vaccines; immunological agents; an extract made from biological materials such as bacteria, plants, fungi, or animal cells; animal tissues; naturally occurring or synthetic compositions; and any combinations thereof.

In some embodiments, the agent is in the form of a prodrug. The term "prodrug" refer to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the conjugate or particle described herein incorporates one therapeutic agent or prodrug thereof. In some embodiments, the conjugate or particle described herein incorporates more than one therapeutic agents or prodrugs.

In some embodiments, the agent (e.g., a therapeutic agent) is a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents (e.g., a therapeutic agents) in the compositions include, but are not limited to, those found in *Harrison's Principles of Internal Medicine*, 13th Edition, Eds. T. R. Harrison et al. McGraw-Hill N.Y., NY; *Physicians' Desk Reference*, 50th Edition, 1997, Oradell N.J., Medical Economics Co.; *Pharmacological Basis of Therapeutics*, 8th Edition, Goodman and Gilman, 1990; United States Pharmacopeia, The National Formulary, USP XII NF XVII, 1990; current edition of Goodman and Gilman's *The Pharmacological Basis of Therapeutics*; and current edition of *The Merck Index*, the complete contents of all of which are incorporated herein by reference.

Agents, e.g., therapeutic agents, include the herein disclosed categories and specific examples. It is not intended that the category be limited by the specific examples. Those of ordinary skill in the art will recognize also numerous other compounds that fall within the categories and that are useful according to the present disclosure.

Examples of therapeutic agents include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain instances, the diagnostic agent is an imaging agent or contrast agent. The terms "imaging agent" and "contrast agent" refer to a substance used to enhance the contrast of structures or fluids within the body in medical imaging. It is commonly used to enhance the visibility of blood vessels and the gastrointestinal tract in medical imaging.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disorder" refers to a condition that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative disorders include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D.C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, *cannabis* dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

An "effective amount" of a polymer or composition described herein refers to an amount sufficient to elicit the desired biological response. An effective amount of a polymer or composition described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a polymer or composition described herein is an amount sufficient to provide a therapeutic benefit in the treatment of a condition or to delay or minimize one or more symptoms associated with the condition. A therapeutically effective amount of a polymer or composition means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a polymer or composition described herein is an amount sufficient to prevent a condition, or one or more symptoms associated with the condition or prevent its recurrence. A prophylactically effective amount of a polymer or composition means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "nucleic acid" or "nucleic acid sequence", "nucleic acid molecule", "nucleic acid fragment" or "polynucleotide" are used interchangeably. A polynucleotide molecule is a biopolymer composed of nucleotide monomers covalently bonded in a chain. DNA (deoxyribonucleic acid) and RNA (ribonucleic acid) are examples of polynucleotides with distinct biological function. DNA consists of two chains of polynucleotides, with each chain in the form of a helical spiral. RNA is more often found in nature as a single-strand folded onto itself. Exemplary types of RNA include double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA).

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "RNA interference" or "RNAi" refers to a biological process in which RNA molecules inhibit gene expression or translation, by neutralizing targets mRNA molecules. Since the discovery of RNAi and its regulatory potentials, it has become evident that RNAi has immense potential in suppression of desired genes. RNAi is now known as precise, efficient, stable, and better than antisense technology for gene suppression. Two types of small ribonucleic acids molecules are central to RNA interference: miRNA and siRNA. These small RNAs can bind to mRNA molecules and either increase or decrease their activity (e.g., preventing an mRNA from being translated into a protein). The RNAi pathway is found in many eukaryotes, including animals, and is initiated by the enzyme Dicer, which cleaves long dsRNA molecules into short double-stranded fragments of ~20 nucleotide siRNAs. Each siRNA is unwound into two single-stranded RNAs (ssRNAs), the passenger strand and the guide strand. The passenger strand is degraded and the guide strand is incorporated into the RNA-induced silencing complex (RISC). The most well-studied outcome is post-transcriptional gene silencing, which occurs when the guide strand pairs with a complementary sequence in a mRNA molecule and induces cleavage by Argonaute 2 (Ago2), the catalytic component of the RISC complex. In some organisms, this process spreads systematically, despite the initially limited molar concentrations of siRNA.

The term "biodegradable" or "biodegradation" refers to the disintegration of materials by biological means. Organic material can be degraded aerobically or anaerobically. Decomposition of biodegradable substances may include both biological and abiotic steps, such as hydrolysis.

The term "biocompatible" or "biocompatibility" refers to the ability of a material to perform with an appropriate host response in a specific situation. In particular, the terms refer to the ability of a biomaterial to perform its desired function with respect to a medical therapy without eliciting any undesirable local or systematic effects in the recipient or beneficiary of that therapy, but generating the most appropriate beneficial cellular or tissue response in that specific situation, and optimizing the clinically relevant performance of that therapy.

The disclosure is not intended to be limited in any manner by the above exemplary listing of substituents. Additional terms may be defined in other sections of this disclosure.

DETAILED DESCRIPTION OF CERTAIN EMBODIMENTS

Before the disclosed systems, compositions, methods, reagents, and kits are described in more detail, it should be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

Described herein are novel PBAEs derived from polylactone (PCL) diacrylates. In some embodiments, the PBAEs include dipolymers derived from one diacrylate monomers and one amine, terpolymers derived from one diacrylate monomer and two different amines. The PCL-derived PBAEs promote stable formulations with agents such as oligonucleotides, leading to transfection efficacy several times higher than transfection agents such as PEI, for example, and further leading to target organ specificity. The PCL-derived PBAEs are biodegradable and biocompatible, offering higher efficacy and lower toxicity for a variety of applications.

Polymers

In one aspect, provided herein is a polymer of Formula (I):

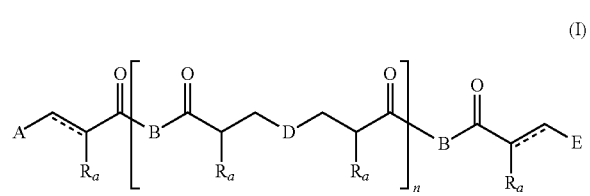

or a pharmaceutically acceptable salt thereof, wherein:

⸺ is a single bond or a double bond;

A is hydrogen or —XR$_3$;

each B independently is a diradical of the formula:

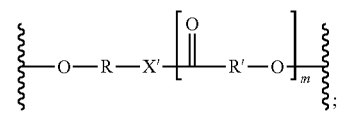

each D independently is:

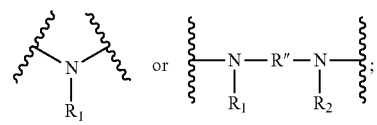

E is hydrogen or —XR$_4$;

each R, R', and R" independently is optionally substituted, cyclic or acyclic aliphatic; optionally substituted, cyclic or acyclic heteroaliphatic; or a combination thereof;

each R$_a$ independently is hydrogen or optionally substituted aliphatic;

R$_1$ and R$_2$ independently are selected from hydrogen; optionally substituted, cyclic or acyclic aliphatic; optionally substituted, cyclic or acyclic heteroaliphatic; optionally substituted aryl; optionally substituted heteroaryl; and a nitrogen protecting group; or R$_1$ and R$_2$ are combined to form a ring;

R$_3$ and R$_4$ independently are selected from hydrogen; optionally substituted, cyclic or acyclic aliphatic; optionally substituted, cyclic or acyclic heteroaliphatic; optionally substituted aryl; optionally substituted heteroaryl; and a protecting group;

X is O, S, NH or NR$_X$, wherein R$_X$ is optionally substituted, cyclic or acyclic aliphatic; optionally substituted, cyclic or acyclic heteroaliphatic; optionally substituted aryl; or optionally substituted heteroaryl;

X' is O or NR$_y$, wherein R$_y$ is hydrogen or optionally substituted aliphatic;

each m independently is an integer between 1 and 100, inclusive; and n is an integer between 1 and 10,000, inclusive.

In certain embodiments, the polymer of Formula (I) is of Formula (II):

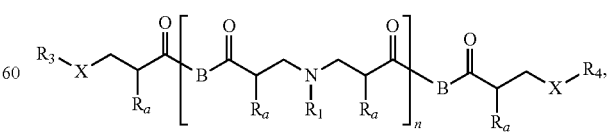

or a pharmaceutically acceptable salt thereof.

In certain embodiments, the polymer of Formula (I) is of Formula (III):

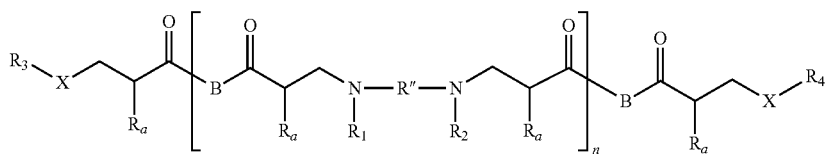

or a pharmaceutically acceptable salt thereof.

In certain embodiments, the polymer of Formula (I) is of Formula (IV):

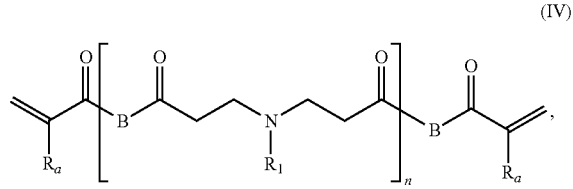

or a pharmaceutically acceptable salt thereof.

In certain embodiments, the polymer of Formula (I) is of Formula (V):

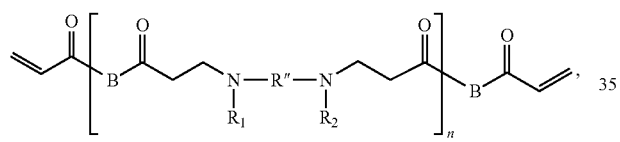

or a pharmaceutically acceptable salt thereof.

Variable A

In certain embodiments, A is hydrogen or —$XR_3$, wherein X and $R_3$ are defined herein. In certain particular embodiments, A is —$NHR_3$. In certain particular embodiments, A is —$NR_xR_3$. In certain particular embodiments, A is hydrogen. In certain particular embodiments, A is —$NH_2$. In certain embodiments, A is

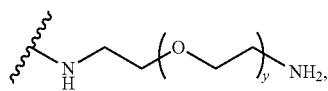

wherein y is 1, 2, 3, 4, 5, 6, 7, 8, 9 or 10. In certain particular embodiments, A is

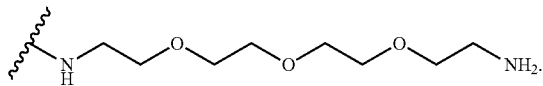

Variable B

In certain embodiments, each B independently is a diradical of the formula:

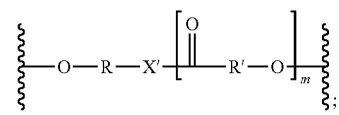

wherein R, R', and m are as defined herein. In certain embodiments, m is 1, 2, 3, 4, 5, 6, 7, 8, 9, or 10. In certain particular embodiments, m is 3. In certain particular embodiments, m is 5. In certain particular embodiments, m is 7.

In certain embodiments, B is of the formula:

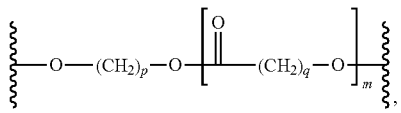

wherein p and q independently are 2, 3, 4, 5 or 6. In certain embodiments, m is 1, 2, 3, 4, 5, 6, 7, 8, 9, or 10. In certain particular embodiments, m is 3. In certain particular embodiments, m is 5. In certain particular embodiments, m is 7.

In certain embodiments, B is of the formula:

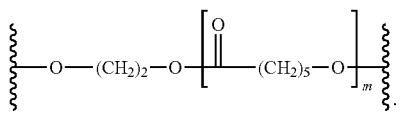

In certain embodiments, m is 1, 2, 3, 4, 5, 6, 7, 8, 9, or 10. In certain particular embodiments, m is 3. In certain particular embodiments, m is 5. In certain particular embodiments, m is 7.

Variable D

In certain embodiments, each D independently is:

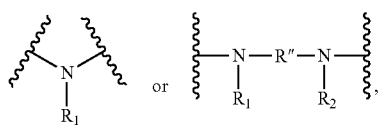

wherein $R_1$ and $R_2$ are defined herein.

When D is

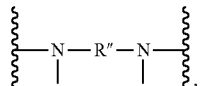

the groups $R_1$ and/or $R_2$ may be covalently bonded to R" to form one or two cyclic structures. In certain embodiments, $R_1$ and $R_2$ are combined to form a ring.

In certain embodiments, each D is
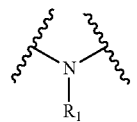
and independently is selected from Table 1.
TABLE 1
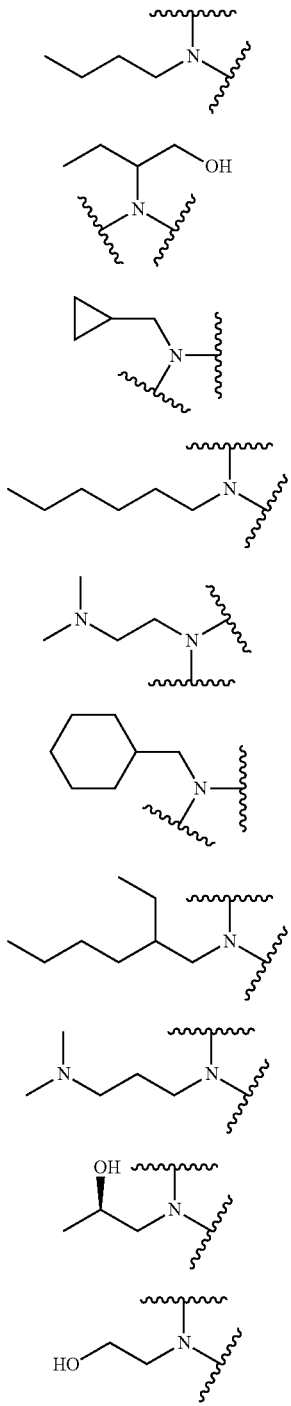
TABLE 1-continued
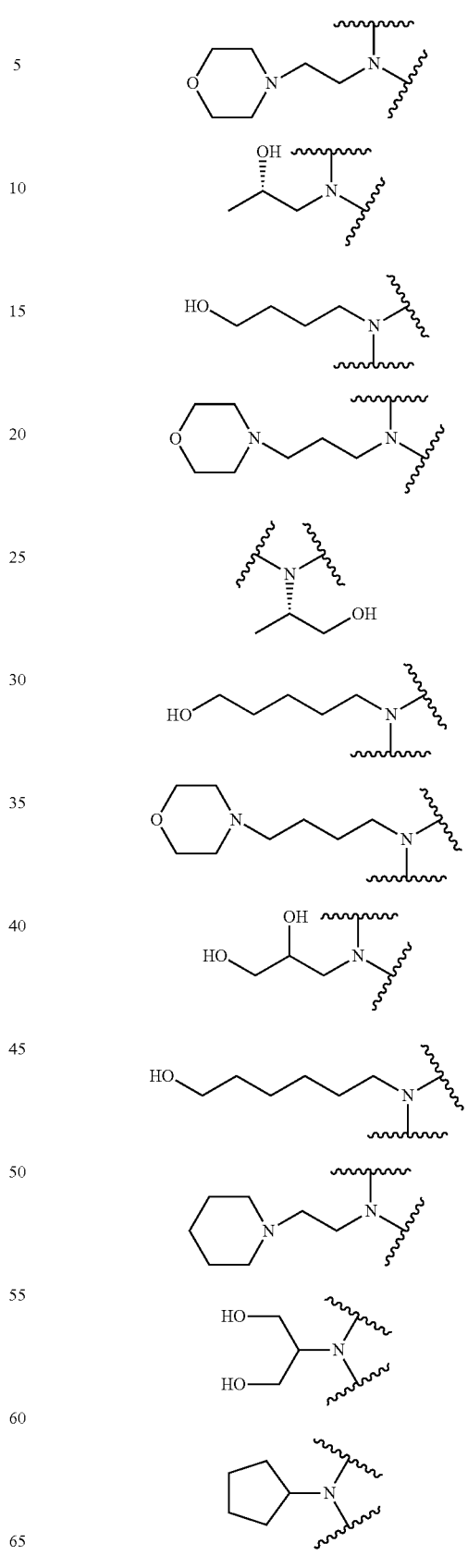

TABLE 1-continued
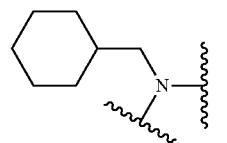 [SMILES: *N(*)CC1CCCCC1]
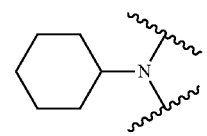 [SMILES: *N(*)C1CCCCC1]
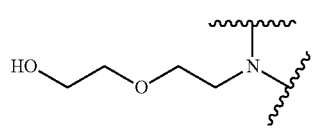 [SMILES: *N(*)CCOCCO]
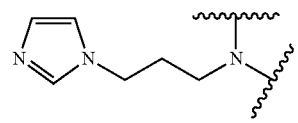 [SMILES: *N(*)CCCn1ccnc1]
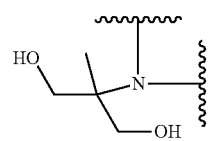 [SMILES: *N(*)C(C)(CO)CO]
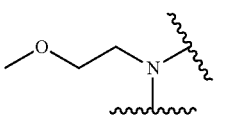 [SMILES: *N(*)CCOC]
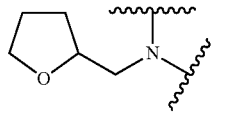
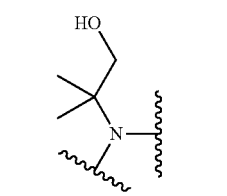 [SMILES: *N(*)C(C)(C)CO]
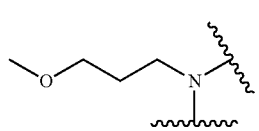 [SMILES: *N(*)CCCOC]
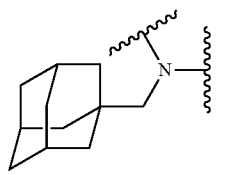 [SMILES: *N(*)CC12CC3CC(CC(C3)C1)C2]
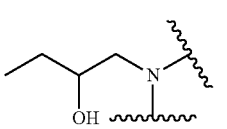 [SMILES: *N(*)CC(O)CC]
TABLE 1-continued
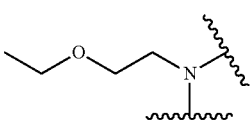 [SMILES: *N(*)CCOCC]
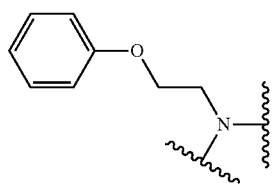
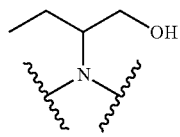
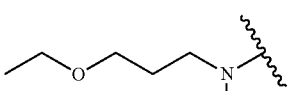
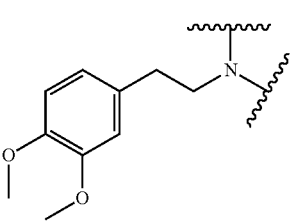 [SMILES: *N(*)CCc1ccc(OC)c(OC)c1]
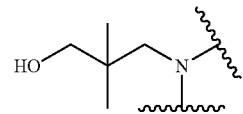
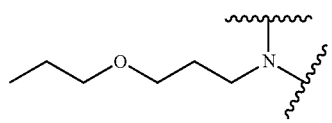 [SMILES: *N(*)CCCOCCC]
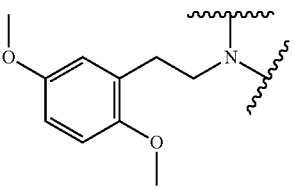 [SMILES: *N(*)CCc1cc(OC)ccc1OC]
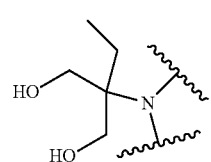

TABLE 1-continued
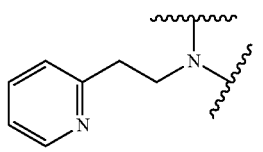 [SMILES: *N(*)CCc1ccccn1]
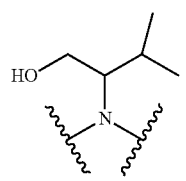 [SMILES: *N(*)C(CO)C(C)C]
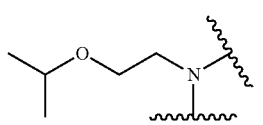 [SMILES: *N(*)CCOC(C)C]
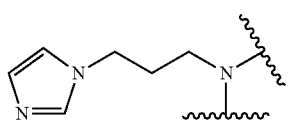 [SMILES: *N(*)CCCn1ccnc1]
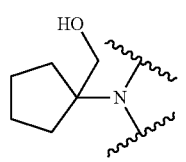 [SMILES: *N(*)C1(CO)CCCC1]
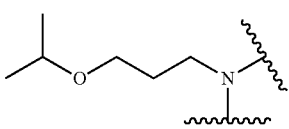 [SMILES: *N(*)CCCOC(C)C]
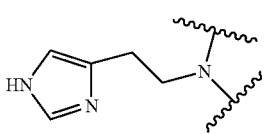 [SMILES: *N(*)CCc1c[nH]cn1]
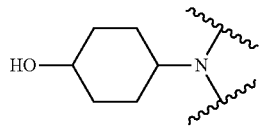 [SMILES: *N(*)C1CCC(O)CC1]
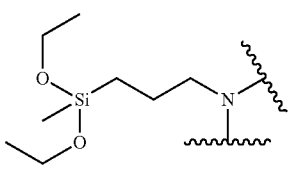 [SMILES: *N(*)CCC[Si](C)(OCC)OCC]
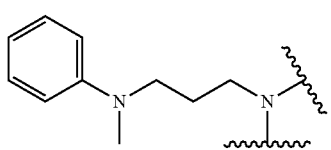 [SMILES: *N(*)CCCN(C)c1ccccc1]
TABLE 1-continued
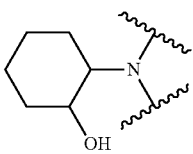 [SMILES: *N(*)C1CCCCC1O]
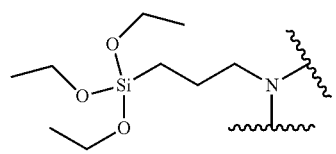 [SMILES: *N(*)CCC[Si](OCC)(OCC)OCC]
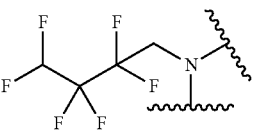 [SMILES: *N(*)CC(F)(F)C(F)(F)C(F)F]
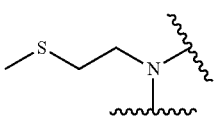 [SMILES: *N(*)CCSC]
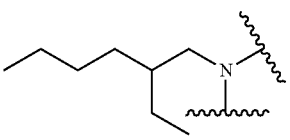 [SMILES: *N(*)CC(CC)CCCC]
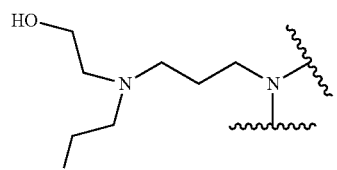
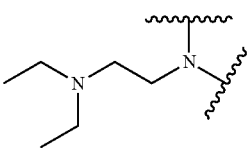 [SMILES: *N(*)CCN(CC)CC]
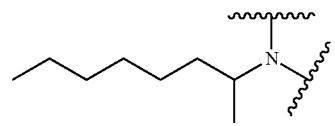 [SMILES: *N(*)C(C)CCCCCC]
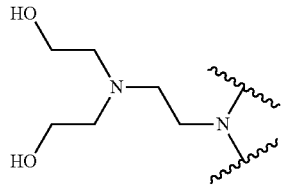 [SMILES: *N(*)CCN(CCO)CCO]

TABLE 1-continued
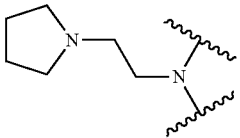 [SMILES: *N(*)CCN1CCCC1]
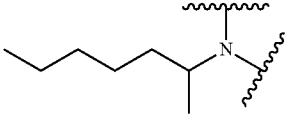 [SMILES: *N(*)C(C)CCCCC]
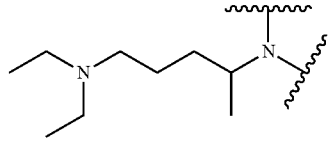 [SMILES: *N(*)C(C)CCCN(CC)CC]
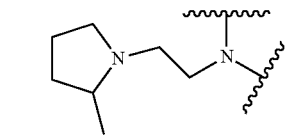 [SMILES: *N(*)CCN1CCCC1C]
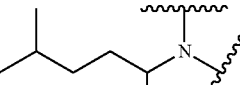
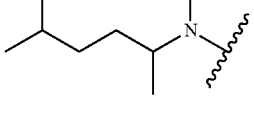
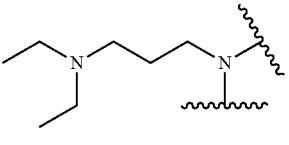 [SMILES: *N(*)CCCN(CC)CC]
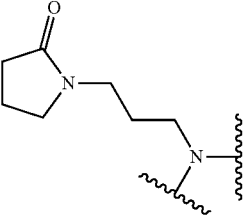 [SMILES: *N(*)CCCN1CCCC1=O]
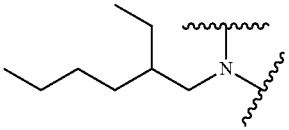 [SMILES: *N(*)CC(CC)CCCC]
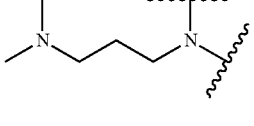
TABLE 1-continued
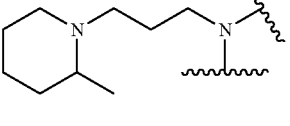
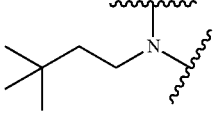 [SMILES: *N(*)CCC(C)(C)C]
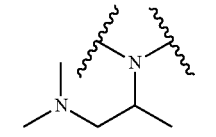 [SMILES: *N(*)C(C)CN(C)C]
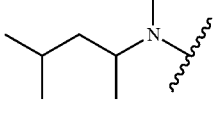
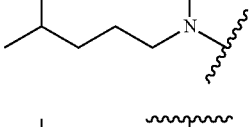
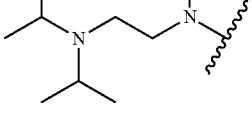
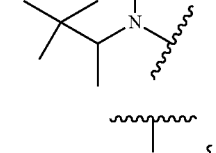
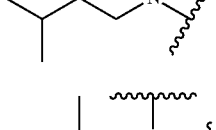
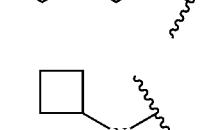
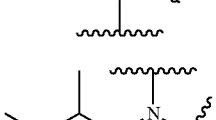
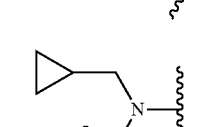
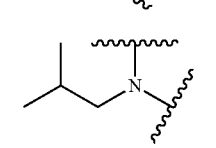

TABLE 1-continued
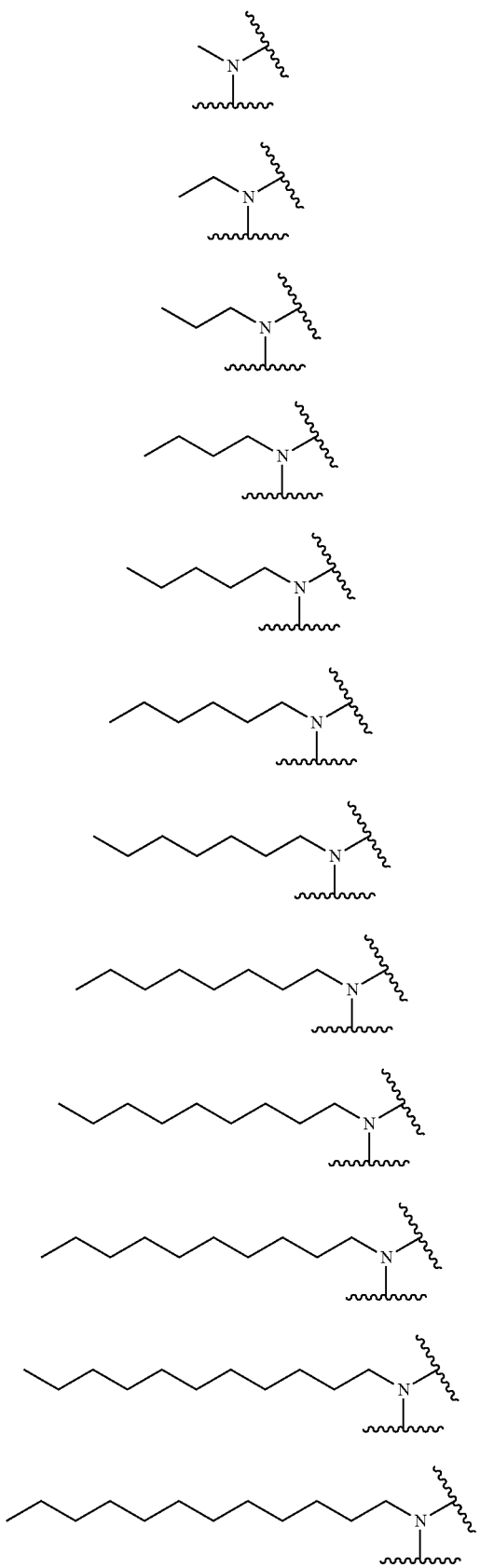
TABLE 1-continued
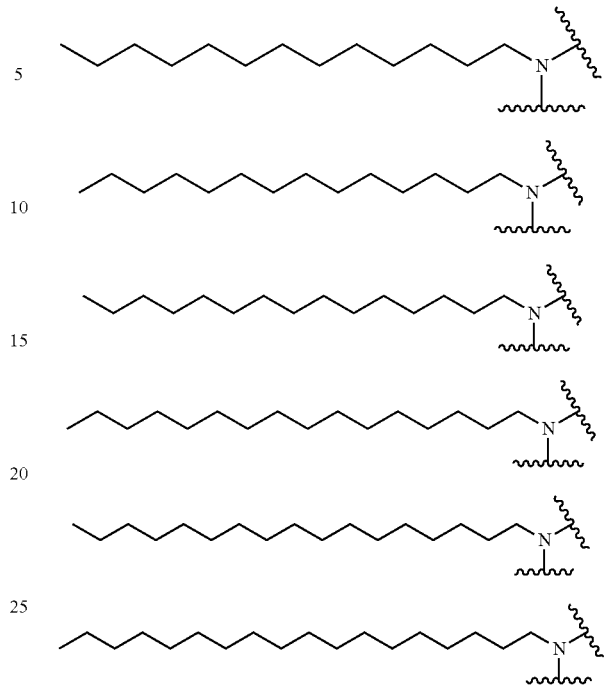
In certain particular embodiments, at least one D diradical is of the formula:
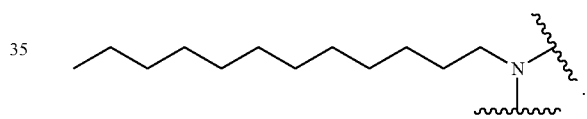
In certain embodiments, each D is
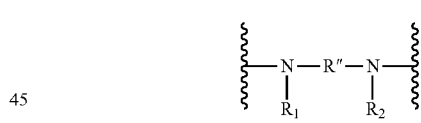
and independently is selected from Table 2.
TABLE 2
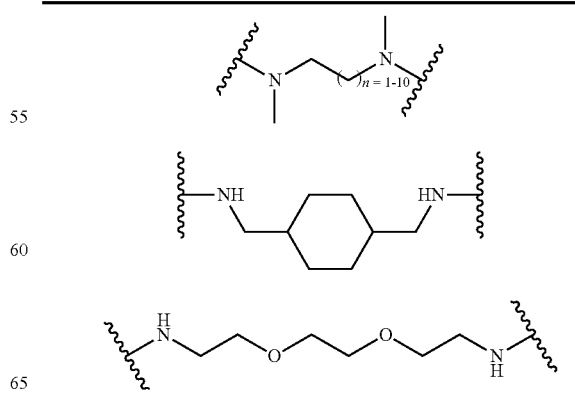

TABLE 2-continued

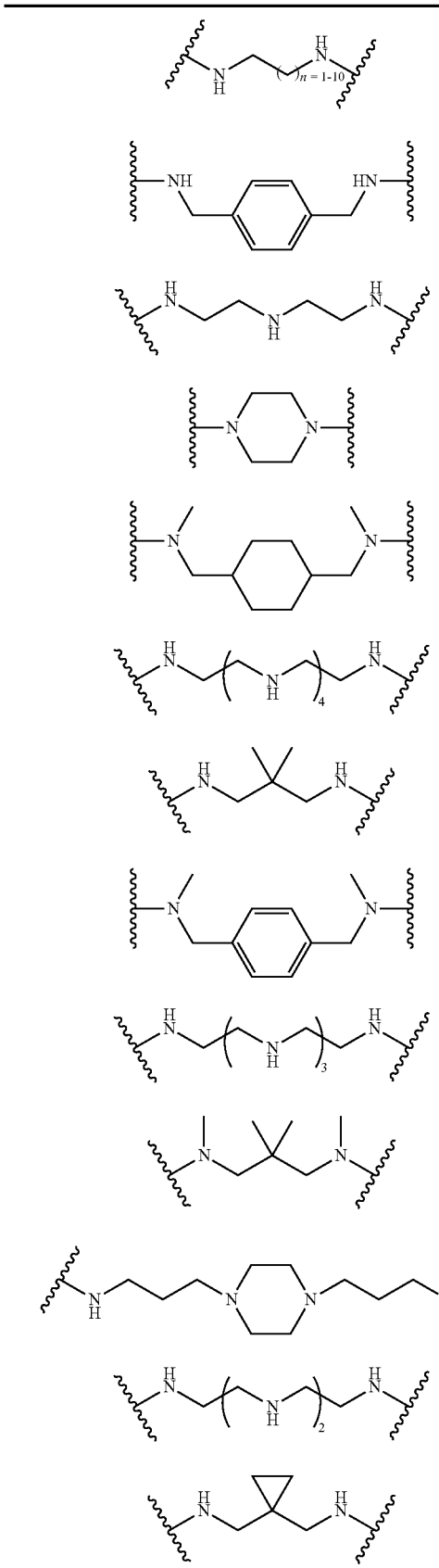

TABLE 2-continued

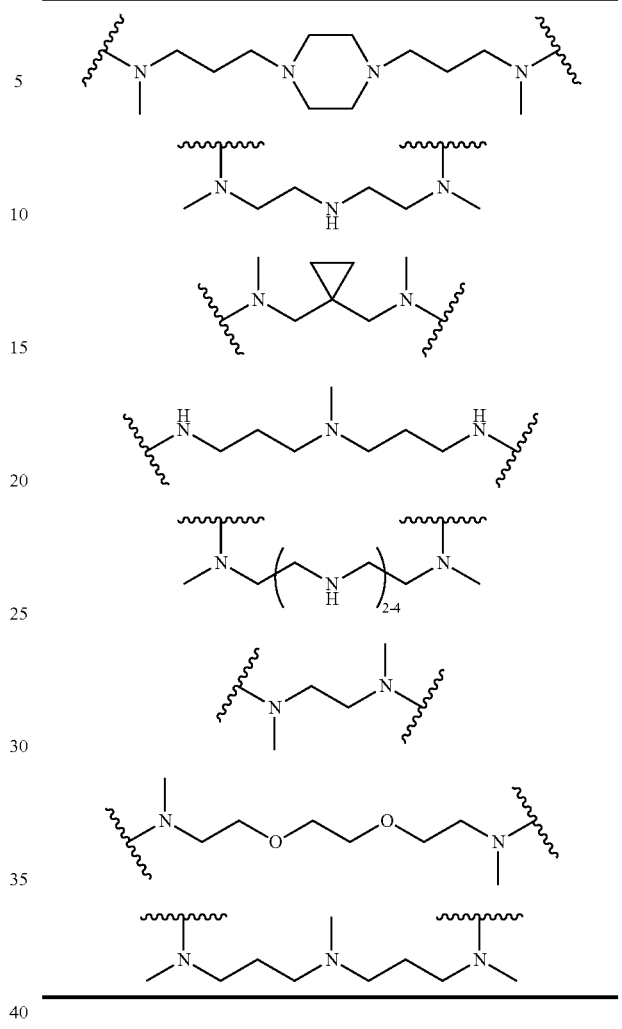

In certain particular embodiments, at least one D diradical is

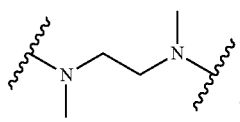 [SMILES: *N(C)CCN(*)C]

In certain embodiments, each D diradical independently is

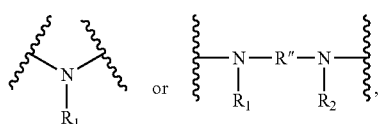

and is selected from the moieties in Table 1 and Table 2.

In certain embodiments, the polymer comprises only one type of D diradical. In certain embodiments, the polymer comprises at least two types of D diradical. In certain embodiments, the polymer comprises only two types of D diradical. In certain embodiments, the polymer comprises at least three types of D diradical. In certain embodiments, the polymer comprises only three types of D diradical. In certain embodiments, the polymer comprises at least four types of D diradical. In certain embodiments, the polymer comprises only four types of D diradical.

Variable E

In certain embodiments, E is hydrogen or —XR$_4$, wherein X and R$_4$ are defined herein. In certain particular embodiments, E is —XR$_4$. In certain particular embodiments, E is hydrogen. In certain particular embodiments, E is —NH$_2$. In certain embodiments, E is

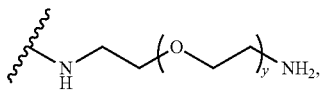

wherein y is 1, 2, 3, 4, 5, 6, 7, 8, 9 or 10. In certain particular embodiments, E is

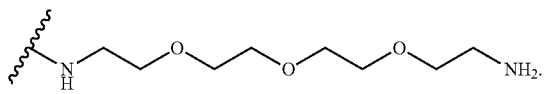 [SMILES: *NCCOCCOCCOCCN]

Variable R

R is divalent (i.e., a diradical). In certain embodiments, each R independently is optionally substituted, cyclic or acyclic aliphatic, optionally substituted, cyclic or acyclic heteroaliphatic, or a combination thereof. In certain embodiments, each R independently is substituted acyclic aliphatic. In certain embodiments, each R independently is unsubstituted acyclic aliphatic. In certain embodiments, each R independently is substituted cyclic aliphatic. In certain embodiments, each R independently is unsubstituted cyclic aliphatic. In certain embodiments, each R independently is substituted acyclic heteroaliphatic. In certain embodiments, each R independently is unsubstituted acyclic heteroaliphatic. In certain embodiments, each R independently is substituted cyclic heteroaliphatic. In certain embodiments, each R independently is unsubstituted cyclic heteroaliphatic.

In certain embodiments, R is of the formula:

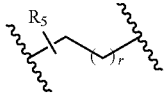

wherein R$_5$ is selected from the group consisting of alkyl, heteroalkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide, wherein said alkyl, heteroalkyl, alkenyl, and alkynyl are optionally substituted, cyclic or acyclic, and branched or linear. In certain embodiments, R$_5$ is optionally substituted C$_2$-C$_{20}$ alkyl or optionally substituted C$_2$-C$_{20}$ heteroalkyl, and r is 1-19.

Variable R'

R' is divalent (i.e., a diradical). In certain embodiments, each R' independently is optionally substituted, cyclic or acyclic aliphatic, optionally substituted, cyclic or acyclic heteroaliphatic, or a combination thereof. In certain embodiments, each R' independently is substituted acyclic aliphatic. In certain embodiments, each R' independently is unsubstituted acyclic aliphatic. In certain embodiments, each R' independently is substituted cyclic aliphatic. In certain embodiments, each R' independently is unsubstituted cyclic aliphatic. In certain embodiments, each R' independently is substituted acyclic heteroaliphatic. In certain embodiments, each R' independently is unsubstituted acyclic heteroaliphatic. In certain embodiments, each R' independently is substituted cyclic heteroaliphatic. In certain embodiments, each R' independently is unsubstituted cyclic heteroaliphatic.

In certain embodiments, R' is of the formula:

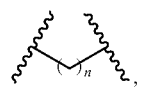

wherein R$_6$ is selected from the group consisting of alkyl, heteroalkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide, wherein said alkyl, heteroalkyl, alkenyl, and alkynyl are optionally substituted, cyclic or acyclic, and branched or linear. In certain embodiments, R$_6$ is optionally substituted C$_2$-C$_{20}$ alkyl or optionally substituted C$_2$-C$_{20}$ heteroalkyl, and r is 1-19.

Variable R"

R" is divalent (i.e., a diradical). In certain embodiments, each R" independently is optionally substituted, cyclic or acyclic aliphatic, optionally substituted, cyclic or acyclic heteroaliphatic, or a combination thereof. In certain embodiments, each R" independently is substituted acyclic aliphatic. In certain embodiments, each R" independently is unsubstituted acyclic aliphatic. In certain embodiments, each R" independently is substituted cyclic aliphatic. In certain embodiments, each R" independently is unsubstituted cyclic aliphatic. In certain embodiments, each R" independently is substituted acyclic heteroaliphatic. In certain embodiments, each R" independently is unsubstituted acyclic heteroaliphatic. In certain embodiments, each R" independently is substituted cyclic heteroaliphatic. In certain embodiments, each R" independently is unsubstituted cyclic heteroaliphatic.

In certain embodiments, each R" independently is

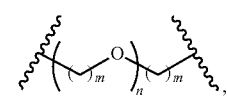

wherein n is an integer between 1 and 20, inclusive. In certain embodiments, each R" independently is wherein n is an integer between 1 and 20, inclusive. In certain embodiments, each R" independently is wherein n is an integer between 1 and 20, inclusive; and each m independently is an integer between 1 and 6, inclusive.

Variable $R_a$

In certain embodiments, each $R_a$ independently is hydrogen or optionally substituted aliphatic. In certain embodiments, each $R_a$ is hydrogen. In certain embodiments, each $R_a$ independently is substituted aliphatic. In certain embodiments, each $R_a$ is independently unsubstituted aliphatic. In certain embodiments, each $R_a$ is independently substituted or unsubstituted $C_{1-6}$ alkyl. In certain embodiments, each $R_a$ is hydrogen or unsubstituted methyl. In certain embodiments, each $R_a$ is unsubstituted methyl.

Variable $R_1$

In certain embodiments, each $R_1$ independently is hydrogen, optionally substituted, cyclic or acyclic aliphatic, optionally substituted, cyclic or acyclic heteroaliphatic, optionally substituted aryl, or optionally substituted heteroaryl, or $R_1$ and $R_2$ are combined to form a ring. In certain embodiments, each $R_1$ independently is hydrogen. In certain embodiments, each $R_1$ independently is substituted acyclic aliphatic. In certain embodiments, each $R_1$ independently is unsubstituted acyclic aliphatic. In certain embodiments, each $R_1$ independently is substituted cyclic aliphatic. In certain embodiments, each $R_1$ independently is unsubstituted cyclic aliphatic. In certain embodiments, each $R_1$ independently is substituted acyclic heteroaliphatic. In certain embodiments, each $R_1$ independently is unsubstituted acyclic heteroaliphatic. In certain embodiments, each $R_1$ independently is substituted cyclic heteroaliphatic. In certain embodiments, each $R_1$ independently is unsubstituted cyclic heteroaliphatic. In certain embodiments, each $R_1$ independently is substituted aryl. In certain embodiments, each $R_1$ independently is unsubstituted aryl. In certain embodiments, each $R_1$ independently is substituted heteroaryl. In certain embodiments, each $R_1$ independently is unsubstituted heteroaryl.

In certain embodiments, at least one $R_1$ is optionally substituted $C_{1-6}$ alkyl. In certain embodiments, each $R_1$ is optionally substituted $C_{1-6}$ alkyl. In certain embodiments, at least one $R_1$ is

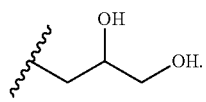 [SMILES: *CC(O)CO]

In certain embodiments, each $R_1$ is

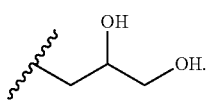 [SMILES: *CC(O)CO]

In certain embodiments, at least one $R_1$ is

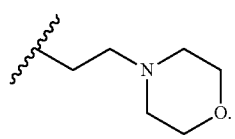 [SMILES: *CCN1CCOCC1]

In certain embodiments, each $R_1$ is

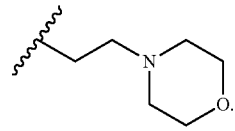 [SMILES: *CCN1CCOCC1]

In certain embodiments, at least one $R_1$ is

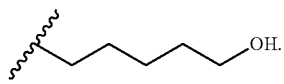 [SMILES: *CCCCCO]

In certain embodiments, each $R_1$ is

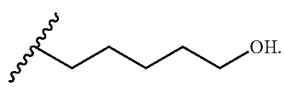 [SMILES: *CCCCCO]

In certain embodiments, at least one $R_1$ is

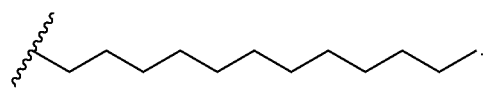 [SMILES: *CCCCCCCCCCCC]

In certain embodiments, each $R_1$ is

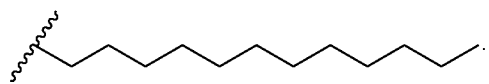 [SMILES: *CCCCCCCCCCCC]

Variable $R_2$

In certain embodiments, each $R_2$ independently is hydrogen, optionally substituted, cyclic or acyclic aliphatic, optionally substituted, cyclic or acyclic heteroaliphatic, optionally substituted aryl, or optionally substituted heteroaryl, or $R_1$ and $R_2$ are combined to form a ring. In certain embodiments, each $R_2$ independently is hydrogen. In certain embodiments, each $R_2$ independently is substituted acyclic aliphatic. In certain embodiments, each $R_2$ independently is unsubstituted acyclic aliphatic. In certain embodiments, each $R_2$ independently is substituted cyclic aliphatic. In certain embodiments, each $R_2$ independently is unsubstituted cyclic aliphatic. In certain embodiments, each $R_2$ independently is substituted acyclic heteroaliphatic. In certain embodiments, each $R_2$ independently is unsubstituted acyclic heteroaliphatic. In certain embodiments, each $R_2$ independently is substituted cyclic heteroaliphatic. In certain embodiments, each $R_2$ independently is unsubstituted cyclic heteroaliphatic. In certain embodiments, each $R_2$ independently is substituted aryl. In certain embodiments, each $R_2$ independently is unsubstituted aryl. In certain embodiments, each $R_2$ independently is substituted heteroaryl. In certain embodiments, each $R_2$ independently is unsubstituted heteroaryl. In certain embodiments, at least one $R_2$ is $C_{1-6}$ alkyl. In certain embodiments, each $R_2$ is $C_{1-6}$ alkyl. In certain embodiments, $R_1$ and $R_2$ are combined to form a 4-, 5-, 6-, or 7-membered optionally substituted, saturated or partially-unsaturated ring.

Variables $R_3$ and $R_4$

In certain embodiments, $R_3$ and $R_4$ independently, for each occurrence, are hydrogen, optionally substituted, cyclic or acyclic aliphatic, optionally substituted, cyclic or acyclic heteroaliphatic, optionally substituted aryl, or optionally substituted heteroaryl. In certain embodiments, $R_3$ and $R_4$ independently, for each occurrence, are hydrogen. In certain embodiments, $R_3$ and $R_4$ independently, for each occurrence, are substituted acyclic aliphatic. In certain embodiments, $R_3$ and $R_4$ independently, for each occurrence, are unsubstituted acyclic aliphatic. In certain embodiments, $R_3$ and $R_4$ independently, for each occurrence, are substituted cyclic aliphatic. In certain embodiments, $R_3$ and $R_4$ independently, for each occurrence, are unsubstituted cyclic aliphatic. In certain embodiments, $R_3$ and $R_4$ independently, for each occurrence, are substituted acyclic heteroaliphatic. In certain embodiments, $R_3$ and $R_4$ independently, for each occurrence, are unsubstituted acyclic heteroaliphatic. In certain embodiments, $R_3$ and $R_4$ independently, for each occurrence, are substituted cyclic heteroaliphatic. In certain embodiments, $R_3$ and $R_4$ independently, for each occurrence, are unsubstituted cyclic heteroaliphatic. In certain embodiments, $R_3$ and $R_4$ independently, for each occurrence, are substituted aryl. In certain embodiments, $R_3$ and $R_4$ independently, for each occurrence, are unsubstituted aryl. In certain embodiments, $R_3$ and $R_4$ independently, for each occurrence, are substituted heteroaryl. In certain embodiments, $R_3$ and $R_4$ independently, for each occurrence, are unsubstituted heteroaryl.

In certain embodiments, $R^3$ and $R^4$ are the same. In certain embodiments, $R^3$ and $R^4$ are different. In certain embodiments, $R^3$ and $R^4$ are different from $R_1$. In certain embodiments, $R_3$ and $R_4$ independently are optionally substituted, cyclic or acyclic aliphatic, or optionally substituted, cyclic or acyclic heteroaliphatic. In certain embodiments, $R_3$ and $R_4$ independently are:

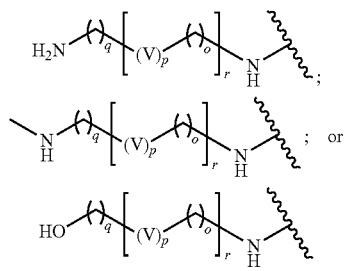

wherein: o, p, q, and r are each independently an integer between 0 and 20, inclusive; each instance of V is independently —O—, —S—, —NH—, —NR$_V$—, or C(R$_V$)$_2$, wherein each instance of $R_V$ is independently hydrogen, halogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, alkylthioxy, or acyl. In certain embodiments, $R_3$ and $R_4$ independently are

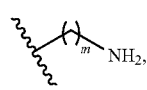

wherein m is an integer between 1 and 20, inclusive. In certain embodiments, $R_3$ and $R_4$ independently are

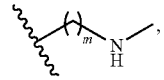

wherein m is an integer between 1 and 20, inclusive. In certain embodiments, $R_3$ and $R_4$ independently are

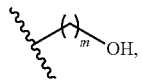

wherein m is an integer between 1 and 20, inclusive. In certain embodiments, $R_3$ and $R_4$ independently are

wherein m is an integer between 1 and 20, inclusive. In certain embodiments, $R_3$ and $R_4$ independently are

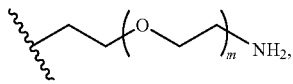

wherein m is an integer between 1 and 20, inclusive. In certain embodiments, $R_3$ and $R_4$ independently are

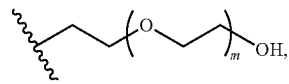

wherein m is an integer between 1 and 20, inclusive. In certain embodiments, $R_3$ and $R_4$ independently are

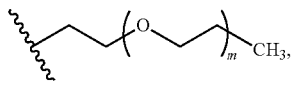

wherein m is an integer between 1 and 20, inclusive.

In certain embodiments, $R^3$ and $R^4$ independently are selected from the group consisting of:

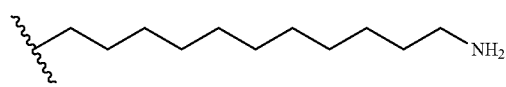
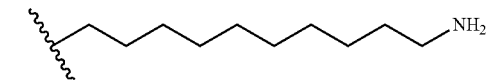
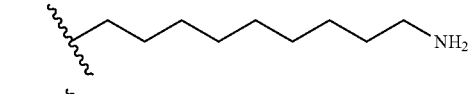
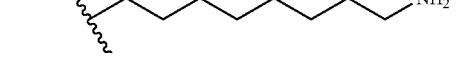

61
-continued
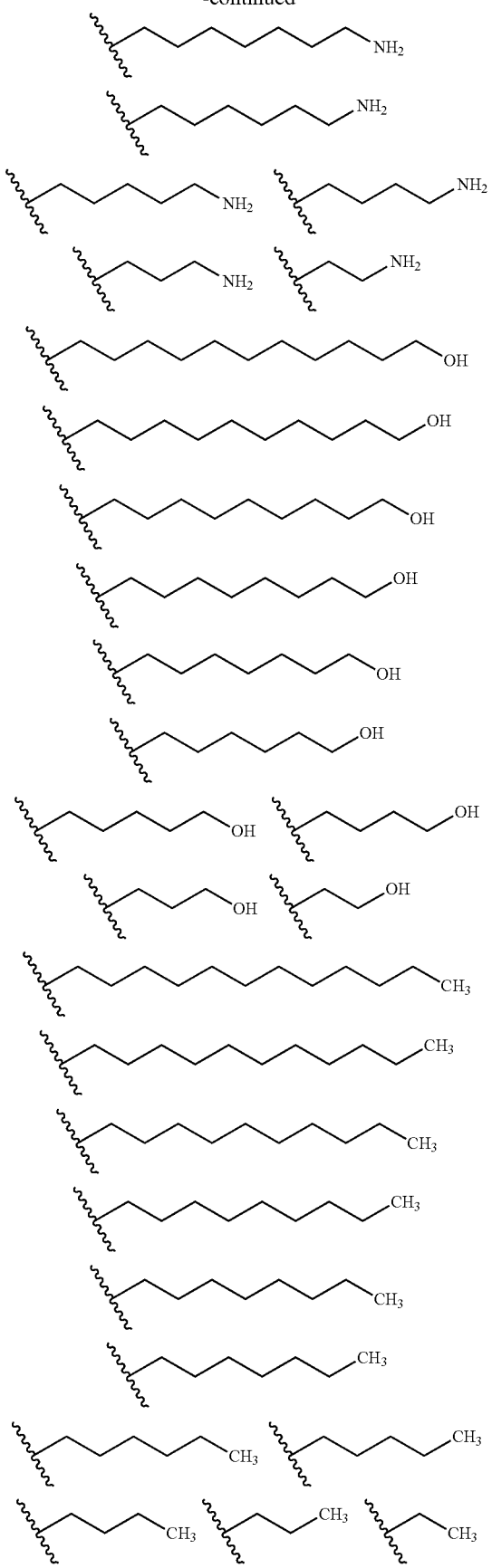
62
-continued
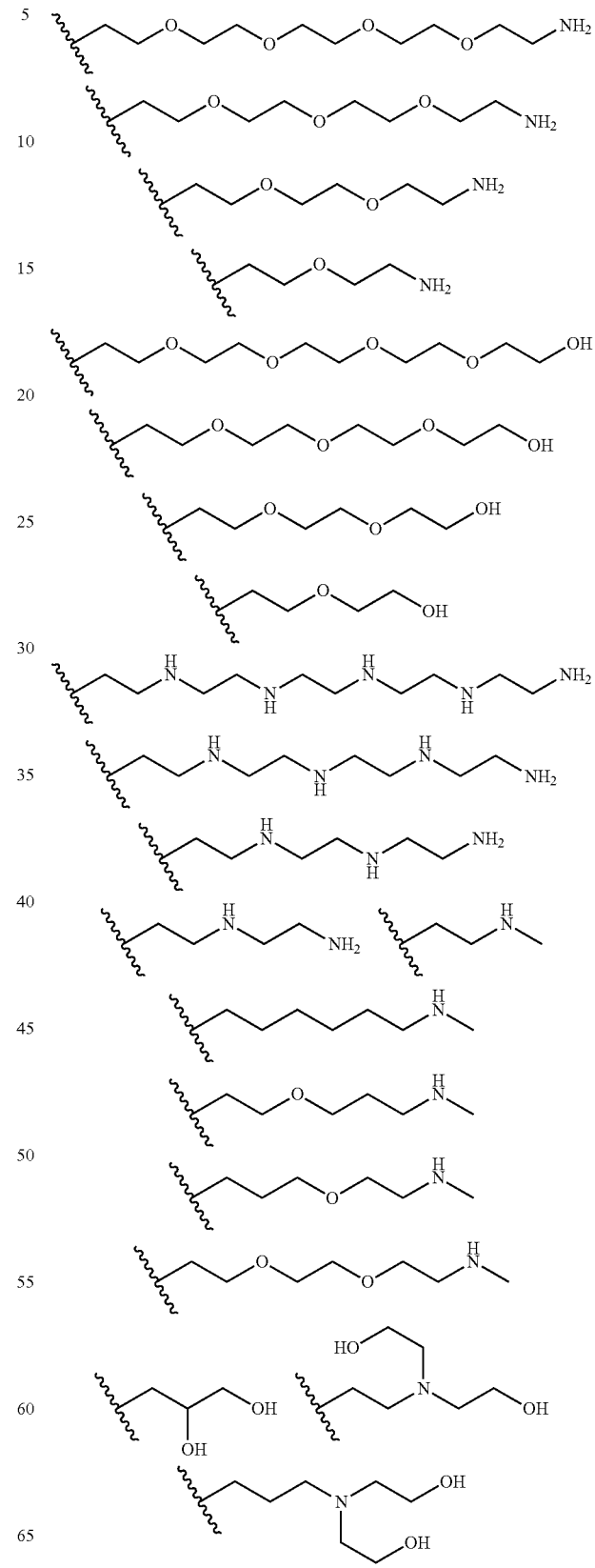

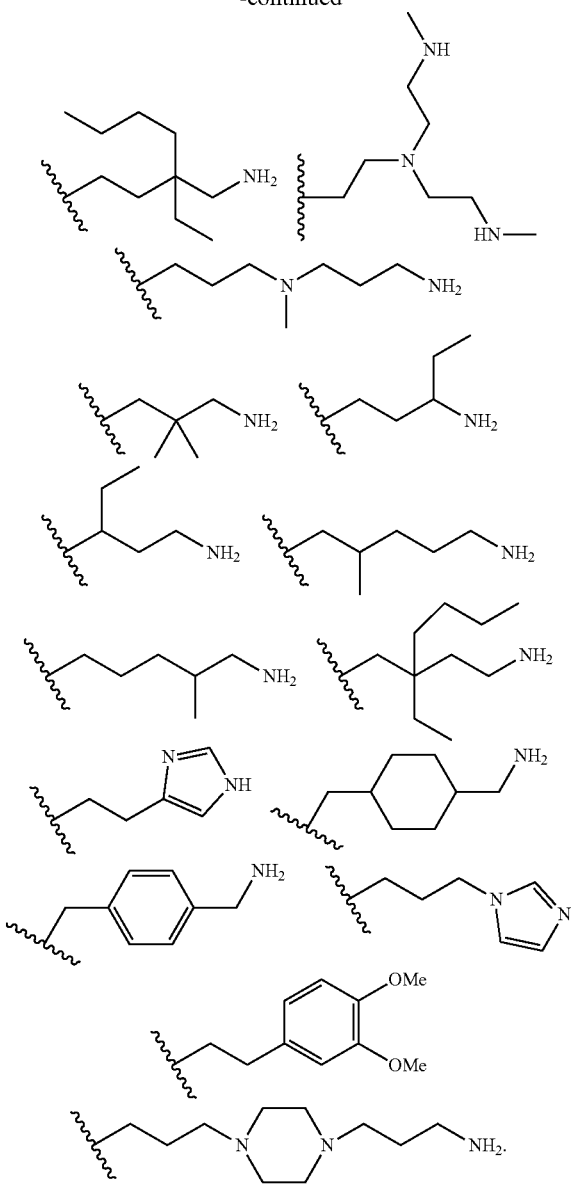

In certain embodiments, R₃ and R₄ are both

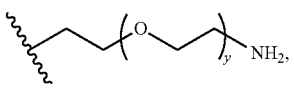

wherein y is 1, 2, 3, 4, 5, 6, 7, 8, 9 or 10.

In certain embodiments, R₃ and R₄ are both

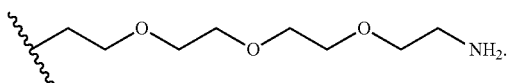 [SMILES: *CCOCCOCCOCCN]

Variable X

In certain embodiments, each X independently is O, S, NH, or $NR_X$, wherein $R_X$ is optionally substituted, aliphatic; optionally substituted carbocyclyl; optionally substituted heteroaliphatic; optionally substituted hetercyclyl; optionally substituted aryl; or optionally substituted heteroaryl. The compositions and polymers provided herein, each X may be the different, or both X may be the same. In certain embodiments, each X is S. In certain embodiments, each X is NH. In certain embodiments, each X is $NR_x$. In certain embodiments, each $R_x$ independently is substituted acyclic aliphatic. In certain embodiments, each $R_x$ independently is unsubstituted acyclic aliphatic. In certain embodiments, each $R_x$ independently is substituted cyclic aliphatic. In certain embodiments, each $R_x$ independently is unsubstituted cyclic aliphatic. In certain embodiments, each $R_x$ independently is substituted acyclic heteroaliphatic. In certain embodiments, each $R_x$ independently is unsubstituted acyclic heteroaliphatic. In certain embodiments, each $R_x$ independently is substituted cyclic heteroaliphatic. In certain embodiments, each $R_x$ independently is unsubstituted cyclic heteroaliphatic. In certain embodiments, each $R_x$ independently is $C_{1-6}$ alkyl.

Variable X'

In certain embodiments, each X' independently is O or $NR_y$, wherein $R_y$ is hydrogen; optionally substituted, aliphatic; optionally substituted carbocyclyl; optionally substituted heteroaliphatic; optionally substituted hetercyclyl; optionally substituted aryl; or optionally substituted heteroaryl. In certain embodiments, each X' is the same. In certain embodiments, X' is O. In certain embodiments, X' is $NR_y$. In certain embodiments, X' is NH. In certain embodiments, each $R_y$ independently is substituted acyclic aliphatic. In certain embodiments, each $R_y$ independently is unsubstituted acyclic aliphatic. In certain embodiments, each $R_y$ independently is substituted cyclic aliphatic. In certain embodiments, each $R_y$ independently is unsubstituted cyclic aliphatic. In certain embodiments, each $R_y$ independently is substituted acyclic heteroaliphatic. In certain embodiments, each $R_y$ independently is unsubstituted acyclic heteroaliphatic. In certain embodiments, each $R_y$ independently is substituted cyclic heteroaliphatic. In certain embodiments, each $R_y$ independently is unsubstituted cyclic heteroaliphatic.

In certain embodiments, each $R_y$ independently is $C_{1-6}$ alkyl.

Variable m

In certain embodiments, each m independently is an integer between 1 and 100, inclusive. In certain embodiments, each m independently is an integer between 1 and 50, inclusive. In certain embodiments, each m independently is an integer between 1 and 20, inclusive. In certain embodiments, each m independently is an integer between 1 and 10, inclusive. In certain embodiments, each m independently is an integer between 2 and 10, inclusive. In certain embodiments, each m independently is an integer between 3 and 10, inclusive. In certain embodiments, each m independently is an integer between 4 and 10, inclusive. In certain embodiments, each m independently is an integer between 5 and 10, inclusive. In certain embodiments, each m independently is an integer between 6 and 10, inclusive. In certain embodiments, each m independently is an integer between 7 and 10, inclusive. In certain embodiments, each m independently is an integer between 8 and 10, inclusive. In certain embodiments, m is 3, 5, or 7.

In certain embodiments, at least 50%, at least 60%, at least 70%, at least 80%, at least 90%, at least 95%, or at least 99% of the polymers have the same value of m.

Variable n

In certain embodiments, n is an integer between 1 and 10,000, inclusive. In certain embodiments, n is an integer between 1,000 and 10,000, inclusive. In certain embodiments, n is an integer between 5,000 and 10,000, inclusive. In certain embodiments, n is an integer between 1 and 1,000, inclusive. In certain embodiments, n is an integer between 10 and 500, inclusive. In certain embodiments, n is an integer between 1 and 100, inclusive. In certain embodiments, n is an integer between 1 and 10, inclusive.

Polymer (1)

In certain embodiments, the polymer is of the formula:

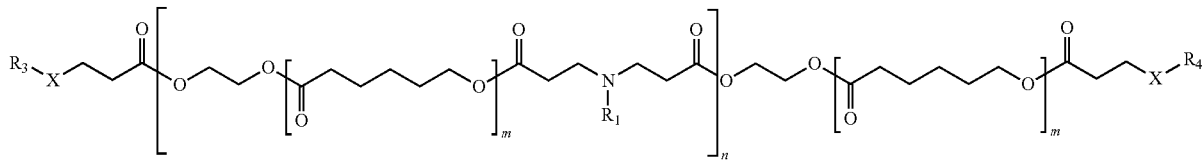

wherein:
each $R_1$ is independently

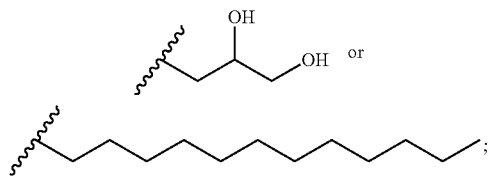

at least one $R_1$ is

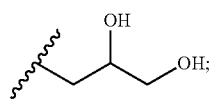

and
at least one $R_1$ is

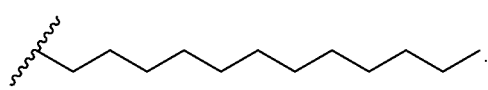 [SMILES: *CCCCCCCCCCCC]

In certain particular embodiments, the ratio of

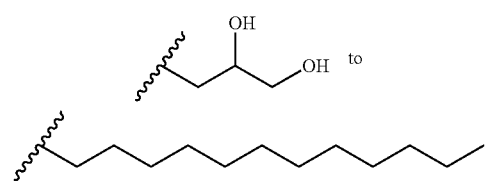

is about 4:2, for example, about 3.9 to about 1.7.

In certain embodiments, each X is as defined herein. In certain particular embodiments, each X is —NH—.

In certain embodiments, $R_3$ and $R_4$ are as defined herein. In certain particular embodiments, $R_3$ and $R_4$ are both

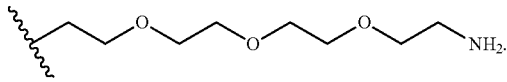 [SMILES: *CCOCCOCCOCCN]

In certain embodiments, m is as defined herein. In certain particular embodiments, m is about 3-4. In certain particular embodiments, m is about 5-6. In certain embodiments, m is about 7-8.

In certain embodiments, n is as defined herein. In certain particular embodiments, n is between 1 and 10, inclusive. In a particular embodiment, n is about 5.

In a particular embodiments, Polymer (1) is of Formula B1: m=3, n is about 5, each X is —NH—, and $R_3$ and $R_4$ are both

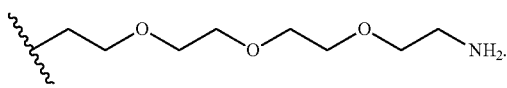 [SMILES: *CCOCCOCCOCCN]

In a particular embodiments, Polymer (1) is of Formula C1: m=5, n is about 5, each X is —NH—, and $R_3$ and $R_4$ are both

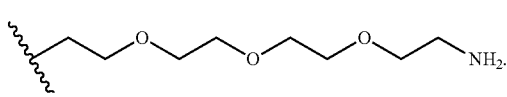 [SMILES: *CCOCCOCCOCCN]

In a particular embodiments, Polymer (1) is of Formula D1: m=7, n is about 5, each X is —NH—, and $R_3$ and $R_4$ are both

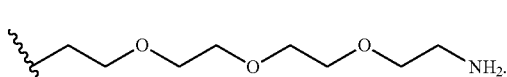

In certain embodiments, Polymer (1) is selected from B1, C1, and D1.

Polymer (2)
In certain embodiments, the polymer is of the formula:

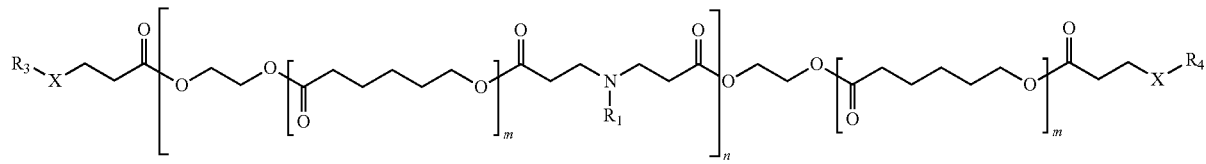

wherein:
each $R_1$ is independently

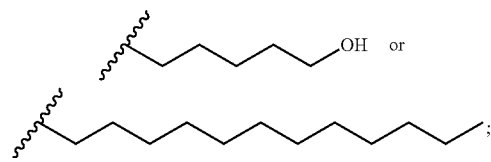

at least one $R_1$ is

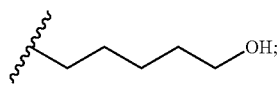 [SMILES: *CCCCCO]

and
at least one $R_1$ is

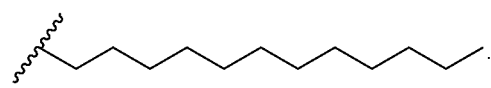 [SMILES: *CCCCCCCCCCCC]

In certain embodiments, the ratio of

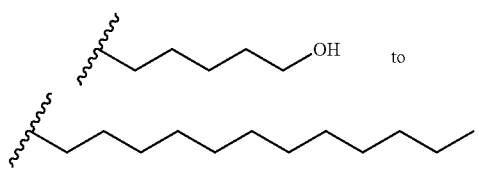

is about 4:2, for example, about 3.9 to about 1.7.

In certain embodiments, each X is as defined herein. In certain particular embodiments, each X is —NH—.

In certain embodiments, $R_3$ and $R_4$ are as defined herein. In certain particular embodiments, $R_3$ and $R_4$ are both

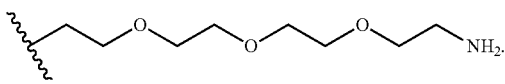 [SMILES: *CCOCCOCCOCCN]

In certain embodiments, m is as defined herein. In certain particular embodiments, m is about 3-4. In certain particular embodiments, m is about 5-6. In certain embodiments, m is about 7-8.

In certain embodiments, n is as defined herein. In certain particular embodiments, n is between 1 and 10, inclusive. In a particular embodiment, n is about 5.

In a particular embodiments, Polymer (2) is of Formula B2: m=3, n is about 5, each X is —NH—, and $R_3$ and $R_4$ are both

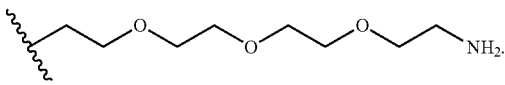 [SMILES: *CCOCCOCCOCCN]

In a particular embodiments, Polymer (2) is of Formula C2: m=5, n is about 5, each X is —NH—, and $R_3$ and $R_4$ are both

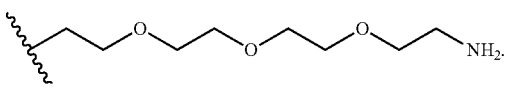 [SMILES: *CCOCCOCCOCCN]

In a particular embodiments, Polymer (2) is of Formula D2: m=7, n is about 5, each X is —NH—, and $R_3$ and $R_4$ are both

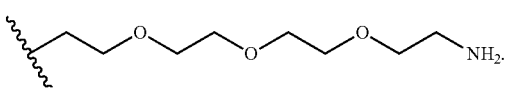 [SMILES: *CCOCCOCCOCCN]

In certain embodiments, Polymer (2) is selected from B2, C2, and D2.

Polymer (3)
In certain embodiments, the polymer is of the formula:

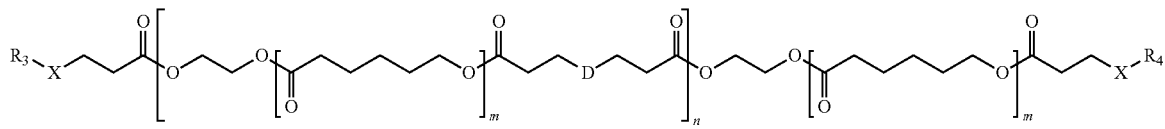

wherein
each D is independently

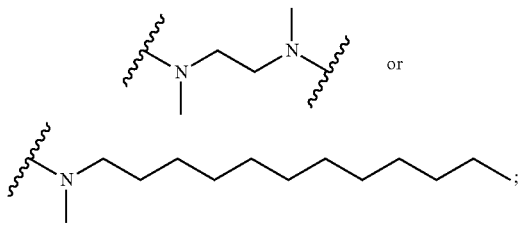 or at least one D is

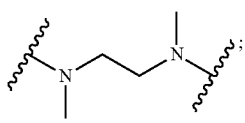 [SMILES: *N(C)CCN(*)C];

and
at least one D is

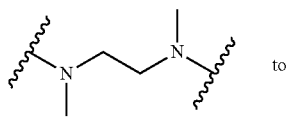.

In certain embodiments, the ratio of

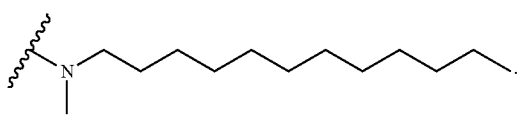 [SMILES: *N(C)CCCCCCCCCCCC] to is about 3.9 to about 1.7.

In certain embodiments, each X is as defined herein. In certain particular embodiments, each X is —NH—.
In certain embodiments, $R_3$ and $R_4$ are as defined herein. In certain particular embodiments, $R_3$ and $R_4$ are both

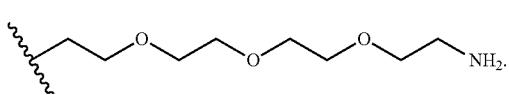 [SMILES: *CCOCCOCCOCCN]

In certain embodiments, m is as defined herein. In certain particular embodiments, m is about 3-4. In certain particular embodiments, m is about 5-6. In certain embodiments, m is about 7-8.

In certain embodiments, n is as defined herein. In certain particular embodiments, n is between 1 and 10, inclusive. In a particular embodiment, n is about 5.

In a particular embodiments, Polymer (3) is of Formula B3: m=3, n is about 5, each X is —NH—, and $R_3$ and $R_4$ are both

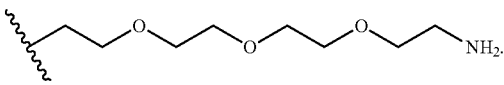 [SMILES: *CCOCCOCCOCCN]

In a particular embodiments, Polymer (3) is of Formula C3: m=5, n is about 5, each X is —NH—, and $R_3$ and $R_4$ are both

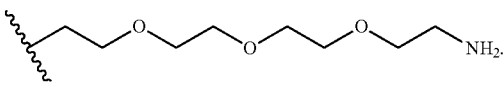 [SMILES: *CCOCCOCCOCCN]

In a particular embodiments, Polymer (3) is of Formula D3: m=7, n is about 5, each X is —NH—, and $R_3$ and $R_4$ are both

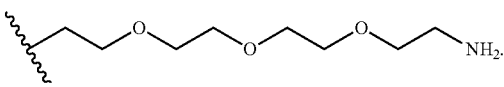 [SMILES: *CCOCCOCCOCCN]

In certain embodiments, Polymer (3) is selected from B3, C3, and D3.

Polymer (4)

In certain embodiments, the polymer is of the formula:

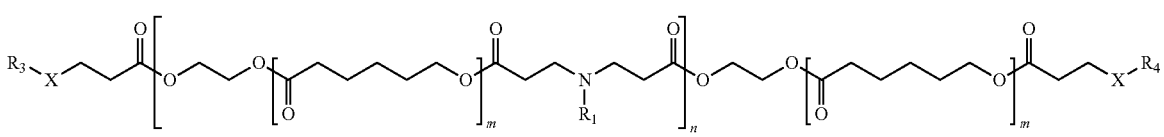

wherein:
each $R_1$ is independently

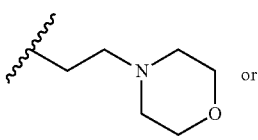 or

-continued

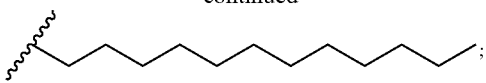

at least one $R_1$ is

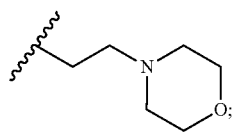 [SMILES: *CCN1CCOCC1]

and
at least one $R_1$ is

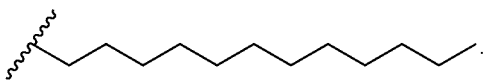 [SMILES: *CCCCCCCCCCCC]

In certain embodiments, the ratio of

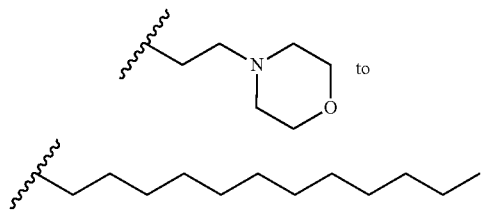

is about 3.9 to about 1.7.

In certain embodiments, each X is as defined herein. In certain particular embodiments, each X is —NH—.

In certain embodiments, $R_3$ and $R_4$ are as defined herein. In certain particular embodiments, $R_3$ and $R_4$ are both

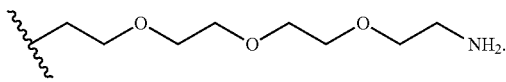 [SMILES: *CCOCCOCCOCCN]

In certain embodiments, m is as defined herein. In certain particular embodiments, m is about 3-4. In certain particular embodiments, m is about 5-6. In certain embodiments, m is about 7-8.

In certain embodiments, n is as defined herein. In certain particular embodiments, n is between 1 and 10, inclusive. In a particular embodiment, n is about 5.

In a particular embodiments, Polymer (4) is of Formula B4: m=3, n is about 5, each X is —NH—, and $R_3$ and $R_4$ are both

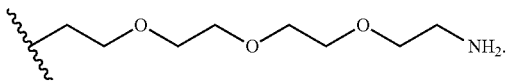

In a particular embodiments, Polymer (4) is of Formula C4: m=5, n is about 5, each X is —NH—, and $R_3$ and $R_4$ are both

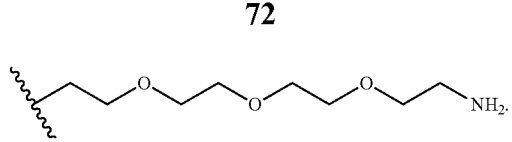

In a particular embodiments, Polymer (4) is of Formula D4: m=7, n is about 5, each X is —NH—, and $R_3$ and $R_4$ are both

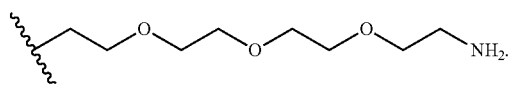 [SMILES: *CCOCCOCCOCCN]

In certain embodiments, Polymer (4) is selected from B4, C4, and D4.

Polymer Properties

Exemplary polymers may be described in terms of properties including, weight average molecular weight ($M_w$), number average molecular weight ($M_n$), average hydrodynamic diameter ($D_H$), and polydispersity ($Đ$).

In certain embodiments, the $M_n$ is determined with viscometry via the (Mark-Houwink equation), colligative methods (such as vapor pressure osmometry), end-group determination, or proton NMR. In certain embodiments, the $M_w$ is determined with gel permeation chromatography, static light scattering, small angle neutron scattering, X-ray scattering, and sedimentation velocity.

In some embodiments, $M_w$ is about 1000 to about 5000 Da, e.g., as determined by gel permeation chromatography. In some embodiments, $M_w$ is about 1000 to about 3000 Da. In some embodiments, $M_W$ is about 1000 to about 2000 Da. In some embodiments, $M_W$ is about 2000 to about 3000 Da. See, e.g., FIG. 9.

In some embodiments, $M_w$ of the polymer is between about 1 kDa and about 100 kDa, e.g., between about about 1 kDa and about 50 kDa, about 15 kDa and about 85 kDa, about 20 kDa and about 60 kDa, or about 30 kDa and about 50 kDa. In one embodiment, the average molecular weight of the polymer is between about 20 kDa and about 60 kDa. In one embodiment, the average molecular weight of the polymer is between about 30 kDa and about 50 kDa.

In some embodiments, the polydispersity ($Đ$) of the polymer is between 1 and 3, inclusive. In some embodiments, the polydispersity ($Đ$) of the polymer is between 2 and 3, inclusive. In some embodiments, the average polydispersity of the polymer is less than bout 2.6 (e.g., less than about 2.5, about 2.4, about 2.3, about 2.2, about 2.1, or less). See, e.g., FIG. 9.

Compounds

Also provided are polylactone derived diacrylate compounds that can be used to make PBAEs of the present disclosure. In one aspect, provided herein is a compound of Formula (VI):

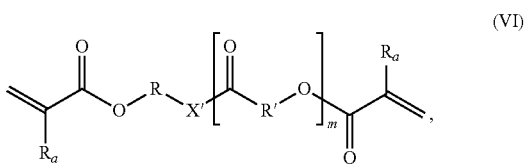

(VI)

wherein:
R is optionally substituted, cyclic or acyclic aliphatic; optionally substituted, cyclic or acyclic heteroaliphatic; or a combination thereof;
each R' independently is optionally substituted, cyclic or acyclic aliphatic; optionally substituted, cyclic or acyclic heteroaliphatic; or a combination thereof;
each $R_a$ independently is hydrogen or optionally substituted aliphatic;
X' is O or $NR_y$, wherein $R_y$ is hydrogen or optionally substituted aliphatic; and
m is an integer between 1 and 100, inclusive.

In certain embodiments, R is a substituted aliphatic. In certain embodiments, R is unsubstituted aliphatic. In certain embodiments, R is substituted heteroaliphatic. In certain embodiments, R is unsubstituted heteroaliphatic.

In certain embodiments, R' is substituted aliphatic. In certain embodiments, R' is unsubstituted aliphatic. In certain embodiments, R' is substituted heteroaliphatic. In certain embodiments, R' is unsubstituted heteroaliphatic.

In certain embodiments, R' is of the formula:

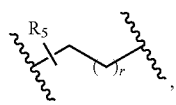

wherein $R_5$ is selected from the group consisting of alkyl, heteroalkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide, wherein said alkyl, heteroalkyl, alkenyl, and alkynyl are optionally substituted, cyclic or acyclic, and branched or linear. In certain embodiments, $R_5$ is optionally substituted $C_2$-$C_{20}$ alkyl or optionally substituted $C_2$-$C_{20}$ heteroalkyl. In certain embodiments, r is 1-19.

In certain embodiments, X' is O. In certain embodiments, X' is $NR_y$. In certain embodiments, X' is NH.

In certain embodiments, m is selected from the group of integers consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In certain embodiments, m is an integer between 31 and 40, inclusive. In certain embodiments, m is an integer between 41 and 50, inclusive. In certain embodiments, m is an integer between 51 and 60, inclusive. In certain embodiments, m is an integer between 61 and 70, inclusive. In certain embodiments, m is an integer between 71 and 80, inclusive. In certain embodiments, m is an integer between 81 and 90, inclusive. In certain embodiments, m is an integer between 91 and 100, inclusive. In certain embodiments, m is 3, 5 or 7.

In certain embodiments, the compound is of the formula:

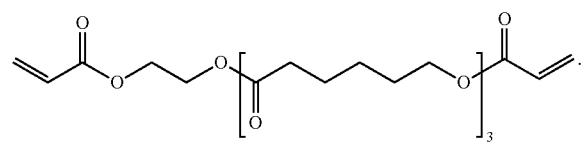

In certain embodiments, the compound is of the formula:

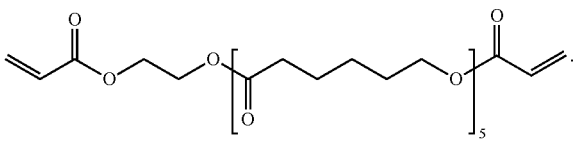

In certain embodiments, the compound is of the formula:

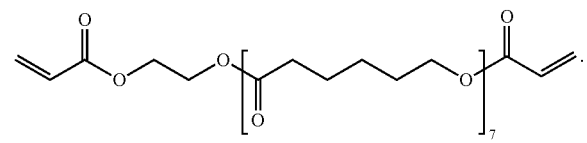

Methods of Preparing Polymers and Compounds

The present disclosure provides methods of preparing PBAE polymers of Formula (II), Formula (III), Formula (IV), and Formula (V), and compounds of Formula (VI).

In one aspect, provided herein is a method of preparing a polymer of Formula (II) as described herein:

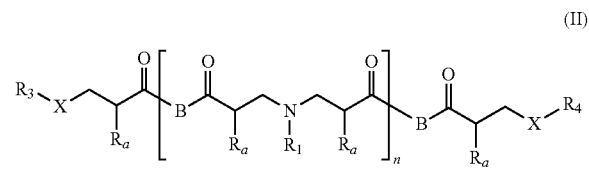
(II)

or a pharmaceutically acceptable salt thereof, comprising reacting a polymer of Formula (IV) as described herein:

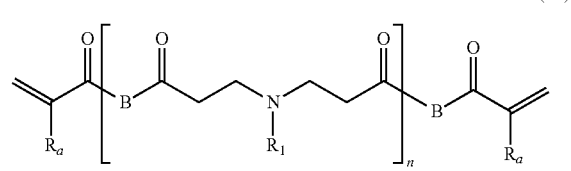
(IV)

or a pharmaceutically acceptable salt thereof, with one or more nucleophiles selected from $R_3XH$ and $R_4XH$, to obtain the polymer of Formula (II).

In another aspect, provided herein is a method of preparing a polymer of Formula (III) as described herein:

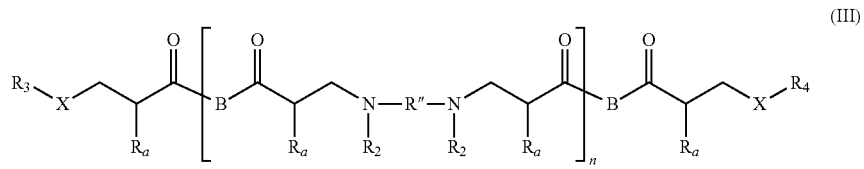
(III)

or a pharmaceutically acceptable salt thereof, comprising reacting a polymer of Formula (V) as described herein:

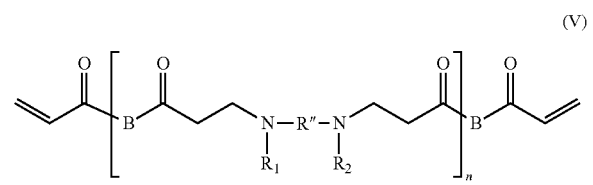
(V)

or a pharmaceutically acceptable salt thereof, with one or more nucleophiles selected from $R_3XH$ and $R_4XH$; to obtain the polymer of Formula (III).

In another aspect, provided herein is a method of preparing a polymer of Formula (IV) as described herein:

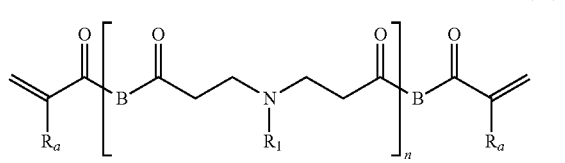
(IV)

or a pharmaceutically acceptable salt thereof, comprising reacting a compound of Formula (VI) as described herein:

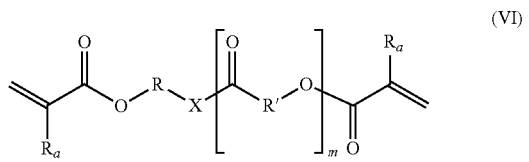
(VI)

with one or more amines of the formula $R_1NH_2$, to obtain the polymer of Formula (IV).

In yet another aspect, provided herein is a method of preparing a polymer of Formula (V) as described herein:

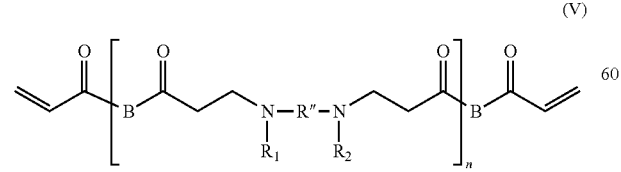
(V)

or a pharmaceutically acceptable salt thereof, comprising reacting a compound of Formula (VI) as described herein:

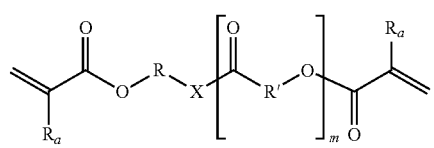
(VI)

with one or more diamines of the formula

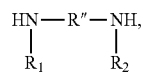

to obtain the polymer of Formula (IV).

In another aspect, provided herein is a method of preparing a compound of Formula (VI) as described herein:

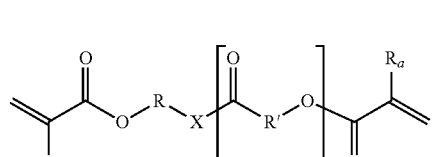
(VI)

comprising:
reacting a compound of Formula (VIa):

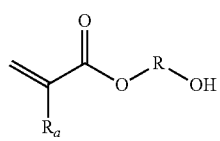
(VIa)

with a lactone to obtain a compound of Formula (VIb):

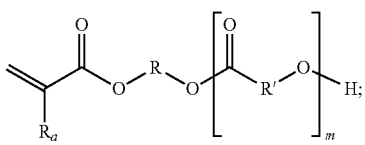
(VIb)

and
acylating the compound of Formula (VIb) to obtain the compound of Formula (VI).

Any lactone may be used in the methods provided above. In certain embodiments, the lactone is of the formula:

wherein R' is defined herein.
In certain embodiments, the lactone is selected from the group consisting of:
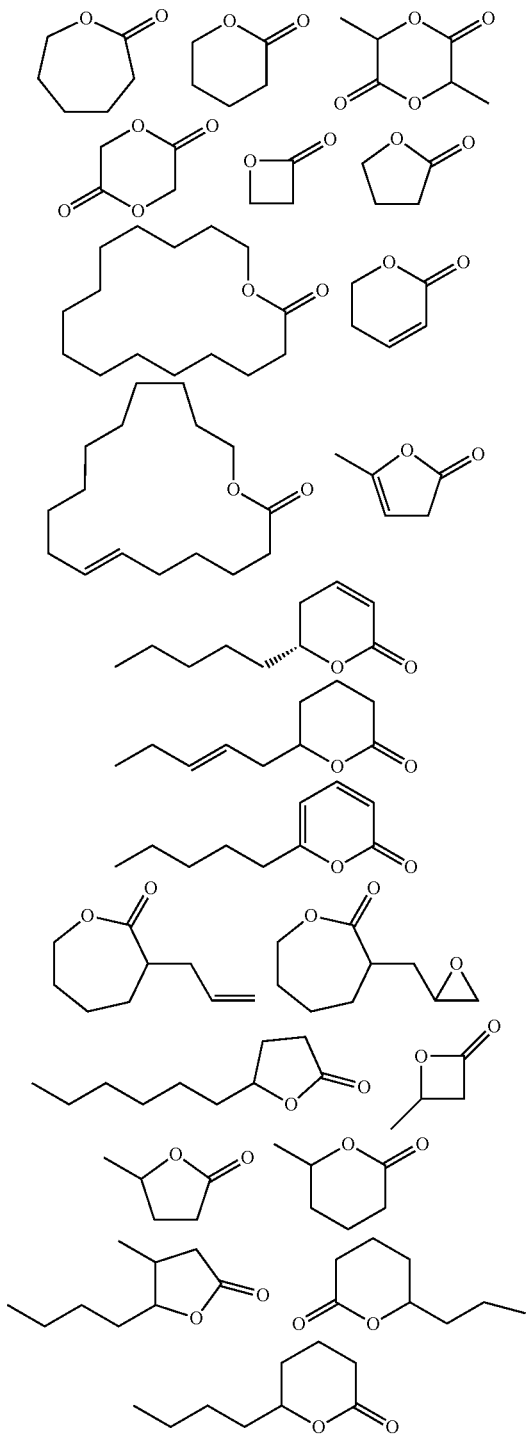
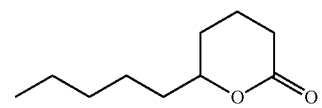
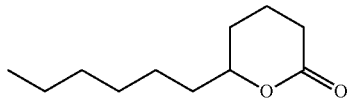
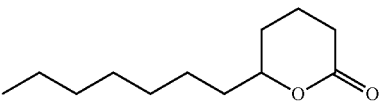
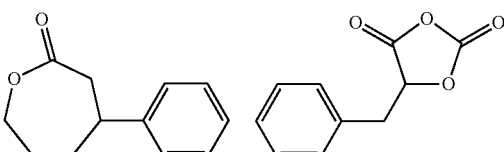
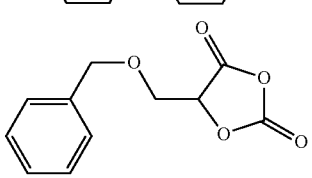
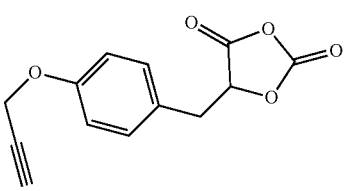
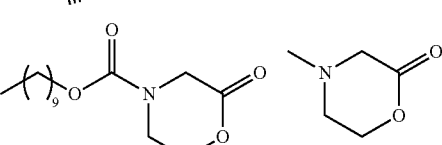
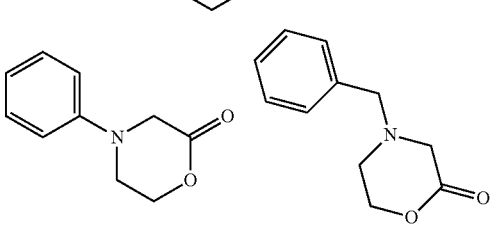
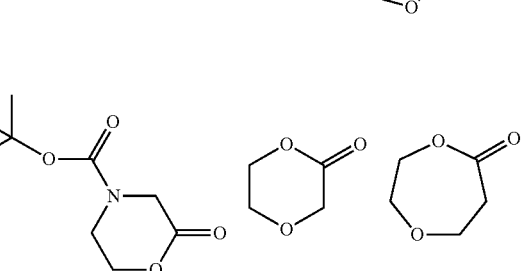
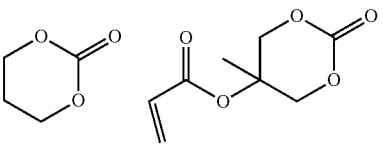

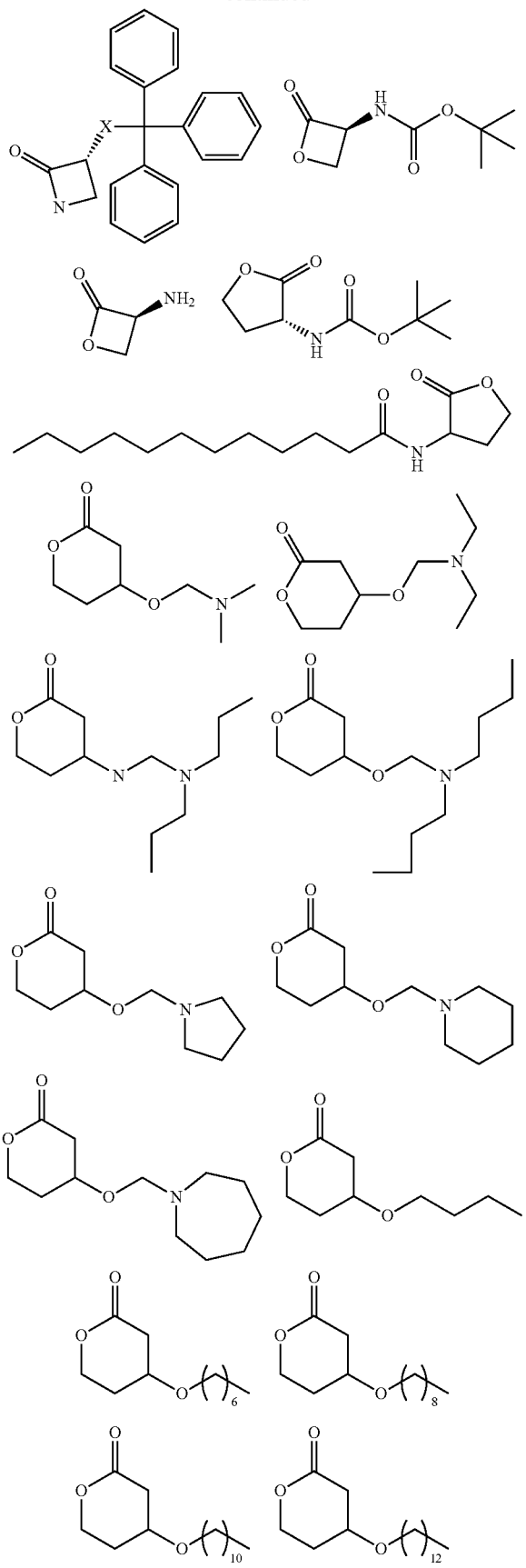
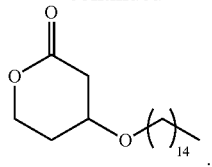

In certain embodiments, step of reacting comprises reacting a compound of Formula (VIa) with a lactone in the presence of a catalyst to obtain a compound of Formula (VIb). In certain embodiments, the catalyst is a Lewis acid. In certain embodiments, the Lewis acid is tin(II) 2-ethylhexanoate.

In certain embodiments, step of acylating comprises acylating the compound of Formula (VIb) with an electrophile of the formula:

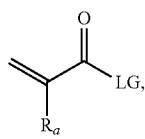

wherein LG is a leaving group, to obtain the compound of Formula (VI).

In certain embodiments, the acylating reagent is an acryloyl halide. In certain embodiments, the acylating agent is acryloyl chloride.

In certain embodiments, step of acylating further comprises acylating the compound of Formula (VIb) in the presence of a base. In certain embodiments, the base is a trialkylamine (e.g., trimethylamine, diisopropylethylamine, and the like).

The reactions described herein, which constitute the methods of preparing the compounds and polymers of the present disclosure, may further include the use of one or more solvents. Common solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene. In certain embodiments, each reaction independently is comprised of 1 to 10 solvents, inclusive. In certain embodiments, the reaction is comprised of one solvent. In certain embodiments, at least one one solvent is dichloromethane (DCM). In certain embodiments, at least one solvent is dimethylsulfoxide (DMSO).

The reactions described herein, which constitute the methods of preparing the compounds and polymers of the present disclosure, are performed at temperatures ranging between −10° C. and 150° C. In certain embodiments, the reaction is performed at temperatures below or at 50° C. In certain embodiments, the reaction is performed at temperatures above 50° C. In certain embodiments, the reaction is performed at approximately 0° C. In certain embodiments, the reaction is performed at room temperature. In certain embodiments, the reaction is performed at approximately 60° C. In certain embodiments, the reaction is performed at approximately 90° C. In certain embodiments, the reaction is performed at approximately 130° C.

The reactions described herein, which constitute the methods of preparing the compounds and polymers of the present disclosure, are performed for about 1 hour to about 120 hours. In certain embodiments, the reaction is performed for about 3 hours to about 72 hours. In certain embodiments, the reaction is performed for about 3 hours. In certain embodiments, the reaction is performed for about 24 hours. In certain embodiments, the reaction is performed for about 48 hours. In certain embodiments, the reaction is performed for about 72 hours.

In certain embodiments, the preparation of a compound of Formula (VI):

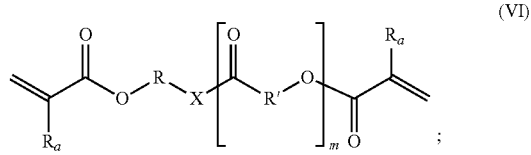

(VI)

comprises reacting a compound of Formula (VIa):

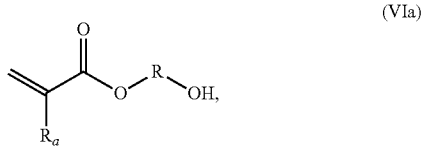

(VIa)

a lactone, a Lewis acid, and an acylating agent. Specific reaction conditions can be determined by those of ordinary skill in the art using no more than routine experimentation.

In certain embodiments, the compound of Formula (VIa):

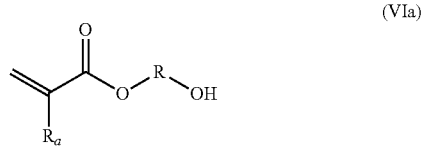

(VIa)

is 2-hydroxyethyl acrylate (HEA).

The lactone is used in an amount of about 1 to 15 equivalents of a compound of Formula (VIa). In certain embodiments, the lactone is used in an amount of about 1 to 10 equivalents of a compound of Formula (VIa). In certain embodiments, the lactone is used in an amount of about 1 to 7 equivalents of a compound of Formula (VIa). In certain embodiments, the lactone is used in an amount of about 1 to 5 equivalents of a compound of Formula (VIa). In certain embodiments, the lactone is used in an amount of about 1 to 3 equivalents of a compound of Formula (VIa). In certain embodiments, the lactone is used in an amount of about 7 equivalents of a compound of Formula (VIa). In certain embodiments, the lactone is used in an amount of about 5 equivalents of a compound of Formula (VIa). In certain embodiments, the lactone is used in an amount of about 3 equivalents of a compound of Formula (VIa).

The compound of Formula (VIa) is used in an amount of about 1 to 500 equivalents of the Lewis acid. In certain embodiments, the compound of Formula (VIa) is used in an amount of about 1 to 200 equivalents of the Lewis acid. In certain embodiments, the compound of Formula (VIa) is used in an amount of about 200 equivalents of the Lewis acid.

In certain embodiments, the preparation of a polymer of Formula (IV) comprises reacting a compound of Formula (VI), or a pharmaceutically acceptable salt thereof, with one or more amines of the formula: $R_1NH_2$. In certain embodiments, the preparation of a polymer of Formula (V) comprises reacting a compound of Formula (VI), or a pharmaceutically acceptable salt thereof, with one or more diamines of the formula:

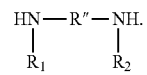

In certain embodiments, the preparation of a polymer of Formula (II), or a pharmaceutically acceptable salt thereof, comprises the reaction of a polymer of Formula (IV), or a pharmaceutically acceptable salt thereof, with one or more amines selected from $R_3NH_2$ and $R_4NH_2$. In certain embodiments, the preparation of a polymer of Formula (III), or a pharmaceutically acceptable salt thereof, comprises the reaction of a polymer of Formula (V), or a pharmaceutically acceptable salt thereof, with one or more amines selected from $R_3NH_2$ and $R_4NH_2$, as described herein.

In certain embodiments, the amine or diamine is selected from the group consisting of dodecyl amine, 3-amino-1,2-propanediol, 5-amino-pentanol, N,N-dimethylethylenediamine, 2-morpholinoethylamine, and 2,2'-((oxybis(ethane-2,1-diyl))bis(oxy))diethanamine.

Compositions and Kits

The present disclosure provides compositions (e.g., pharmaceutical compositions) comprising a polymer described herein, and an excipient (e.g., pharmaceutically acceptable excipient). In certain embodiments, the composition is a pharmaceutical composition. In certain embodiments, the composition is a cosmetic composition. In certain embodiments, the composition is a nutraceutical composition. In certain embodiments, the composition is a composition with a non-medical application. In certain embodiments, the excipient is a pharmaceutically acceptable excipient.

Compositions described herein can be prepared by any method known in the art. In general, such preparatory methods include bringing the polymer described herein into association with one or more excipients, and may include one or more agents and then, if necessary and/or desirable, shaping, and/or packaging the product into a desired single- or multi-dose unit. In certain embodiments, the agent and the polymer of the composition are not covalently attached.

In certain embodiments, the composition is in the form of a particle. In certain embodiments, the particle is a nanoparticle or a microparticle. In certain embodiments, the particle is a micelle, liposome, or lipoplex. In certain embodiments, the particle encapsulates an agent, as described herein. In certain embodiments, the particle facilitates delivery of the agent to a cell. See, e.g., FIGS. 5 and 10. In certain embodiments, the particle facilitates delivery of the agent to a subject, e.g., a human.

Nanoparticles and nanoparticle formulations are described herein. In certain embodiments, the nanoparticle comprises one or more additional lipids. In certain particular embodiments, the nanoparticle comprises a PEG-lipid. As described herein, PCL-based PBAE nanoparticles can be prepared using a pre-mixing protocol or a direct-mixing protocol. See, e.g., FIGS. 10 and 11.

Compositions can be prepared, packaged, and/or sold in bulk, as a single unit dose, and/or as a plurality of single unit doses. A "unit dose" is a discrete amount of the composition comprising a predetermined amount of the agent. The amount of the agent is generally equal to the dosage of the agent which would be administered to a subject and/or a convenient fraction of such a dosage, such as one-half or one-third of such a dosage.

Relative amounts of the polymer, excipient, agent, and/or any additional ingredients in a composition described herein will vary, depending upon the identity, size, and/or condition of the subject treated and further depending upon the route by which the composition is to be administered. The composition may comprise between 0.1% and 100% (w/w) agent.

Excipients and accessory ingredients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients and accessory ingredients, such as cocoa butter, PEGylated lipids, phospholipids, suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *Eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In certain embodiments, the compositions, further comprise an agent, and are useful for delivering said agent (e.g., to a subject or cell). In certain embodiments, the compositions are pharmaceutical compositions which are useful for treating a disease in a subject in need thereof. In certain embodiments, the pharmaceutical compositions are useful for preventing a disease in a subject. In certain embodiments, the pharmaceutical compositions are useful for diagnosing a disease in a subject.

A composition as described herein may further comprise, or can be administered in combination with, one or more additional agents. In certain embodiments, the agent is a small organic molecule, inorganic molecule, nucleic acid, protein, peptide, or polynucleotide. In certain embodiments, the agent is a pharmaceutical agent (e.g., therapeutically and/or prophylactically active agent). Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, polynucleotides, lipids, hormones, vitamins, vaccines, immunological agents, and cells or other biological materials.

In certain embodiments, the agent is a polynucleotide. In certain embodiments, the polynucleotide is DNA. In certain embodiments, the polynucleotide is RNA. In certain embodiments, the polynucleotide carries out RNA interference. The RNA is selected from the group consisting of double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA). In certain embodiments, the RNA is dsRNA. In certain embodiments, the RNA is siRNA. In certain embodiments, the RNA is shRNA. In certain embodiments, the RNA is miRNA. In certain embodiments, the RNA is mRNA. In certain embodiments, the RNA is antisense RNA.

In certain embodiments, the agent described herein is provided in an effective amount in the composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological disease in a subject in need thereof. In certain embodiments, the effective amount is an amount effective for preventing a hematological disease in a subject in need thereof. In certain embodiments, the effective amount is an amount effective for treating a neurological disease in a subject in need thereof. In certain embodiments, the effective amount is an amount effective for preventing a neurological disease in a subject in need thereof. In certain embodiments, the effective amount is an amount effective for treating a in a painful condition subject in need thereof. In certain embodiments, the effective amount is an amount effective for preventing a painful condition in a subject in need thereof. In certain embodiments, the effective amount is an amount effective for treating a psychiatric disorder in a subject in need thereof. In certain embodiments, the effective amount is an amount effective for preventing a psychiatric disorder in a subject in need thereof. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for reducing the risk of developing a disease (e.g., proliferative disease, hematological disease, neurological disease, infectious disease, inflammatory disease, autoimmune disease, gastrointestinal disease, liver disease, lung disease, kidney disease, spleen disease, familial amyloid neuropathies, painful condition, psychiatric disorder, or metabolic disorder) in a subject in need thereof.

In certain embodiments, the cell is in vitro. In certain embodiments, the cell is in vivo.

Compositions may be formulated into liquid dosage forms for oral and parenteral administration include pharmaceutically acceptable emulsions, microemulsions, solutions, suspensions, syrups and elixirs. In addition to the agents, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the particles described herein are mixed with solubilizing agents, such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of an agent, it is often desirable to slow the absorption of the drug from subcutaneous or intramuscular injection. This can be accomplished by the use of a liquid suspension of crystalline or amorphous material with poor water solubility. The rate of absorption of the agent then depends upon its rate of dissolution, which, in turn, may depend upon crystal size and crystalline form. Alternatively, delayed absorption of a parenterally administered drug form may be accomplished by dissolving or suspending the agent in an oil vehicle.

Compositions for rectal or vaginal administration are typically suppositories which can be prepared by mixing the particles described herein with suitable non-irritating excipients or carriers such as cocoa butter, polyethylene glycol, or a suppository wax which are solid at ambient temperature but liquid at body temperature and therefore melt in the rectum or vaginal cavity and release the agent.

Compositions may be formulated into solid dosage forms for oral administration include capsules, tablets, pills, powders, and granules. In such solid dosage forms, the agent is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the agent(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The agent can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the agent can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the agent(s) only, or preferentially, in a certain part of the intestinal tract, optionally, in a delayed manner. Examples of encapsulating agents which can be used include polymeric substances and waxes.

Dosage forms for topical and/or transdermal administration of a composition described herein may include ointments, pastes, creams, lotions, gels, powders, solutions, sprays, inhalants, and/or patches. Generally, the agent is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an agent to the body. Such dosage forms can be prepared, for example, by dissolving and/or dispensing the agent in the proper medium. Alternatively or additionally, the rate can be controlled by either providing a rate controlling membrane and/or by dispersing the agent in a polymer matrix and/or gel.

Suitable devices for use in delivering intradermal compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) agent, although the concentration of the agent can be as high as the solubility limit of the agent in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the agent and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the agent dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the agent may constitute 0.1 to 20% (w/w) of the composition. The propellant may further comprise additional ingredients such as a liquid non-ionic and/or solid anionic surfactant and/or a solid diluent (which may have a particle size of the same order as particles comprising the agent).

Compositions described herein formulated for pulmonary delivery may provide the agent in the form of droplets of a solution and/or suspension. Such formulations can be prepared, packaged, and/or sold as aqueous and/or dilute alcoholic solutions and/or suspensions, optionally sterile, comprising the agent, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the agent and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the agent, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) agent, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the agent. Such powdered, aerosolized, and/or aerosolized formulations, when dispersed, may have an average particle and/or droplet size in the range from about 0.1 to about 200 nanometers, and may further comprise one or more of the additional ingredients described herein.

A composition described herein can be prepared, packaged, and/or sold in a formulation for ophthalmic administration. Such formulations may, for example, be in the form of eye drops including, for example, a 0.1-1.0% (w/w) solution and/or suspension of the agent in an aqueous or oily liquid carrier or excipient. Such drops may further comprise buffering agents, salts, and/or one or more other of the additional ingredients described herein. Other opthalmically-administrable formulations which are useful include those which comprise the agent in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific agent employed; the specific composition employed; the age, body weight, general health, sex, and diet of the subject; the time of administration, route of administration, and rate of excretion of the specific agent employed; the duration of the treatment; drugs used in combination or coincidental with the specific agent employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a polymer described herein. In certain embodiments, a dose described herein includes independently between 1 mg and 3 mg, inclusive, of a polymer described herein. In certain embodiments, a dose described herein includes independently between 3 mg and 10 mg, inclusive, of a polymer described herein. In certain embodiments, a dose described herein includes independently between 10 mg and 30 mg, inclusive, of a polymer described herein. In certain embodiments, a dose described herein includes independently between 30 mg and 100 mg, inclusive, of a polymer described herein.

Dose ranges as described herein provide guidance for the administration of provided compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

The compositions can be administered in combination with additional agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a composition described herein including a polymer described herein and an agent shows a synergistic effect that is absent in a composition including one of the polymer and an agent, but not both.

The composition can be administered concurrently with, prior to, or subsequent to one or more additional agents, which are different from the composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the polymer or composition described herein in a single dose or administered separately in different doses. The particular combination to employ in a regimen will take into account compatibility of the polymer described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the polymers described herein or pharmaceutical compositions can be administered in combination with an anti-cancer therapy including surgery, radiation therapy, transplantation (e.g., stem cell transplantation, bone marrow transplantation), immunotherapy, and chemotherapy.

In some embodiments, the composition is a particle (e.g., a nanoparticle). In some embodiments, the particle is substantially soluble in water (e.g., hydrophilic). In some embodiments, the particle is substantially insoluble in water (e.g., hydrophobic). In some embodiments, the particle is substantially insoluble in water and greater than about 10,000 parts water are required to dissolve 1 part polymer. In one embodiment, the particle is amphiphilic. In one embodiment, the particle comprises a segment that is hydrophobic and a segment that is hydrophilic.

In some embodiments, the percentage of the particles that comprise an agent is between about 1 and about 100% (e.g., about 1%, about 2%, about 3%, about 4%, about 5%, about 10%, about 15%, about 20%, about 30%, 0%, a 40%, about 50%, about 60%, about 70%, about 80%, about 90%, or about 100%). In some embodiments, the percentage of the particles that comprise an agent is less than about 50%, e.g., less than about 40%, less than about 35%, less than about 30%, less than about 25%, less than about 20%, less than about 15%, or less than about 10%. In some embodiments, the percentage of the particles that comprise an agent is between about 5% and about 50%, about 5% and about 40%, about 5% and about 30%, about 5% and about 25%, or about 5% and about 20%. In some embodiments, the percentage of the particles that comprise an agent is between about 5% and 90%. In some embodiments, the percentage of the particles that comprise an agent is between about 5% and about 75%. In the some embodiments, the percentage of particles that comprise an agent is between about 5% and about 50%. In the some embodiments, the percentage of the particles that comprise an agent is between about 10% and about 25%.

In some embodiments, the total amount of the agent present in the particle is greater than about 5% (e.g., about 6%, about 7%, about 8%, about 9%, about 10%, about 12%, about 15%, about 20%, about 25%, about 30%, or more) of the total size or weight of the conjugate or particle. In some embodiments, the total amount of the agent present in the conjugate or particle is greater than about 10% (e.g., about 12%, about 15%, about 20%, about 25%, about 30%, or more) of the total size or weight of the conjugate or particle.

Without being bound by theory, the polymers or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell). Accordingly, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a polymer, conjugate or particle described herein).

Without being bound by theory, due to the localized delivery of the compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent. In one embodiment, the agent are incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). In some embodiments, since the particle described herein releases the agent at a target site based on pH microenvironment, other non-target sites (e.g., blood vessels) with different pH would be less likely to be exposed to the agent.

In another aspect, provided are kits including a first container comprising a polymer or composition described herein and instructions for use. The kits may further comprise a container (e.g., a vial, ampule, bottle, syringe, and/or dispenser package, or other suitable container). In some embodiments, provided kits may optionally further include a second container comprising an excipient for dilution or suspension of a composition or polymer described herein. In some embodiments, the composition described herein provided in the first container and the second container are combined to form one unit dosage form.

In certain embodiments, the kits are useful for delivering an agent (e.g., to a subject or cell). In certain embodiments, the kits are useful for treating a disease (e.g., proliferative disease, hematological disease, neurological disease, painful condition, psychiatric disorder, or metabolic disorder) in a subject in need thereof. In certain embodiments, the kits are useful for preventing a disease (e.g., proliferative disease, hematological disease, neurological disease, painful condition, psychiatric disorder, or metabolic disorder) in a subject in need thereof. In certain embodiments, the kits are useful for reducing the risk of developing a disease (e.g., proliferative disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein kinase in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for delivering an agent. In certain embodiments, the kits and instructions provide for treating a disease (e.g., proliferative disease, hematological disease, neurological disease, painful condition, psychiatric disorder, or metabolic disorder) in a subject in need thereof. In certain embodiments, the kits and instructions provide for preventing a disease (e.g., proliferative disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

Methods of Treatment and Uses

The present disclosure also provides methods of using the compositions described herein, or a pharmaceutical composition thereof, for delivering an agent. The present disclosure also provides methods of using the polymers described herein, or a pharmaceutical composition thereof, for the treatment, prevention, or diagnosis of a disease or condition.

In certain embodiments, the methods described herein include treating a disease, disorder, or condition from which a subject suffers, comprising administering to a subject in need thereof an effective amount of a composition described herein. In certain embodiments, the methods described herein include implanting in a subject an effective amount of the composition described herein. In certain embodiments, the methods described herein comprise treating a disease or condition in a subject in need thereof by administering to or implanting in the subject a therapeutically effective amount of a composition. In certain embodiments, the methods described herein comprise preventing a disease or condition in a subject in need thereof by administering to or implanting in the subject a prophylactically effective amount of a composition. In certain embodiments, the methods described herein comprise diagnosing a disease or condition in a subject in need thereof by administering to or implanting in the subject a diagnostically effective amount of a composition.

In certain embodiments, the disease or condition is a genetic disease, proliferative disease, hematological disease, neurological disease, painful condition, psychiatric disorder, metabolic disorder, long-term medical condition, cancer (e.g. lung cancer, large bowel cancer, pancreas cancer, biliary tract cancer, or endometrial cancer), neoplasm, angiogenesis, inflammatory disease, autoinflammatory disease, liver disease, lung disease, spleen disease, familial amyloid neuropathy, cardiovascular disease, viral infection, fibrotic condition, or autoimmune disease.

In some embodiments, the compositions are useful in treating lung cancer, head-and-neck cancer, esophagus cancer, stomach cancer, breast cancer, pancreas cancer, liver cancer, kidney cancer, prostate cancer, glioblastomas, metastatic melanomas, peritoneal or pleural mesotheliomas.

In some embodiments, the proliferative disease is a benign neoplasm. All types of benign neoplasms disclosed herein or known in the art are contemplated as being within the scope of the disclosure. In some embodiments, the proliferative disease is associated with angiogenesis. All types of angiogenesis disclosed herein or known in the art are contemplated as being within the scope of the disclosure. In certain embodiments, the proliferative disease is an inflammatory disease. All types of inflammatory diseases disclosed herein or known in the art are contemplated as being within the scope of the disclosure. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the disclosure. In some embodiments, the proliferative disease is an autoimmune disease. All types of autoimmune diseases disclosed herein or known in the art are contemplated as being within the scope of the disclosure.

In certain embodiments, the disease is a cardiovascular disease. In certain embodiments, the disease is atherogenesis or atherosclerosis. In certain embodiments, the disease is arterial stent occlusion, heart failure (e.g., congestive heart failure), a coronary arterial disease, myocarditis, pericarditis, a cardiac valvular disease, stenosis, restenosis, in-stent-stenosis, angina pectoris, myocardial infarction, acute coronary syndromes, coronary artery bypass grafting, a cardiopulmonary bypass procedure, endotoxemia, ischemia-reperfusion injury, cerebrovascular ischemia (stroke), renal reperfusion injury, embolism (e.g., pulmonary, renal, hepatic, gastrointestinal, or peripheral limb embolism), or myocardial ischemia.

In certain embodiments, the disease is a viral infection. In certain embodiments, the disease is an infection caused by DNA virus. In certain embodiments, the disease is an infection caused by a dsDNA virus. In certain embodiments, the disease is an infection caused by an ssDNA virus. In certain embodiments, the disease is an infection caused by an RNA virus. In certain embodiments, the disease is an infection caused by a dsRNA virus. In certain embodiments, the disease is an infection caused by a (+)ssRNA virus. In certain embodiments, the disease is an infection caused by a (−)ssRNA virus. In certain embodiments, the disease is an infection caused by a reverse transcribing (RT) virus. In certain embodiments, the disease is an infection caused by an ssRNA-RT virus. In certain embodiments, the disease is an infection caused by a dsDNA-RT virus. In certain embodiments, the disease is an infection caused by human immunodeficiency virus (HIV). In certain embodiments, the disease is an infection caused by acquired immunodeficiency syndrome (AIDS). In certain embodiments, the disease is an infection caused by human papillomavirus (HPV). In certain embodiments, the disease is an infection caused by hepatitis C virus (HCV). In certain embodiments, the disease is an infection caused by a herpes virus (e.g., herpes simplex virus (HSV)). In certain embodiments, the disease is an infection caused by Ebola virus. In certain embodiments, the disease is an infection caused by severe acute respiratory syndrome (SARS). In certain embodiments, the disease is an infection caused by influenza virus. In certain embodiments, the disease is an infection caused by an influenza virus. In certain embodiments, the disease is an infection caused by an influenza A virus. In certain embodiments, the disease is human flu (e.g., human flu caused by H1N1, H2N2, H3N2, H5N1, H7N7, H1N2, H9N2, H7N2, H7N3, or H10N7 virus). In certain embodiments, the disease is bird flu (e.g., bird flu caused by H5N1 or H7N9 virus). In certain embodiments, the disease is swine influenza (e.g., swine influenza caused by H1N1, H1N2, H2N1, H3N1, H3N2, H2N3, or influenza C virus). In certain embodiments, the disease is equine influenza (e.g., equine influenza caused by H7N7 or H3N8 virus). In certain embodiments, the disease is canine influenza (e.g., canine influenza caused by H3N8 virus). In certain embodiments, the disease is an infection caused by an influenza B virus. In certain embodiments, the disease is an infection caused by an influenza C virus. In certain embodiments, the disease is Dengue fever, Dengue hemorrhagic fever (DHF), Dengue shock syndrome (DSS), hepatitis A, hepatitis B, hepatitis D, hepatitis E, hepatitis F, infection caused by Coxsackie A virus, infection caused by Coxsackie B virus, fulminant viral hepatitis, viral myocarditis, infection caused by parainfluenza virus, infection caused by an RS virus (RSV) (e.g., RSV bronchiolitis, RSV pneumonia, especially an infant and childhood infection caused by RSV and RSV pneumonia in the patients with cardiopulmonary disorders), infection caused by measles virus, infection caused by vesicular stomatitis virus, infection caused by rabies virus, Japanese encephalitis, infection caused by Junin virus, infection caused by human cytomegalovirus, infection caused by varicellovirus, infection caused by cytomegalovirus, infection caused by muromegalovirus, infection caused by proboscivirus, infection caused by roseolovirus, infection caused by lymphocryptovirus, infection caused by macavirus, infection caused by percavirus, infection caused by rhadinovirus, infection caused by poliovirus, infection caused by Marburg virus, infection caused by Lassa fever virus, Venezuelan equine encephalitis, infection caused by Rift Valley Fever virus, infection caused by Korean hemorrhagic fever virus, infection caused by Crimean-Congo hemorrhagic fever virus, encephalitis, Saint Louise encephalitis, Kyasanur Forest disease, Murray Valley encephalitis, tick-borne encephalitis, West Nile encephalitis, yellow fever, infection caused by adenovirus, infection caused by poxvirus, or a viral infection in subjects with immune disorders.

In certain embodiments, the disease is a fibrotic condition. In certain embodiments, the disease is selected from the group consisting of renal fibrosis, post-operative stricture, keloid formation, hepatic cirrhosis, biliary cirrhosis, and cardiac fibrosis. In certain embodiments, the disease is scleroderma. In certain embodiments, the disease is idiopathic pulmonary fibrosis.

In certain embodiments, the methods described herein include contacting a cell with an effective amount of a composition thereof. In certain embodiments, the cell is in vitro. In certain embodiments, the cell is in vivo.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Figure 4:
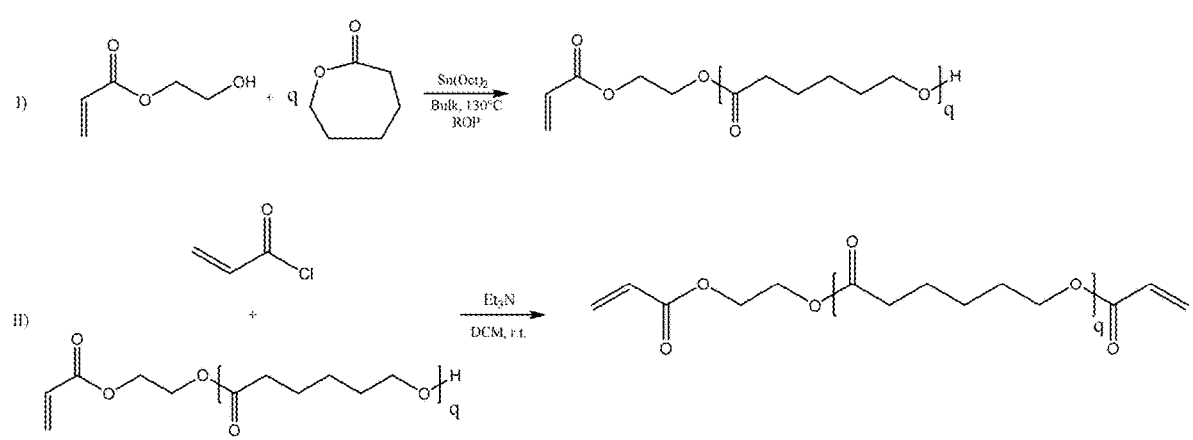
FIG. 4 shows the synthesis of poly-caprolactone-based diacrylates.

In some examples, polylactone diacrylates with different numbers of lactone units have been synthesized according to FIG. 4 and used in the synthesis of novel polylactone-based PBAEs with the same procedure shown in FIG. 1. These novel carriers have further been formulated with oligonucleotides and polynucleotides to form nanoparticles, which are transfected into cells.

The present disclosure provides formulations of the polymers described herein with mRNA to form nanoparticles. Such nanoparticles can be used to transfect the mRNA into cells, including, e.g., HeLa cells. The potency of these novel nanoparticles has been evaluated and is comparable to the potency of one of the current top performing PBAEs polymers (DD90-C12-122).[9f] The polylactone-based PBAEs with 5 units of ε-caprolactone (caprolactone or CL) shows a higher transfection efficiency than DD90-C12-122. In particular, the PBAE C1 is five times more effective and 35% less cytotoxic than DD90-C12-122. In addition, C1 does not release compounds that may induce side effects that are difficult to evaluate with a cellular assay, such as those related to a systematic toxicity and genotoxicity.

Experimental Section

Materials

All chemicals were used as received except when specifically noted. All the solvents used were of analytical-grade purity and were purchased from Sigma Aldrich. ε-caprolactone (CL), acryloyl chloride, triethylamine, 2-hydroxyethyl acrylate (HEA), 4-methoxyphenol, tin(II) 2-ethylhexanoate, bisphenol A glycerolate (DD), ethylene glycol diacrylate (A), dodecyl amine (C12), 4-(2-aminomethyl) morpholine (4), (+/−)-3amino-1,2-propanediol (1), N—N'-dimethyl ethylene diamine (3) were obtained from Sigma Aldrich (St. Louis, Mo., USA). 14:0 PEG2000 PE (PEG-lipid) was purchased from Avanti Polar Lipids (Alabaster, Ala., USA). 5-amino-1-pentaol (2) and heparin sodium salt were obtained from ALFA Aesar (Haverhill, Mass., USA).

Firefly luciferase (FLuc) mRNA was generously provided by Shire Pharmaceuticals (Lexington, Mass.). FLuc mRNA contained a 5' cap (Cap1), a 5' UTR consisting of a partial sequence of the cytomegalovirus (CMV) immediate early 1 (IE1) gene, a coding region as described below, a 3' UTR consisting of a partial sequence of the human growth hormone (hGH) gene, and a 3' polyA tail.

Firefly luciferase (FLuc) mRNA sequence:

(SEQ ID NO: 1)
AUGGAAGAUGCCAAAAACAUUAAGAAGGGCCCAGCGCCAUUCUACCCA

CUCGAAGACGGGACCGCCGGCGAGCAGCUGCACAAAGCCAUGAAGCGC

UACGCCCUGGUGCCCGGCACCAUCGCCUUUACCGACGCACAUAUCGAG

GUGGACAUUACCUACGCCGAGUACUUCGAGAUGAGCGUUCGGCUGGCA

GAAGCUAUGAAGCGCUAUGGGCUGAAUACAAACCAUCGGAUCGUGGUG

UGCAGCGAGAAUAGCUUGCAGUUCUUCAUGCCCGUGUUGGGUGCCCUG

UUCAUCGGUGUGGCUGUGGCCCCAGCUAACGACAUCUACAACGAGCGC

GAGCUGCUGAACAGCAUGGGCAUCAGCCAGCCCACCGUCGUAUUCGUG

AGCAAGAAAGGGCUGCAAAAGAUCCUCAACGUGCAAAAGAAGCUACCG

AUCAUACAAAAGAUCAUCAUCUGGAUAGCAAGACCGACUACCAGGGC

UUCCAAAGCAUGUACACCUUCGUGACUUCCCAUUUGCCACCCGGCUUC

AACGAGUACGACUUCGUGCCCGAGAGCUUCGACCGGGACAAAACCAUC

GCCCUGAUCAUGAACAGUAGUGGCAGUACCGGAUUGCCCAAGGGCGUA

GCCCUACCGCACCGCACCGCUUGUGUCCGAUUCAGUCAUGCCCGCGAC

CCCAUCUUCGGCAACCAGAUCAUCCCCGACACCGCUAUCCUCAGCGUG

GUGCCAUUUCACCACGGCUUCGGCAUGUUCACCACGCUGGGCUACUUG

AUCUGCGGCUUUCGGGUCGUGCUCAUGUACCGCUUCGAGGAGGAGCUA

UUCUUGCGCAGCUUGCAAGACUAUAAGAUUCAAUCUGCCCUGCUGGUG

CCCACACUAUUUAGCUUCUUCGCUAAGAGCACUCUCAUCGACAAGUAC

GACCUAAGCAACUUGCACGAGAUCGCCAGCGGCGGGGCGCCGCUCAGC

AAGGAGGUAGGUGAGGCCGUGGCCAAACGCUUCCACCUACCAGGCAUC

CGCCAGGGCUACGGCCUGACAGAAACAACCAGCGCCAUUCUGAUCACC

CCCGAAGGGGACGACAAGCCUGGCGCAGUAGGCAAGGUGGUGCCCUUC

UUCGAGGCUAAGGUGGUGGACUUGGACACCGGUAAGACACUGGGUGUG

AACCAGCGCGGCGAGCUGUGCGUCCGUGGCCCCAUGAUCAUGAGCGGC

UACGUUAACAACCCCGAGGCUACAAACGCUCUCAUCGACAAGGACGGC

UGGCUGCACAGCGGCGACAUCGCCUACUGGGACGAGGACGAGCACUUC

UUCAUCGUGGACCGGCUGAAGAGCCUGAUCAAAUACAAGGGCUACCAG

GUAGCCCCAGCCGAACUGGAGAGCAUCCUGCUGCAACACCCCAACAUC

UUCGACGCCGGGGUCGCCGGCCUGCCCGACGACGAUGCCGGCGAGCUG

CCCGCCGCAGUCGUCGUGCUGGAACACGGUAAAACCAUGACCGAGAAG

GAGAUCGUGGACUAUGUGGCCAGCCAGGUUACAACCGCCAAGAAGCUG

CGCGGUGGUGUUGUGUUCGUGGACGAGGUGCCUAAAGGACUGACCGGC

AAGUUGGACGCCCGCAAGAUCCGCGAGAUUCUCAUUAAGGCCAAGAAG

GGCGGCAAGAUCGCCGUGUAA

General Methods and Instruments

1) Synthesis of the Polylactone-Based Diacrylates

Polylactone-based diacrylates were synthesized in a two-step procedure: (i) ring opening polymerization of CL with HEA as initiator and tin(II) 2-ethylhexanoate as catalyst and (ii) esterification with acryloyl chloride (see FIG. 4). In the first step, the ring opening polymerization was carried out in bulk with a CL to HEA ratio and HEA to tin(II) 2-ethylhexanoate ratio equal to 3, 5 and 7 and 1/200, respectively. As an example for q=3, 1 g of CL, 17 mg of $Na_2SO_4$ and 1 mg of 4-methoxyphenol were weighted in a septa-sealed flask and heated to 130° C. in a constant temperature oil bath under stirring. 1 g of HEA were mixed with 17 mg of tin(II) 2-ethylhexanoate in a different vial and injected into the pre-heated CL containing flask. The polymerization was allowed to proceed for 3 hours. An aliquot was taken to perform $^1$H NMR (in $CDCl_3$) and GPC (in THF). In the second step, the esterification was carried out in dichloromethane with 2 equivalent of triethylamine and acryloyl chloride. As an example for q=3, 3.95 g of the previous macro-monomer and 2.4 ml of triethylamine were dissolved in 50 ml of DCM and poured in a septum sealed round-bottom flask. 1.4 ml of acryloyl chloride were added dropwise into the reactor under inert atmosphere at 0° C. and under stirring. The reaction was left to equilibrate to room temperature and then stopped after 24 h. The final mixture was filtered and washed several times with water and brine. The mixture was dried over $Na_sSO_4$ and the solvent eliminated via rotavapor. The final diacrylate was dried under vacuum and characterized via NMR and GPC. The PCL-based custom diacrylates were characterized via $^1$H NMR (400 MHz, $CDCl_3$) on a Bruker spectrometer.

Polylactone-based diacrylates and PBAE polymers were dissolved in tetrahydrofuran (THF) at a concentration of 4 mg ml$^{-1}$, filtered over 0.2 um PTFE syringe filter and eluted in Styragel columns at a 1 ml min$^{-1}$ flow rate. The instrument is equipped with a Malvern Viscotek™ TDA 305 triple detector. Molecular weights and polydispersities were relative to linear polystyrene standards.

2) PBAE Synthesis

Figure 5:
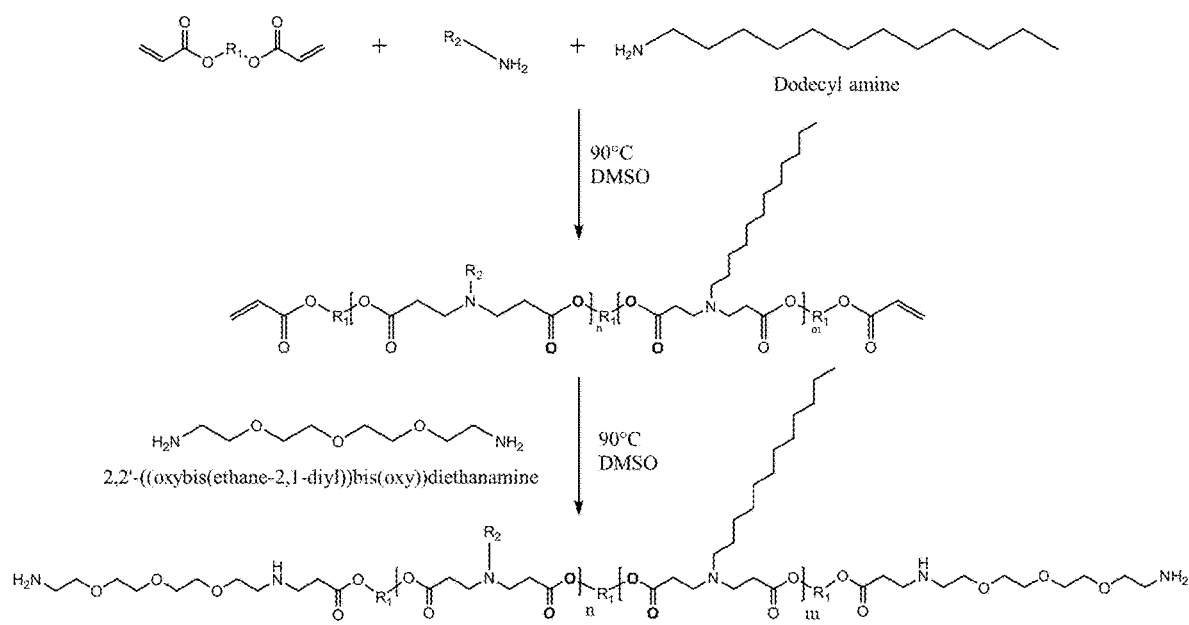
FIG. 5 shows an embodiment of the synthesis of PBAE polymers using exemplary amines and diacrylates.
Figure 6:
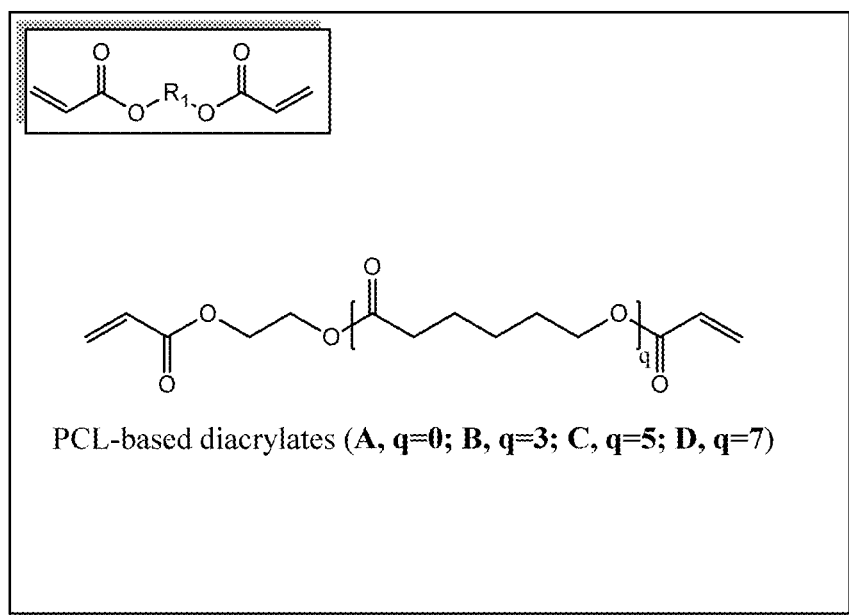
FIG. 6 shows exemplary PCL-based diacrylates used in the the synthesis of PBAE polymers.
Figure 7:
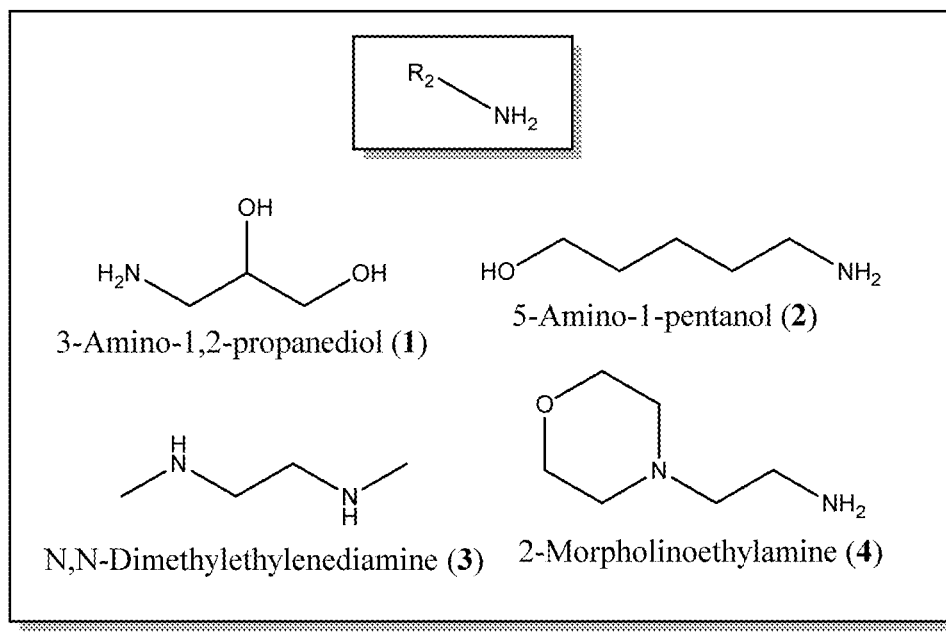
FIG. 7 shows exemplary amines used in the the synthesis of PBAE polymers.

In certain embodiments, alkyl-side chain containing polymers were synthesized as shown in FIG. 5. Briefly, the diacrylate monomer, the C12 amine and the hydrophilic amine were dissolved in DMSO at a concentration of 0.6 M and added in a 4 ml vials in such way that their molar ratio was 1.2:0.3:0.7. The hydrophobic C12 amine was heated to 60° C. before addition to the reaction medium in order to avoid crashing out. The reaction was purged with nitrogen for 2 minutes and heated to 90° C. After 2 days, the end capping was added and the reaction re-started at 90° C. for an additional day. The final concentration was adjusted to 100 mg ml$^{-1}$ by adding more DMSO and the samples were divided into aliquots and stored at −80° C.

3) Nanoparticle Formulation

Two different procedures were adopted to produce the nanoparticles (NPs). In the first case, 5 ul of the 100 mg ml$^{-1}$ polymer solution in DMSO were dissolved in 195 ul of 25 mM NaOAc and then mixed by pipetting with 200 ul of a solution of 50 ng/ul of mRNA in 25 mM NaOAc buffer. In the second case, 5 ul of the 100 mg ml$^{-1}$ polymer solution in DMSO were dissolved in 45 ul of ethanol with different amount of PEG-lipid when specifically noted and mixed by pipetting with 50 ul of a solution of 200 ng/ul of mRNA in 25 mM NaOAc buffer. The final mixture was finally diluted with PBS to reach the mRNA final concentration of 5 ng/ul.

Nanoparticle (NP) size, PDI (polydispersity index), and ξ potential (i.e., zeta potential; electrokinetic potential) were obtained using a Zetasizer (Malvern). For size measurement, NPs were diluted in PBS at a 1/40 v/v ratio and an intensity average size was reported. For the ξ potential measurements, NPs were diluted in deionized water at a ratio of 1/40 v/v.

4) Transfection Tests

20000 HeLa cells in 100 ul of freshly prepared medium were seeded into each well of a 96-well white polystyrene tissue culture plate (Costar®) and left to grow for a day. In a typical experiment, for a mRNA dose of 50 ng/well, 50 ul of the 5 ug/ul mRNA NP formulation were mixed with 450 ul of freshly prepared medium pre-heated to 37° C. The conditioned medium was removed by the wells and replaced with 100 ul of the diluted mRNA NP formulation. The HeLa cells were left to incubate for another day. The MultiTox-Fluor Multiplex Cytotoxicity Assay (Promega) and cellular Bright-Glo kits (Promega) were carried out according to the specifications of the producer in order to evaluate the cell viability and the cellular luminescence via a Tecan plate reader. Cellular luminescence was normalized to live cell count that, in turn, was determined via a standard curve made using the viability assay.

5) In Vivo Experiments 20 ul of PBAE (100 ug/ul in DMSO) and different amount of PEG-lipid were dissolved in 180 ul of ethanol and then mixed by repeated pipetting to the aqueous phase consisting of 40 ul of 1 mg/ml mRNA and 160 ul of 25 mM NaOAc buffer. After 10 min, the NPs were dialyzed against 4 L of PBS at 4° C. in 20000 MWCO cassettes (Thermo Fisher). The mRNA concentration of the final NPs were evaluated via a modified Quanti-iT RiboGreen RNA assay (Thermo Fisher) according to a previous work[24]. In vivo jetPEI (Polyplus) was used according to manufacturer instructions at an N/P of 8, the maximum recommended polymer:nucleic acid ratio.

NP formulations were injected via tail vein in female C57BL/6 mice (Charles River Laboratories, 18-22 g). 130 uL of 30 mg ml$^{-1}$ D-luciferin (PerfkinElmer) in PBS were injected intraperitoneally 24 hours after the administration of the NP formulation for luciferase image experiments. Mice were sacrificed via $CO_2$ asphyxiation 10 min after D-luciferin injection. The luminescence of the pancreas, spleen, kidneys, liver, lungs, and heart was quantified via an IVIS imaging apparatus (PerkinElmer). 24 hours following intravenous nanoparticle injection in mice, blood samples were collected via the tail vein in serum collection tubes (Sarstedt). Serum was collected from the blood, and ALT and AST activities were analyzed using AST and ALT colorimetric/fluorometric activity assay kits (Sigma). Assays were performed according to manufacturer instructions, and enzyme activities were normalized to those of PBS-treated mice.

6) Nanoparticle Stability Test

After synthesizing NPs for the in vivo tests, the final concentration was adjusted to 50 ng/ul mRNA. 90 ul of NP solution was added to each well of a transparent 96 well plate. The absorbance of each plate was measured initially at 660 nm. After the addition of 10 ul of fetal bovine serum, the plate was incubated at 37° C. and the absorbance was measured at the same wavelength after 15, 30, 45, 60, 90 and 120 minutes.

DISCUSSION

The polylactone-based diacrylates were synthesized via a novel two-step procedure that consists of (i) a ring opening polymerization of caprolactone (CL) with 2-hydroxyethyl-acrylate (HEA) as initiator and tin(II)-ethylhexanoate as catalyst and (ii) acylation with acryloyl chloride (see FIG. 4).

Figure 8B:
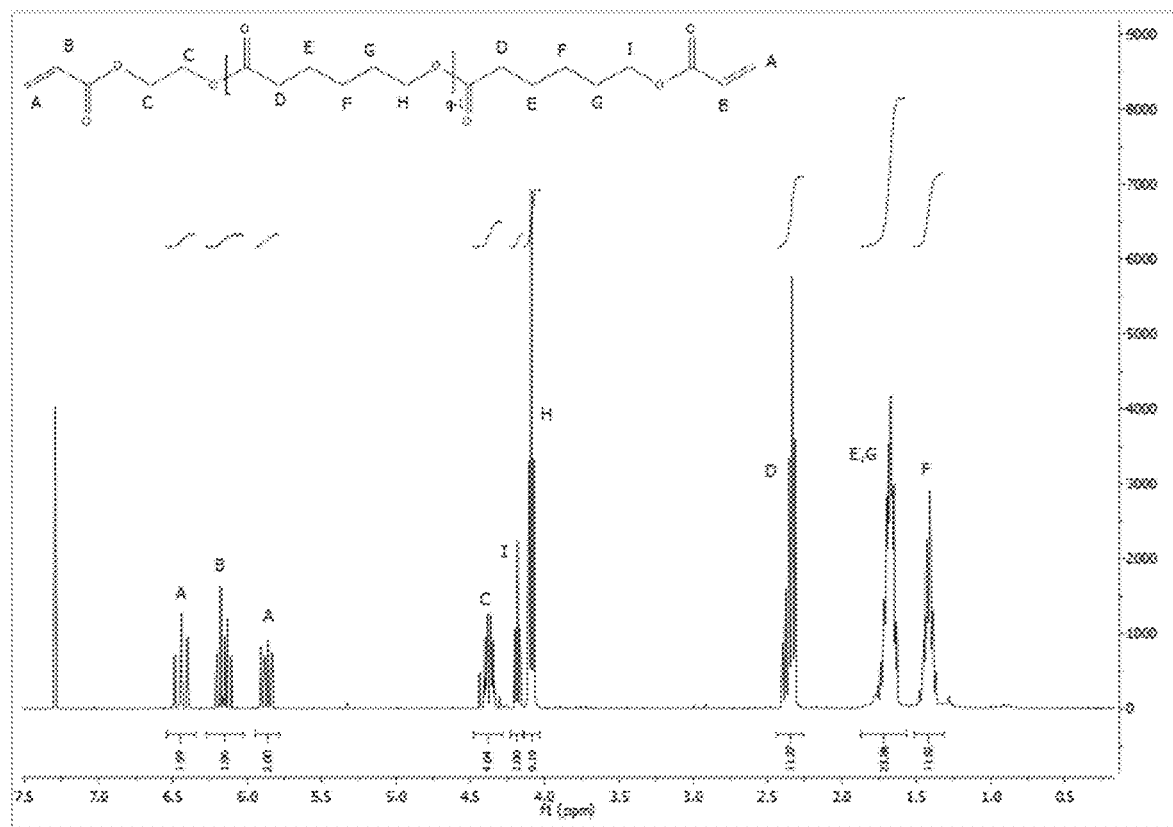

The ROP is a so-called "living polymerization", a technique that allows for control over the number of the units of caprolactone (q) that can be attached to the final diacrylate. In addition to PCL being inherently more biocompatible than other diacrylates, the tunability of q by varying the reaction stoichiometry allows for control over the diacrylate's (and therefore the PBAE's) lipophilicity and molecular weight. In addition, the polymerization does not require any solvent or further purification steps due to the nearly complete conversion and the absence of by-products[25]. For this reason, the obtained macromonomer can be directly used in the second step of the synthesis of the custom diacrylates, an esterification with acryloyl chloride. This latter step was used to attach the additional double bond required to produce the PBAE polymers via Michael step-growth polymerization. An ethylenglycol diacrylate (A), which has a q value equal to 0, has been used in previous PBAEs.[9f] Three different PCL-based diacrylates were synthesized with a low polydispersity (Đ<1.3) and theoretical q values very close to the one evaluated via $^1$H NMR (data in table of FIG. 8A and representative $^1$H NMR of a custom diacrylate in FIG. 8B).

In certain embodiments, PBAEs incorporating the custom diacrylates were synthesized in a two-step reaction.[9f] In the first step, as shown in FIG. 5, an alkyl amine (dodecylamine) and different hydrophilic amines (1, 2, 3, 4) were reacted with the custom diacrylates (A, B, C, D) at a ratio equal to 1.2:0.7:0.3 (diacrylate:hydrophilic amine:dodecyl amine) to produce a library of acrylate-terminated PBAE polymers. The choice to incorporate a lipophilic amine in the PBAE is justified by the superior stability and efficiency of the polymers to deliver DNA compared to classic PBAE polymers.[9f] The second step is carried out without any intermediate purification and consists in another Michael addition with an excess of a PEGylated diamine in order to completely consume the remaining double bonds in the mixture. In fact, the end-capping of the PBAE polymers has shown to increase the transfection efficiency and to reduce their toxicity.[26,27]

Figure 10A:
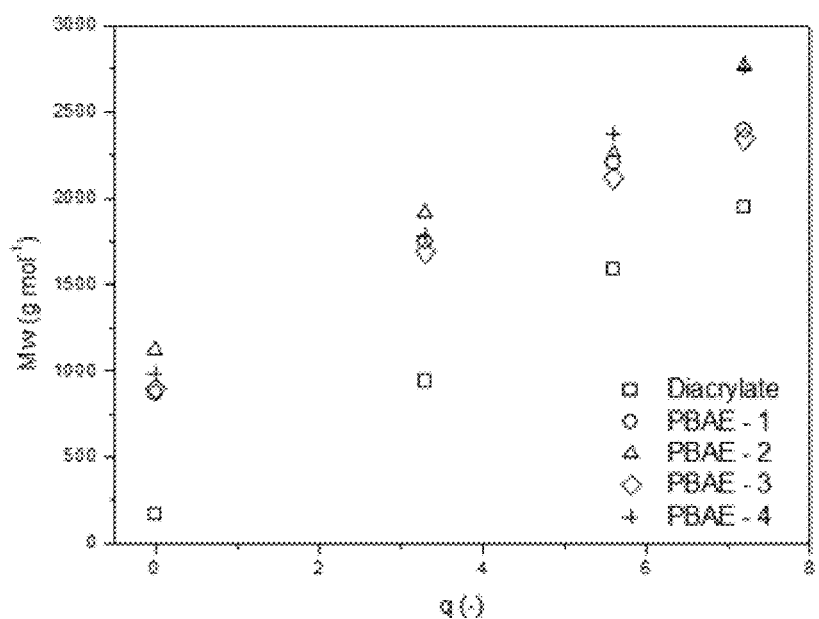
FIGS. 10A to 10D show.
Figure 11:
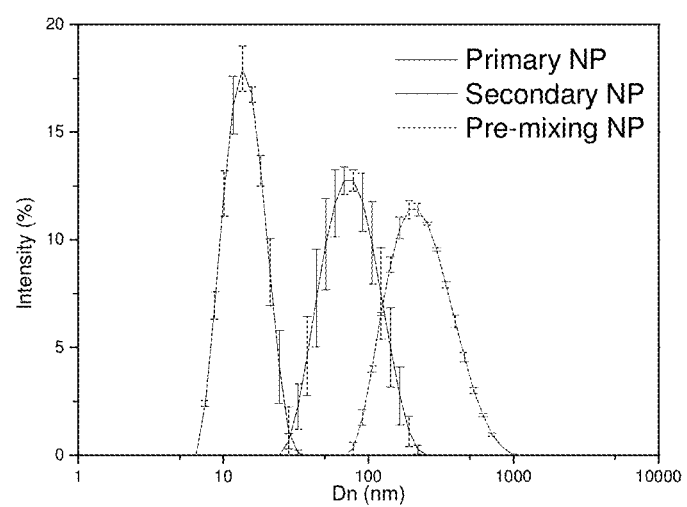
FIG. 11 shows NP PEG-lipid distributions of B2 for the primary and secondary NPs obtained in the direct mixing protocol and NP $D_n$ distribution of the same PBAE with the pre-mixing protocol.

The PBAE polymers synthesized show a high Đ (see FIG. 9) as expected from a step-growth polymerization, but in addition they show a linear behavior of $M_w$ within the adoption of the same hydrophilic amine in a way similar to the custom diacrylate (FIG. 10A).

In fact, the $M_w$ obtained via GPC is a linear function of the number of CL units attached with the intercept equal to the $M_w$ of the diacrylate A due to the control given by the ring opening polymerization. Thus, despite the fact that Michael addition polymerization is known to require high conversion and the complete absence of impurities in the mixture, this novel strategy allowed us to improve the control over the $M_w$ and the lipophilicity of the final material. However, it is important to note that as long as the number of amines per each polymer chain is theoretically the same for a pre-assigned stoichiometry,[28] the increase of the $M_w$ results in a reduction by weight of the overall ionizable charges (i.e. charge density).

The lipophilicity of the polymer also plays an important role in the production of the NPs since it can affect its solubility in the medium that is used for the ionic complexation of the oligonucleotides. For this reason, two different procedures were adopted in order to evaluate the effect of the formulation method on the NPs size and, in turn, on their transfection efficiency in vitro. In the first case, so called direct mixing, the polymer solution (polymer in DMSO) was directly dissolved in 25 mM NaOAc and then mixed with the mRNA. However, not all the polymers are freely soluble in these aqueous phase and small nanoparticles were produced. The addition of the oligonucleotide led to a partial coagulation of these primary NPs into larger nanoaggregates, as visible in FIG. 11. In the second case, the polymer solution was dissolved in ethanol before mixing with mRNA. In this case, referred to as pre-mixing protocol, the NPs were formed during the mixing of the two phases resulting into a higher size compared to the ones obtained with the previous method (see FIG. 11).

Figure 10B:
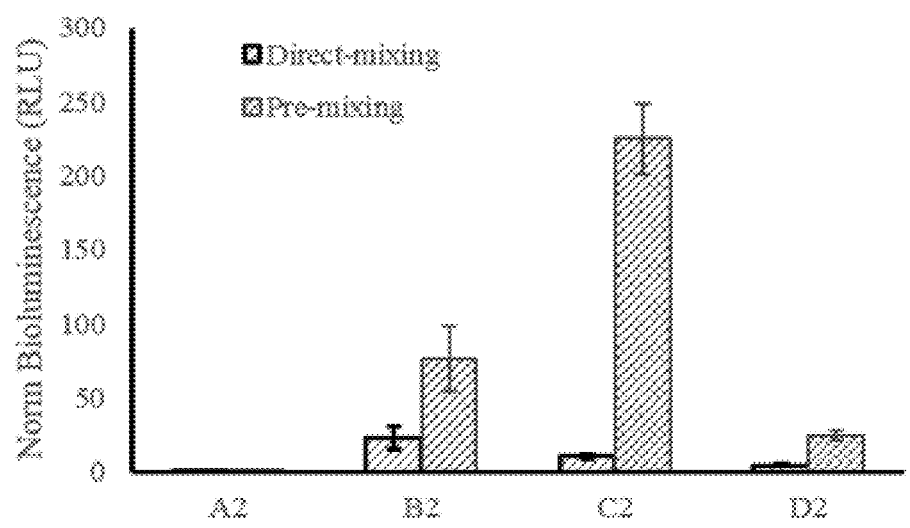
Figure 10C:
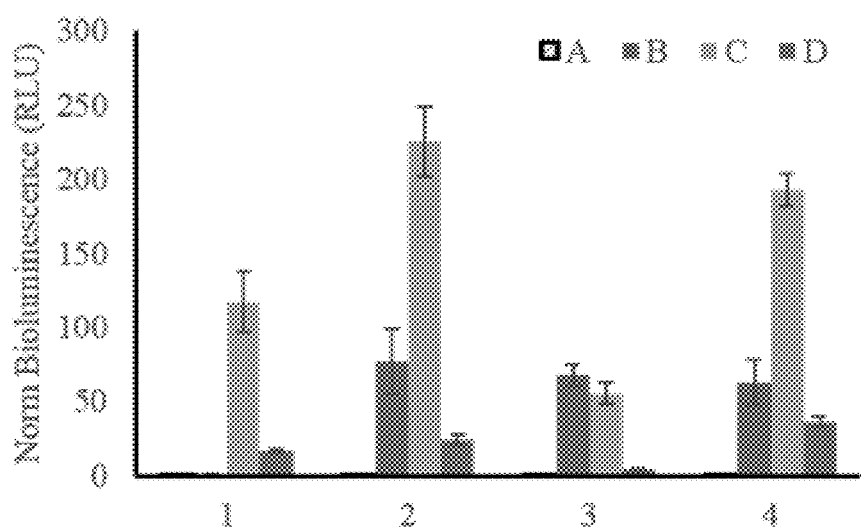
Figure 10D:
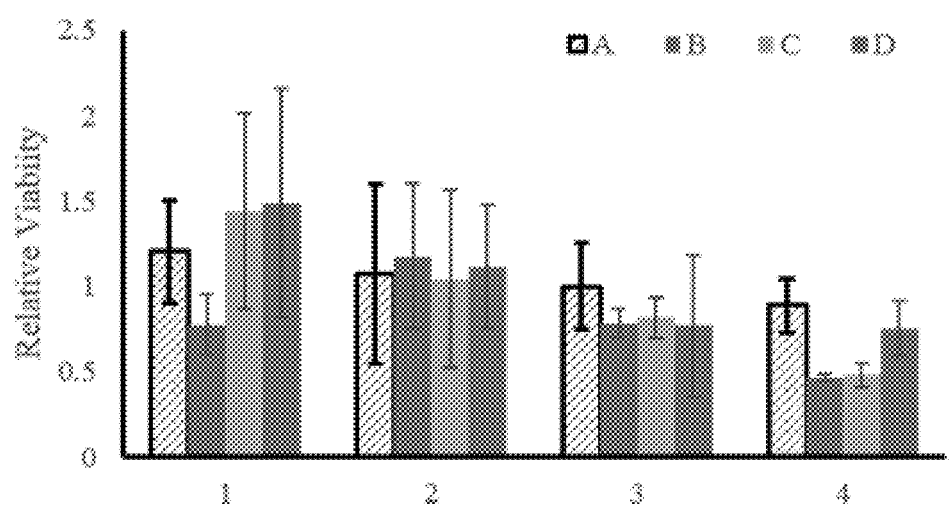

However, as shown in FIG. 10B, all the NPs generated with the pre-mixing protocol show a higher transfection efficiency compared to the ones obtained via direct mixing. This effect is more enhanced where the lipophilicity of the polymers is higher, and underscores the importance of formulation conditions, in addition to material synthesis, when conducting material screens. Thus, in order to find the best performing materials in the screening of the PBAE library, the pre-mixing procedure was applied to all the polymers, which were then used to transfect HeLa cells (see FIG. 10C). A dependence on the lipophilicity of the polymer on the transfection efficiency can be seen in all the tested formulations. In particular, the less lipophilic PBAEs that are based only on the A diacrylate show little efficacy in mRNA delivery while the initial increase in the number of the CL units (q) leads to a higher transfection. However, as mentioned previously, the beneficial impact of the increased lipophilicity is counterbalanced by the reduction in the density of ionizable amines that are necessary to correctly condense the mRNA. When this reduction is too high, it affects the transfection, as clearly visible in the polymers made with the D. In addition, as visible in the cell viability test in FIG. 10D, almost all the tested polymers are non-toxic despite the lack of a wash step following transfection.

The high transfection efficacy of most of these polymers can also be ascribed to their ability to form relative small and mono-disperse nanoparticles in PBS, as visible in FIG. 12.

Figure 13A:
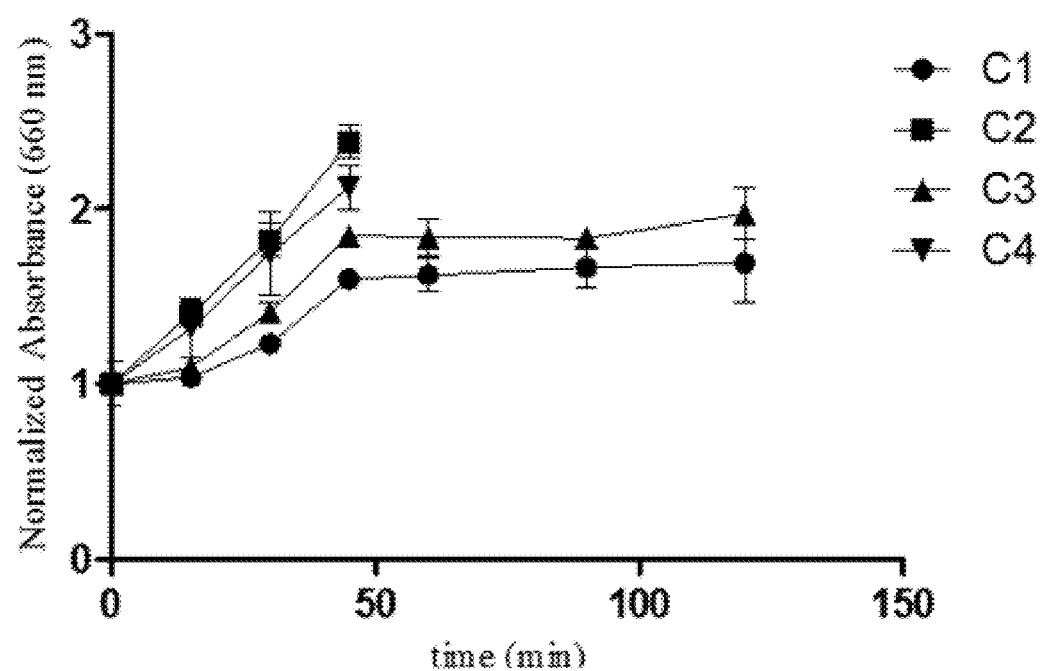
FIGS. 13A to 13F show.
Figure 13B:
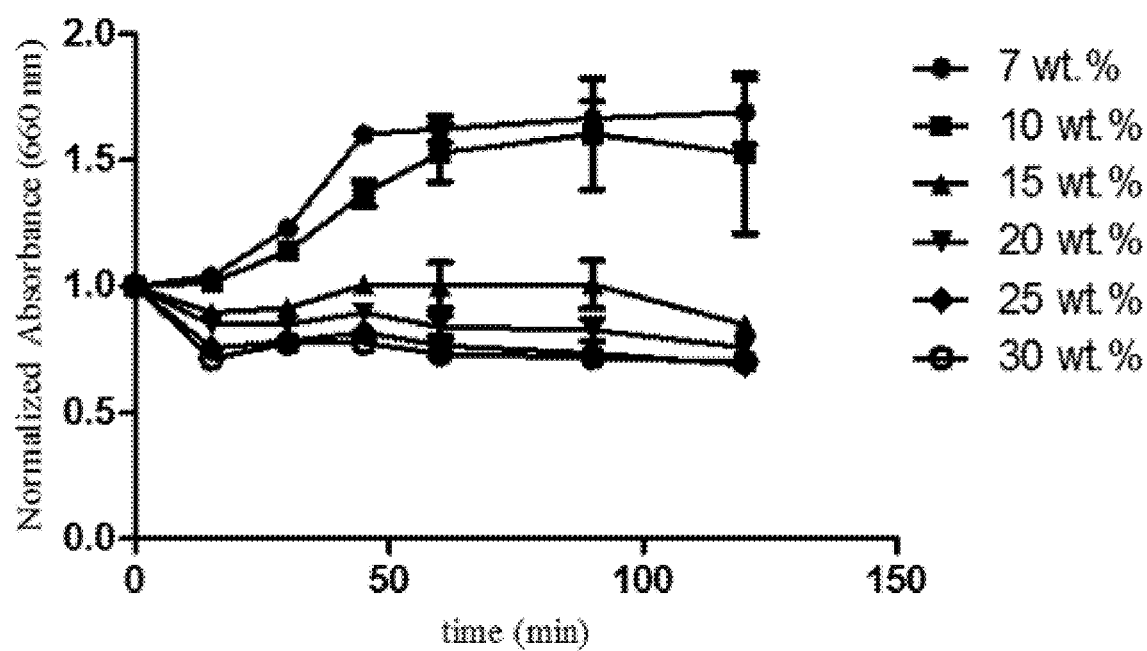

However, the stability of the NPs in biologically relevant fluid is a more crucial property for applications in which a systemic delivery of the mRNA is required. For this reason, the top performing polymers were co-formulated with 7 wt. % of a polyethylene glycol-modified lipid (PEG-lipid) and the stability of the resulting NPs were tested in a mixture of 10% fetal bovine serum (FBS) according to a previous protocol.[29] Briefly, the NPs were incubated at 37° C. and the optical clarity of the solution was evaluated at different time points (see FIG. 13A). Among the C derived polymers, the C1 showed the best stability and was therefore optimized in order to find the minimum amount of PEG-lipid that led to no change in the absorbance once incubated with the FBS (see FIG. 13B).

Figure 14A:
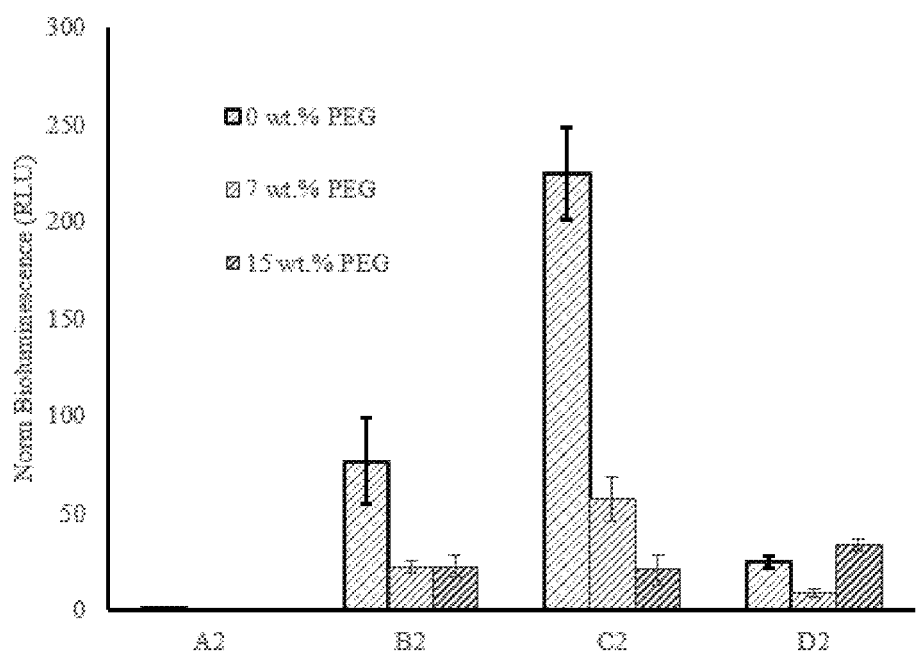
FIGS. 14A to 14B show.
Figure 14B:
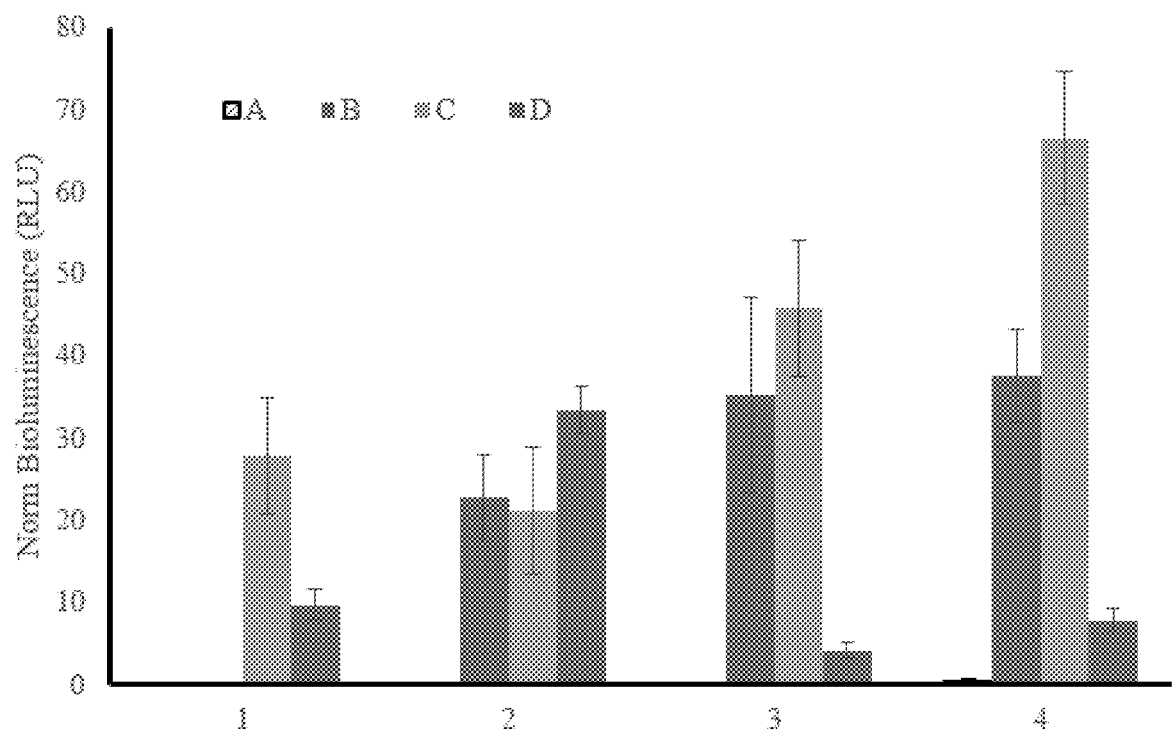

The increase in PEG-lipid led to a higher stability, but at the same time it reduced the transfection efficacy of the NP formulation due to the charge shielding effect of the PEG tails, as already reported in literature[29] and also demonstrated in FIGS. 14A and 14B.

Figure 13C:
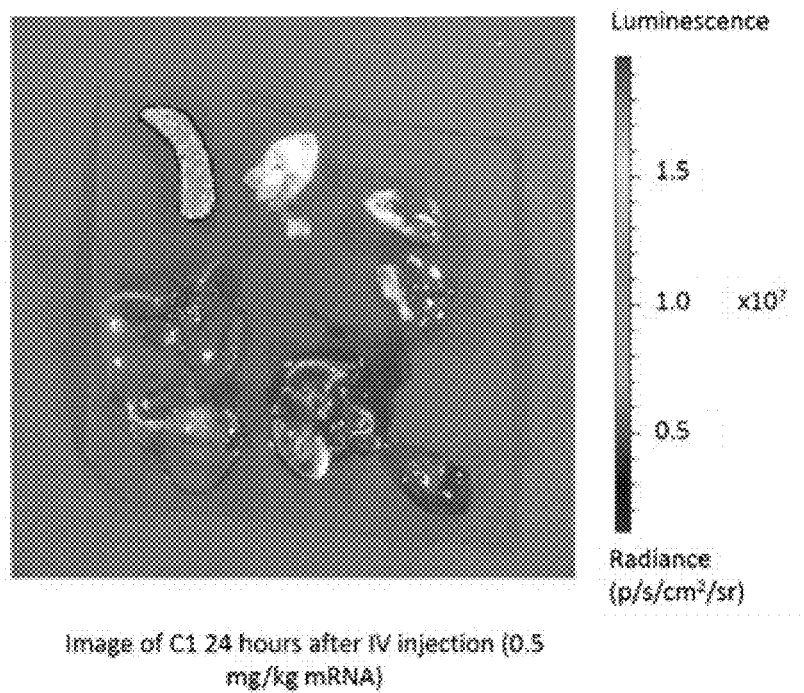
Figure 13D:
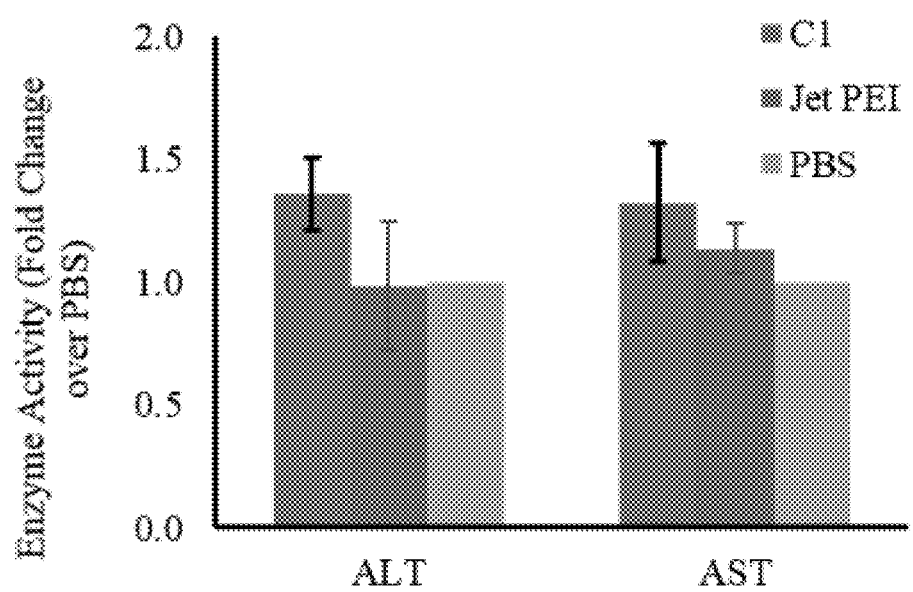
Figure 13E:
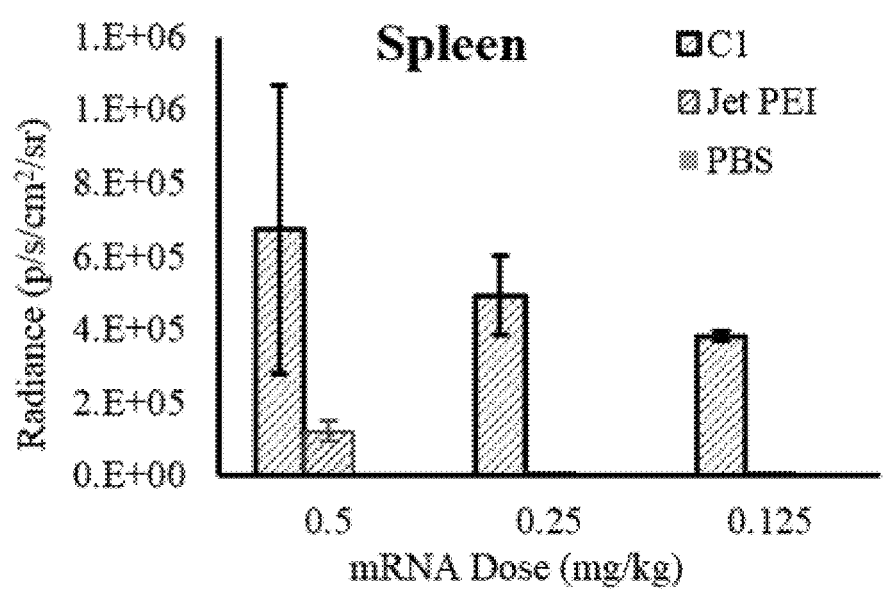
Figure 13F:
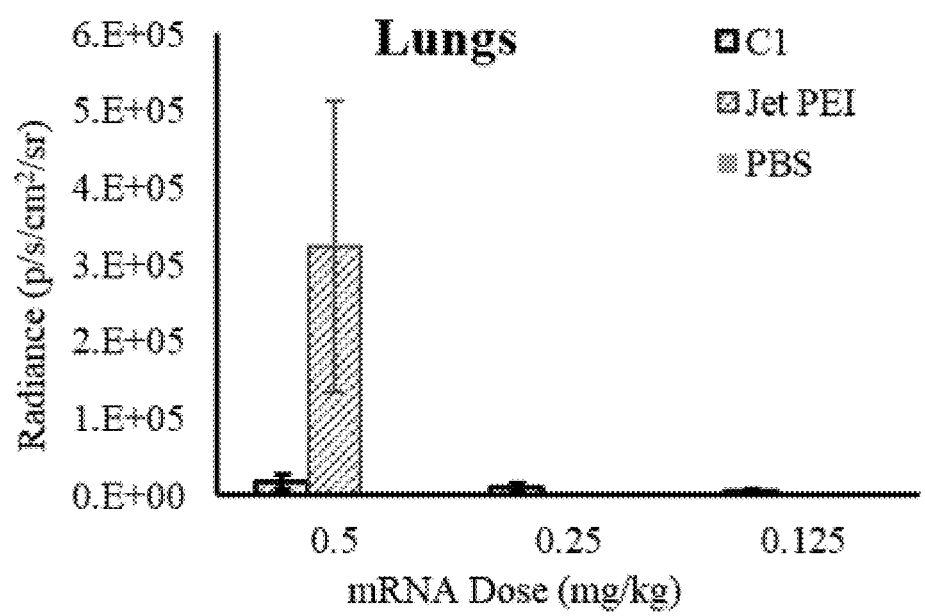
Figure 15:
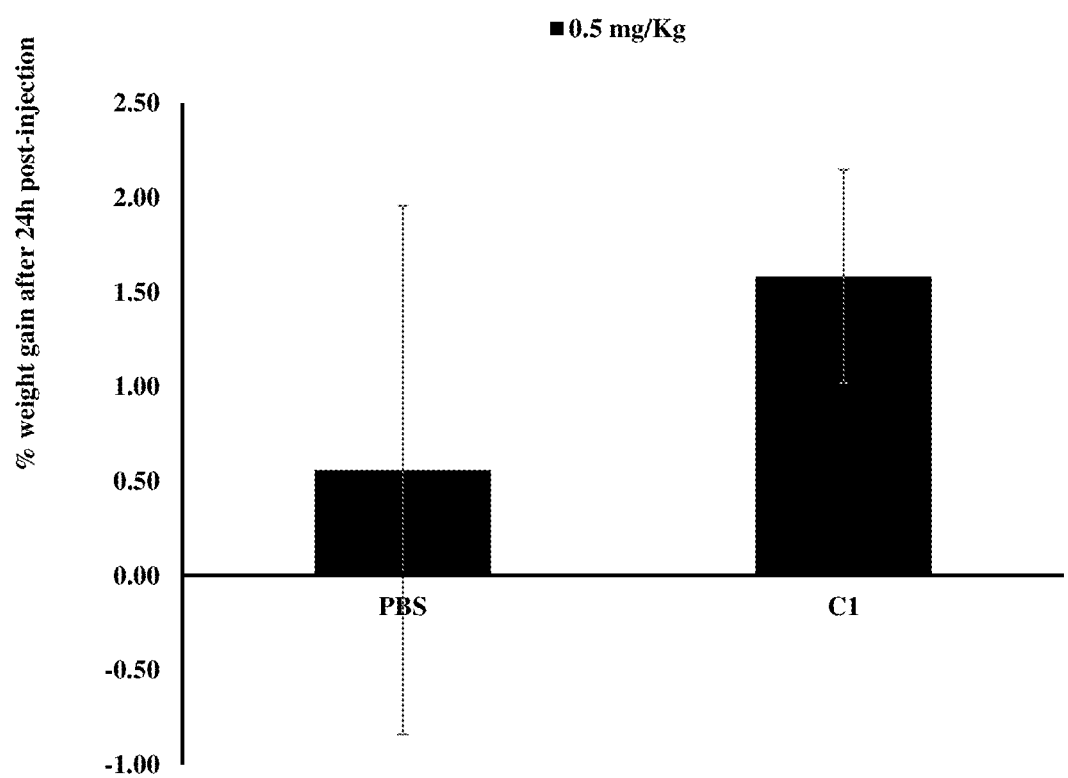
FIG. 15 shows percent weight gain for C1 nanoparticles. Data are presented as mean±SD, n=3.

However, as serum stability is critical for effective systemic delivery of PBAE polymers,[29] C1 was formulated with 15 wt % PEG-lipid for in vivo testing with an mRNA coding for firefly luciferase. The stable C1 was injected in mice at three different doses (0.5, 0.25 and 0.125 mg/kg mRNA) and their efficacy and toxicity compared with PEI. Interestingly, this PCL-based polymer has been found to work selectively into the spleen (see FIG. 13C) in contrast with other members of the PBAE family[29] that also show activity into the lungs, as well as lipid nanoparticles that are typically effective in the liver.[30,31] In addition, even at the highest tested concentration, there is no significant difference in body weight (see FIG. 15) or in levels of the liver enzymes ALT and AST compared to PBS (p>0.05) indicating little systemic toxicity caused by the polymer (see FIG. 13D). The efficacy of the C1 is also higher in the spleen, as well as more specifically targeted, compared to PEI at all the tested concentrations, and also possesses a much wider therapeutic window overall (see FIGS. 13E and 13F).

Given its spleen-targeting capability, this novel class of PBAE polymers may be used as novel biodegradable and biocompatible carriers for the intravenous delivery of antigen-encoding RNA for cancer immunotherapy and vaccination, as recently shown with a non-biodegradable lipid formulation.[32]

A new synthesis for the production of well controlled poly-caprolactone based diacrylates has been developed. The versatility of this method has been demonstrated by varying the number of caprolactone units attached to each diacrylate and is to some extent reflected in the characteristics of the PBAE polymers synthesized from them via step-growth polymerization. The ability of the novel PCL-based PBAE materials to deliver mRNA has been shown to depend on the physiochemical characteristics of the material, such as lipophilicity, as well as the formulation method used to complex the polymer with the oligonucleotide. This latter variable represents a previously unstudied aspect of PBAE library screens that could play an important role in identifying true top candidates for nucleic acid delivery. The most stable polymer, the C1, was injected via IV in mice and showed a transfection efficacy several times higher than the PEI and selectively to the spleen, opening the possibility to use a completely biodegradable and biocompatible carrier in the intravenously delivery of antigen-encoding mRNA for cancer immunotherapy and vaccination. The adoption of a controlled living polymerization for the synthesis of more biocompatible and more biodegradable custom diacrylates from other lactones will lead to the synthesis of more versatile PBAE polymers with more controlled properties, higher efficacy and lower toxicity for a variety of applications.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Jin, L.; Zeng, X.; Liu, M.; Deng, Y.; He, N.: Current Progress in Gene Delivery Technology Based on Chemical Methods and Nano-carriers. *Theranostics* 2014, 4, 240-255.
2. Sergeeva, O.; Koteliansky, V.; Zatsepin, T.: mRNA-based therapeutics-Advances and perspectives. *Biochemistry (Moscow)* 2016, 81, 709-722.
3. Mulligan, R. C.: The Basic Science of Gene Therapy. *Science*, 1993, 260, 926-932.
4. [No authors listed]: HIV Vaccine Failure Prompts Merck to Halt Trial. *Nature*, 2007, 449, 390.
5. Robinson, H. L.; Pertmer, T. M.: Nucleic acid immunizations. *Curr. Protoc. Immunol.* 2001, Chapter 2: Unit 2.14.
6. Vu, L.; Ramos, J.; Potta, T.; Rege, K.: Generation of a Focused Poly (amino ether) Library: Polymer-mediated Transgene Delivery and Gold-nanorod Based Theranostic Systems. *Theranostics*. 2012, 2, 1160-1173.
7. Khosravi-Darani, K.; Mozafari, M. R.; Rashidi, L.; Mohammadi, M.: Calcium Based Non-viral Gene Delivery: An Overview of Methodology and Applications. *Acta Med Iranica*, 2010, 48, 133-141.
8. Luten, J.; van Nostrum, C. F.; De Smedt, S. C.; Hennink, W. E.: Biodegradable Polymers as Non-viral Carriers for Plasmid DNA Delivery. *J Control Release*, 2008, 126, 97-110.
9. (a) Zhou, D.; Gao, Y.; Aied, A.; Cutlar, L.; Igoucheva, O.; Newland, B.; Alexeeve, V.; Greiser, U.; Uitto, J.; Wang, W.: Highly Branched Poly (β-amino ester)s for Skin Gene Therapy. *Journal of Controlled Release*, 2016, 244, 336-346; (b) Sunshine, J.; Green, J. J.; Mahon, K. P.; Yang, F.; Eltoukhy, A. A.; Nguyen, D. N.; Langer, R.; Anderson, D. G.: Small-Molecule End-Groups of Linear Polymer Determin Cell-type Gene-Delivery Efficacy. *Advanced Materials*, 2009, 21, 4947-4951; (c) Tzeng, S. Y.; Hung, B. P.; Grayson, W. L.; Green, J. J.: Cystamine-terminated Poly (beta-amino ester)s for siRNA Delivery to Human Mesenchymal Stem Cells and Enhancement of Osteogenic Differentiation. *Biomaterials*, 2012, 33, 8142-8151; (d) Kim, J.; Sunshine, J. C.; Green, J. J.: Differential polymer Structure Tunes Mechanism of Cellular Uptake and Transfection Routes of Poly (β-amino ester) Polyplexes in Human Breast Cancer Cells. *Bioconjugate Chemistry*, 2013, 25, 43-51; (e) Guerrero-Cázares, H.; Tzeng, S. Y.; Young, N. P.; Abutaleb, A. O.; Quiñones-Hinojosa, A.; Green, J. J.: Biodegradable Polymeric Nanoparticles Show High Efficacy and Specificity at DNA Delivery to Human Glioblastoma in Vitro and in Vivo. *ACS Nano*, 2014, 8, 5141-5153; (f) Eltoukhy, A. A.; Chen, D.; Alabi, C. A.; Langer, R.; Anderson, D. G.: Degradable Terpolymers with Alkyl Side Chains Demonstrate Enhanced Gene Delivery Potency and Nanoparticle Stability. *Advanced Materials*, 2013, 25, 1487-1493.
10. (a) Zhao, J.; Huang, P.; Wang, Z.; Tan, Y.; Hou, X.; Zhang, L.; He, C.-Y.; Chen, Z.-Y.: Synthesis of Amphiphilic Poly (β-amino ester) for Efficiently Minicircle DNA Delivery in Vivo. *ACS Applied Materials & Interfaces*, 2016, 8, 19284-19290; (b) Sunshine, J. C.; Sunshine, S. B.; Bhutto, I.; Handa, J. T.; Green, J. J.: Poly (β-amino ester)-nanoparticle Mediated Transfection of Retinal Pigment Epithelial Cells in Vitro and in Vivo. *PloS one*, 2012, 7, e37543; (c) Mangraviti, A.; Tzeng, S. Y.; Kozielski, K. L.; Wang, Y.; Jin, Y.; Gullotti, D.; Pedone, M.; Buaron, N.; Liu, A.; Wilson, D. R.: Polymeric Nanoparticles for Nonviral Gene Therapy Extend Brain Tumor Survival in Vivo. *ACS Nano*, 2015, 9, 1236-1249; (d) Kamat, C. D.; Shmueli, R. B.; Connis, N.; Rudin, C. M.: Lung Cancer in Vitro and in Vivo. *Molecular Cancer Therapeutics*, 2013, 12, 405-415.
11. (a) Carai, M. A. M.; Colombo, G.; Reali, R.; Serra, S.; Mocci, I.; Castelli, M. P.; Cignarella, G.; Gessa, G. L.: Central Effects of 1,4-Butanediol are Mediated by GABA (B) Receptors via its Conversion into γ-Hydroxybutyric Acid. *European Journal of Pharmacology*, 2002, 441, 157-163; (b) Satta, R.; Dimitrijevic, N.; Manev, H.: *Drosophila* Metabolize 1,4-Butanediol into γ-Hydroxybutyric Acid in Vivo. *European Journal of Pharmacology*, 2003, 473, 149-152.
12. (a) Gore, A. C.; Chappell, V. A.; Fenton, S. E.; Flaws, J. A.; Nadal, A.; Prins, G. S.; Toppari, J.; Zoeller, R. T.: Executive Summary to EDC-2: The Endocrine Society's Second Scientific Statement on Endocrine-Disrupting Chemicals. *Endocrine Reviews*, 2015, 36, 593-602; (b) Mirmira, P.; Evans-Molina, C.: Bisphenol A, Obesity, and Type 2 Diabetes Mellitus: Genuine Concern or Unnecessary Preoccupation? *Translational Research*, 2014, 164, 13-21.
13. Chen, J.; Guo, Z.; Tian, H.; Chen, X.: Production and Clinical Development of Nanoparticles for Gene Delivery. *Mol. Ther. Methods Clin. Dev.*, 2016, 3, 16023.
14. (a) Kumari, A.; Yadav, S. K.; Yadav, S. C.: Biodegradable Polymeric Nanoparticles Based Drug Delivery Systems. *Colloids and Surfaces B: Biointerfaces*, 2010, 75, 1-18; (b) Bobo, D.; Robinson, K. J.; Islam, J.; Thurecht, K. J.; Corrie, S. R.: Nanoparticle-Based Medicines: A Review of FDA-Approved Materials and Clinical Trials to Date. *Pharmaceutical Research,* 2016, 33, 2373-2387.
15. Dash, T. K.; Konkimalla, V. B.: Poly-ε-caprolactone Based Formulations for Drug Delivery and Tissue Engineering: A Review. *Journal of Controlled Release,* 2012, 158, 15-33.
16. Gilboa, E.; Vieweg, J.: Cancer Immunotherapy with mRNA-transfected Dendritic Cells. *Immunological Reviews,* 2004, 199, 251-263.
17. McNamara, M. A.; Nair, S. K.; Holl, E. K.: RNA-based Vaccines in Cancer Immunotherapy. *Journal of Immunology Research,* 2015, 2015.
18. Matsui, A.; Uchida, S.; Ishii, T.; Itaka, K.; Kataoka, K.: Messenger RNA-based Therapeutics for the Treatment of Apoptosis-associated Diseases. *Scientific Reports* 2015, 5.
19. Weiss, R.; Scheiblhofer, S.; Roesler, E.; Weinberger, E.; Thalhamer, J.: mRNA Vaccination as a Safe Approach for Specific Protection from Type I Allergy. *Expert Review of Vaccines,* 2012, 11, 55-67.
20. Pollard, C.; De Koker, S.; Saelens, X.; Vanham, G.; Grooten, J.: Challenges and Advances Towards the Rational Design of mRNA Vaccines. *Trends in Molecular Medicine,* 2013, 19, 705-713.
21. Wang, H.; Yang, H.; Shivalila, C. S.; Dawlaty, M. M.; Cheng, A. W.; Zhang, F.; Jaenisch, R.: One-step Generation of Mice Carrying Mutations in Multiple Genes by CRISPR/Cas-mediated Genome Engineering. *Cell,* 2013, 153, 910-918.
22. Hashimoto, M.; Takemoto, T.: Electroporation Enables the Efficient mRNA Delivery into the Mouse Zygotes and Facilitates CRISPR/Cas9-based Genome Editing. *Scientific Reports,* 2015, 5.
23. Gori, J. L.; Hsu, P. D.; Maeder, M. L.; Shen, S.; Welstead, G. G.; Bumcrot, D.: Delivery and Specificity of CRISPR/Cas9 Genome Editing Technologies for Human Gene Therapy. *Human Gene Therapy,* 2015, 26, 443-451.
24. Kaczmarek, J. C.; Patel, A. K.; Kauffman, K. J.; Fenton, O. S.; Webber, M. J.; Heartlein, M. W.; DeRosa, F.; Anderson, D. G.: Polymer-Lipid Nanoparticles for Systemic Delivery of mRNA to the Lungs. *Angewandte Chemie,* 2016, 55, 13808-13812.
25. Ferrari, R.; Yu, Y.; Morbidelli, M.; Hutchinson, R. A.; Moscatelli, D.: ε-Caprolactone-based Macromonomers Suitable for Biodegradable Nanoparticles Synthesis Through Free Radical Polymerization. *Macromolecules,* 2011, 44, 9205-9212.
26. Sunshine, J.; Green, J. J.; Mahon, K. P.; Yang, F.; Eltoukhy, A. A.; Nguyen, D. N.; Langer, R.; Anderson, D. G.: Small-Molecule End-Groups of Linear Polymer Determine Cell-type Gene-Delivery Efficacy. *Advanced Materials,* 2009, 21, 4947-4951.
27. Eltoukhy, A. A.; Siegwart, D. J.; Alabi, C. A.; Rajan, J. S.; Langer, R.; Anderson, D. G., Effect of Molecular Weight of Amine End-modified Poly (β-amino ester) s on Gene Delivery Efficiency and Toxicity. *Biomaterials.* 2012, 33, 3594-3603.
28. Carothers, W. H.: Polymers and Polyfunctionality. *Transactions of the Faraday Society,* 1936, 32, 39-49.
29. Kaczmarek, J. C.; Patel, A. K.; Kauffman, K. J.; Fenton, O. S.; Webber, M. J.; Heartlein, M. W.; DeRosa, F.; Anderson, D. G.: Polymer-Lipid Nanoparticles for Systemic Delivery of mRNA to the Lungs. *Angewandte Chemie,* 2016, 55, 13808-13812.
30. Kauffman, K. J.; Dorkin, J. R.; Yang, J. H.; Heartlein, M. W.; DeRosa, F.; Mir, F. F.; Fenton, O. S.; Anderson, D. G.: Optimization of Lipid Nanoparticle Formulations for mRNA Delivery in Vivo with Fractional Factorial and Definitive Screening Designs. *Nano letters,* 2015, 15, 7300-7306.
31. Fenton, O. S.; Kauffman, K. J.; McClellan, R. L.; Appel, E. A.; Dorkin, J. R.; Tibbitt, M. W.; Heartlein, M. W.; DeRosa, F.; Langer, R.; Anderson, D. G.: Bioinspired Alkenyl Amino Alcohol Ionizable Lipid Materials for Highly Potent in Vivo mRNA Delivery. *Advanced Materials,* 2016, 28, 2939-2943.
32. Kranz, L. M.; Diken, M.; Haas, H.; Kreiter, S.; Loquai, C.; Reuter, K. C.; Meng, M.; Fritz, D.; Vascotto, F.; Hefesha, H.: Systemic RNA Delivery to Dendritic Cells Exploits Antiviral Defense for Cancer Immunotherapy. *Nature,* 2016, 534, 396-401.

What is claimed is:

1. A polymer of Formula (I):

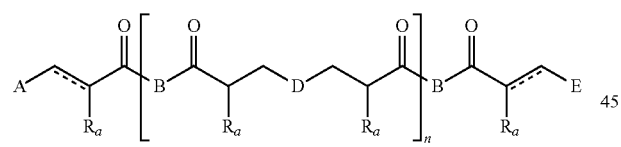

or a pharmaceutically acceptable salt thereof,
wherein:
≡≡≡ is a single bond or a double bond;
A is hydrogen or —$XR_3$;
each B independently is a diradical of the formula:

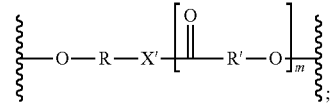

each D independently is:

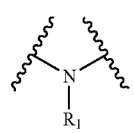

E is —$XR_4$;
R is $C_2$-$C_6$ alkyl;

R' is $C_2$-$C_{20}$ alkyl, optionally substituted with a group selected from alkyl, heteroalkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide;

R" cyclic or acyclic aliphatic, cyclic or acyclic heteroaliphatic, or a combination thereof, wherein each aliphatic or heteroaliphatic is optionally substituted with a $C_{1-6}$ alkyl;

each $R_a$ independently is hydrogen or $C_{1-6}$ alkyl;

each $R_1$ independently is selected from hydrogen, $C_1$-$C_{10}$ alkyl, and $C_1$-$C_{20}$ heteroalkyl, wherein the alkyl and heteroalkyl groups are optionally substituted with halogen, hydroxyl, $C_{3-10}$ carbocyclyl, 3-14 membered heterocyclyl, $C_{6-14}$ aryl, or 5-14 membered heteroaryl;

$R_3$ and $R_4$ independently are selected from hydrogen, $C_1$-$C_{20}$ alkyl, $C_1$-$C_{10}$ heteroalkyl, $C_{3-10}$ carbocyclyl, and 3-14 membered heterocyclyl;

X is O, S, NH, or $NR_X$, wherein $R_X$ is $C_{1-6}$ alkyl;

X' is O;

each m independently is an integer between 3 and 10, inclusive; and n is an integer between 1 and 10,000, inclusive.

2. The polymer of claim 1, having the structure of Formula (II):

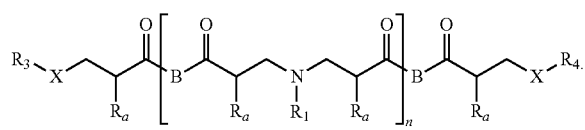
(II)

3. The polymer of claim 1, wherein B is of the formula:

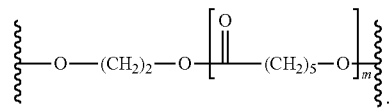

4. The polymer of claim 1, wherein m is an integer between 3 and 7, inclusive.

5. The polymer of claim 1, wherein the polymer is of the formula:

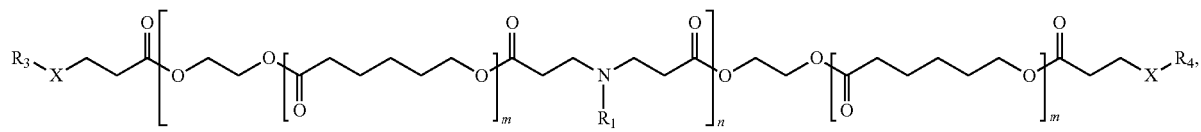

wherein:
each $R_1$ is independently

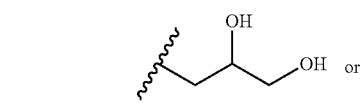

at least one $R_1$ is

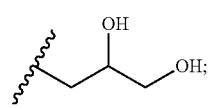 [SMILES: *CC(O)CO]

and
at least one $R_1$ is

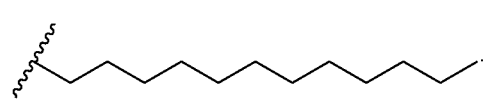 [SMILES: *CCCCCCCCCCCC]

6. The polymer of claim 1, wherein the polymer is of the formula:

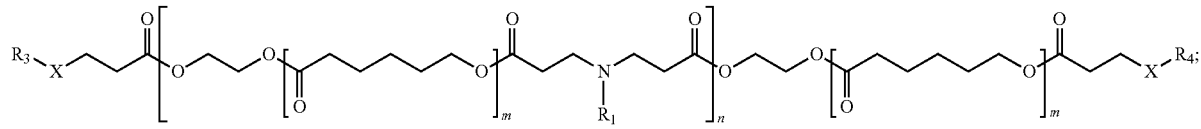

wherein:
each $R_1$ is independently

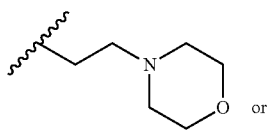
or

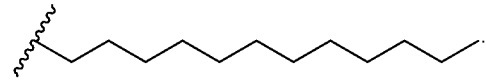

at least one $R_1$ is

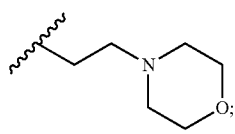 [SMILES: *CCN1CCOCC1]

and
at least one $R_1$ is

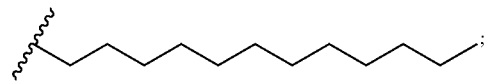 [SMILES: *CCCCCCCCCCCC]

7. The polymer of claim 1, wherein the polymer is of the formula:

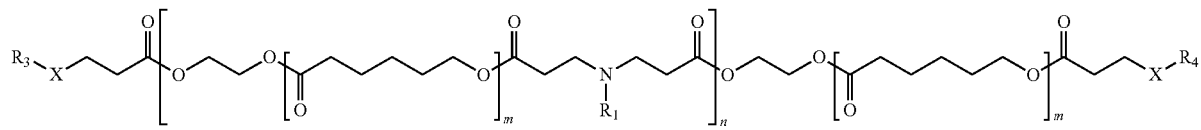

wherein:
each $R_1$ is independently

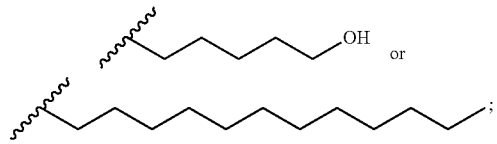

at least one $R_1$ is

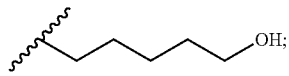 [SMILES: *CCCCCO]

and
at least one $R_1$ is

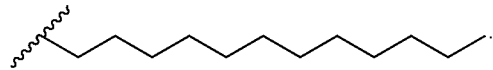 [SMILES: *CCCCCCCCCCCC]

8. The polymer of claim 1, wherein the polymer is of the formula:

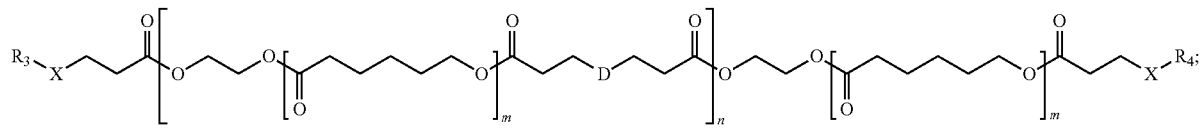

wherein:
each D is independently

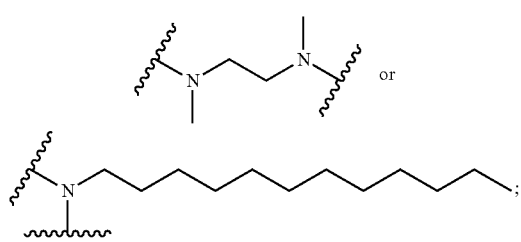

at least one D is

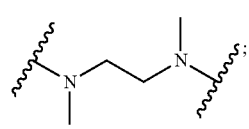 [SMILES: *N(C)CCN(*)C]

and
at least one D is

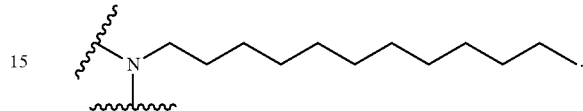

9. The polymer of claim 1, wherein the polymer has a molecular weight between 1-100 kDa.

10. A composition comprising a polymer of claim 1 and an excipient.

11. The composition of claim 10, wherein the composition further comprises an agent.

12. The composition of claim 11, wherein the agent is a polynucleotide.

13. The composition of claim 12, wherein the polynucleotide is DNA.

14. The composition of claim 12, wherein the polynucleotide is RNA.

15. The composition of claim 14, wherein the RNA is dsRNA, siRNA, shRNA, miRNA, mRNA, or antisense RNA.

16. The composition of claim 14, wherein the RNA is mRNA.

17. The composition of claim 16, wherein the mRNA encodes an antigen.

18. The composition of claim 12, wherein the polynucleotide carries out RNA interference.

19. The composition of claim 10, wherein the composition is in the form of a particle.

20. The composition of claim 19, wherein the particle encapsulates an agent.

21. The polymer of claim 5, wherein:
m=3, n is about 5, each X is —NH—, and $R_3$ and $R_4$ are both

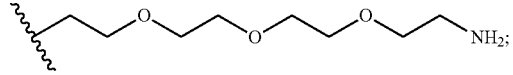 [SMILES: *CCOCCOCCOCCN]

m=5, n is about 5, each X is —NH—, and $R_3$ and $R_4$ are both

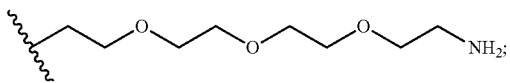 [SMILES: *CCOCCOCCOCCN]

or m=7, n is about 5, each X is —NH—, and $R_3$ and $R_4$ are both

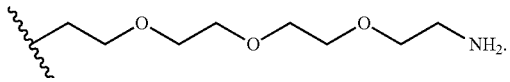 [SMILES: *CCOCCOCCOCCN]

22. The polymer of claim 6, wherein:

m=3, n is about 5, each X is —NH—, and $R_3$ and $R_4$ are both

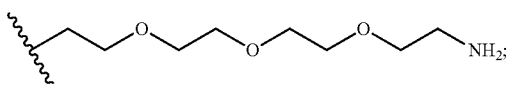 [SMILES: *CCOCCOCCOCCN]

m=5, n is about 5, each X is —NH—, and $R_3$ and $R_4$ are both

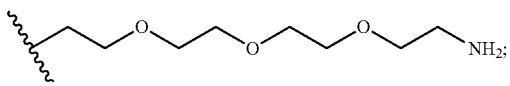 [SMILES: *CCOCCOCCOCCN]

or m=7, n is about 5, each X is —NH—, and $R_3$ and $R_4$ are both

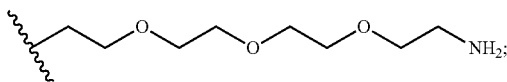 [SMILES: *CCOCCOCCOCCN]

23. The polymer of claim 7, wherein:

m=3, n is about 5, each X is —NH—, and $R_3$ and $R_4$ are both

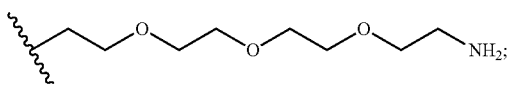 [SMILES: *CCOCCOCCOCCN]

m=5, n is about 5, each X is —NH—, and $R_3$ and $R_4$ are both

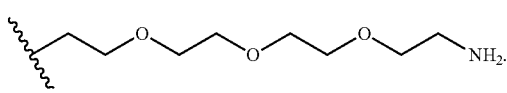 [SMILES: *CCOCCOCCOCCN]

or m=7, n is about 5, each X is —NH—, and $R_3$ and $R_4$ are both

* * * * *

UNITED STATES PATENT AND TRADEMARK OFFICE
CERTIFICATE OF CORRECTION

PATENT NO. : 11,041,069 B2  Page 1 of 1
APPLICATION NO. : 16/179698
DATED : June 22, 2021
INVENTOR(S) : Umberto Capasso Palmiero et al.

It is certified that error appears in the above-identified patent and that said Letters Patent is hereby corrected as shown below:

In the Claims

In Claim 8, at Column 113, Line 46, the following text:

"each D is independently 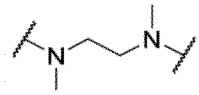 or 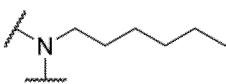 ;

at least one D is 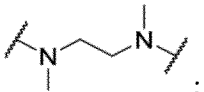 ; and at least one D is 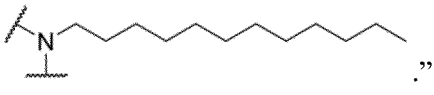 ."

Should be replaced with:

"each D is 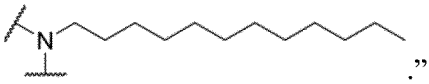 ."

Signed and Sealed this
Seventh Day of September, 2021

Drew Hirshfeld
*Performing the Functions and Duties of the
Under Secretary of Commerce for Intellectual Property and
Director of the United States Patent and Trademark Office*